US009469633B2

(12) United States Patent
Smejkal et al.

(10) Patent No.: US 9,469,633 B2
(45) Date of Patent: Oct. 18, 2016

(54) PROCESSES FOR THE PREPARATION OF PYRROLIDINE INTERMEDIATES

(71) Applicant: SYNGENTA PARTICIPATIONS AG, Basel (CH)

(72) Inventors: Tomas Smejkal, Stein (CN); Helmars Smits, Stein (CH); Sebastian Volker Wendeborn, Stein (CH); Guillaume Berthon, Stein (CH); Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/346,773

(22) PCT Filed: Sep. 28, 2012

(86) PCT No.: PCT/EP2012/069171
§ 371 (c)(1),
(2) Date: Mar. 24, 2014

(87) PCT Pub. No.: WO2013/050301
PCT Pub. Date: Apr. 11, 2013

(65) Prior Publication Data
US 2014/0296527 A1 Oct. 2, 2014

Related U.S. Application Data

(60) Provisional application No. 61/576,135, filed on Dec. 15, 2011.

(30) Foreign Application Priority Data

Oct. 3, 2011 (WO) .................. PCT/EP2011/067224

(51) Int. Cl.
*C07D 207/408* (2006.01)
*C07D 207/40* (2006.01)
(Continued)

(52) U.S. Cl.
CPC ........... *C07D 453/04* (2013.01); *C07C 253/10* (2013.01); *C07C 253/30* (2013.01); *C07C 255/40* (2013.01); *C07C 255/41* (2013.01); *C07D 207/08* (2013.01);
(Continued)

(58) Field of Classification Search
CPC ............ C07D 207/408; C07D 207/40; C07D 207/404; C07D 207/412; C08F 8/32
USPC .......................................... 548/545; 546/134
See application file for complete search history.

(56) References Cited

FOREIGN PATENT DOCUMENTS

EP 2230230 A1 9/2010
JP 2008110971 A * 5/2008
(Continued)

OTHER PUBLICATIONS

Tanaka et al., Journal of the American Chemical Society, vol. 132, No. 26, Jul. 7, 2010, 8862-8863.
(Continued)

*Primary Examiner* — Alicia L Otton
*Assistant Examiner* — Sagar Patel
(74) *Attorney, Agent, or Firm* — Brian D. McAlhaney

(57) ABSTRACT

The present invention relates to processes for the enantioselective preparation of spyrrolidine derivatives useful in the manufacture of pesticidally active compounds, as well as to intermediates in the processes. The processes include those comprising
(a-i) reacting a compound of formula Ia

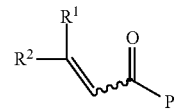

(Ia)

wherein
P is alkyl, aryl or heteroaryl, each optionally substituted, wherein the heteroaryl is connected at P via a ring carbon atom;
$R^1$ is chlorodifluoromethyl or trifluoromethyl;
$R^2$ is aryl or heteroaryl, each optionally substituted;
with a source of cyanide in the presence a chiral catalyst to give a compound of formula IIa

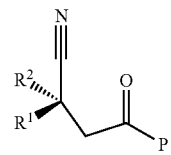

(IIa)

wherein P, $R^1$ and $R^2$ are as defined for the compound of formula Ia; and
(a-ii) oxidizing the compound of formula IIa with a peroxy acid, or peroxide in the presence of an acid to give a compound of formula VI

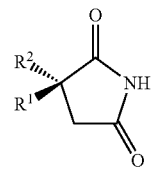

(VI)

wherein $R^1$ and $R^2$ are as defined for the compound of formula Ia.

3 Claims, No Drawings

(51) Int. Cl.
*C07D 207/404* (2006.01)
*C08F 8/32* (2006.01)
*C07D 207/412* (2006.01)
*C07D 207/325* (2006.01)
*C07C 255/41* (2006.01)
*C07C 253/10* (2006.01)
*C07C 253/30* (2006.01)
*C07D 453/04* (2006.01)
*C07D 409/12* (2006.01)
*C07D 207/08* (2006.01)
*C07D 207/267* (2006.01)
*C07D 207/333* (2006.01)
*C07D 307/46* (2006.01)
*C07C 255/40* (2006.01)
*C07D 207/12* (2006.01)

(52) U.S. Cl.
CPC ....... *C07D 207/12* (2013.01); *C07D 207/267* (2013.01); *C07D 207/325* (2013.01); *C07D 207/333* (2013.01); *C07D 207/40* (2013.01); *C07D 307/46* (2013.01); *C07D 409/12* (2013.01)

(56) References Cited

FOREIGN PATENT DOCUMENTS

| WO | WO 2008128711 A1 * | 10/2008 | |
|---|---|---|---|
| WO | WO 2010043315 A1 * | 4/2010 | |
| WO | WO 2010090344 A1 * | 8/2010 | ........... C07D 207/18 |
| WO | 2011/080211 A1 | 7/2011 | |
| WO | 2011/128299 A1 | 10/2011 | |
| WO | 2011/154555 A1 | 12/2011 | |
| WO | 2012/045700 A1 | 4/2012 | |

OTHER PUBLICATIONS

Li et al., Tetrahedron, vol. 67, No. 52, Aug. 27, 2011, 10186-10194.
Kawai et al., Angewandte Chemie International Edition, vol. 51, No. 20, May 14, 2012, 4959-4962.
International Search Report for International Application No. PCT/EP2012/069171.
Matoba et al., Angew. Chem. Int. Ed., 2010, 49, 5762-5766.

* cited by examiner

PROCESSES FOR THE PREPARATION OF PYRROLIDINE INTERMEDIATES

This application is a 371 filing of International Application No. PCT/EP2012/069171, filed Sep. 28, 2012, which claims priority benefit to International Application No. PCT/EP2011/067224 filed Oct. 3, 2011 and U.S. Provisional Patent Application No. 61/576,135 filed Dec. 15, 2011, the contents of all of which are incorporated herein by reference.

The present invention relates to the synthesis of intermediates useful for the preparation of substituted pyrrolidine derivatives, including those having pesticidal activity. The invention relates more particularly to the stereoselective syntheses of these intermediates Certain pyrrolidine derivatives with insecticidal properties are disclosed in, for example WO2008/128711, WO2010043315, WO2011/080211. Such pyrrolidine derivatives include at least one chiral centre at one of the ring members of the pyrrolidine moiety. The present invention provides a process for selectively synthesizing enantiomers of such compounds as well as intermediates that can be used in the synthesis of such compounds.

A route to enantio-enriched intermediates is desirable in view of the differential biological activity of the enantiomers. Use of enantio-enriched intermediates can therefore reduce the amount of active ingredient needed to control key pests, thereby reducing costs and impact on the environment.

Accordingly, in a first aspect the invention provides a process for the enantio-selective preparation of a pyrrolidine derivative comprising (a-i) reacting a compound of formula Ia

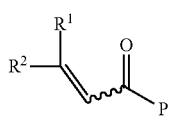

(Ia)

wherein

P is alkyl, aryl or heteroaryl, each optionally substituted, wherein the heteroaryl is connected at P via a ring carbon atom;

$R^1$ is chlorodifluoromethyl or trifluoromethyl;

$R^2$ is aryl or heteroaryl, each optionally substituted;

with a source of cyanide in the presence a chiral catalyst to give a compound of formula IIa

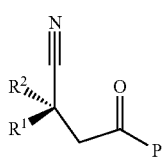

(IIa)

wherein P, $R^1$ and $R^2$ are as defined for the compound of formula Ia; and (a-ii) oxidising the compound of formula IIa with a peroxy acid, or peroxide in the presence of an acid, preferably a strong acid, to give a compound of formula VI

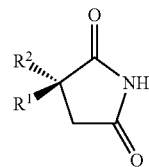

(VI)

wherein $R^1$ and $R^2$ are as defined for the compound of formula Ia.

The ability to prepare compounds of formula VI from compounds of formula IIa via the Baeyer-Villiger oxidation reaction was unexpected and provides an efficient route to enantio-enriched pyrrolidine derivatives, and can also be applied to reactions with racemic mixtures.

In one embodiment step (a-ii) comprises oxidising the compound of formula IIa with a peroxide in the presence of a strong acid to give a compound of formula VI.

In addition, the reaction optionally comprises (a-iii-1) reducing the compound of formula VI with a suitable reducing agent to give a compound of formula IX

(IX)

wherein $R^1$ and $R^2$ are as defined for the compound of formula Ia.

and optionally (a-iv-1) reacting the compound of formula IX with a compound of formula (XIII)

$$X^B\text{-}A'$$ (XIII)

wherein $X^B$ is a leaving group such as halogen, and A' is optionally substituted aryl or optionally substituted heteroaryl to give a compound of formula XVI

(XVI)

wherein $R^1$ and $R^2$ are as defined for the compound of formula Ia and A' is as defined for the compound of formula XIII;

or the reaction optionally comprises (a-iii-2) reacting the compound of formula VI with a compound of formula XIII to give a compound of formula XII

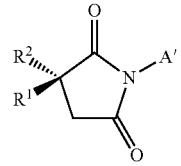

(XII)

wherein $R^1$ and $R^2$ are as defined for the compound of formula Ia and A' is as defined for the compound of formula XIII;

and optionally
(a-iv-2) reducing the compound of formula XII with a suitable reducing agent to give a compound of formula XVI. In a further aspect the invention provides a process for the enantio-selective preparation of a pyrrolidine derivative comprising
(a-1) reacting a compound of formula Ia

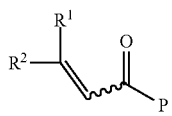
(Ia)

wherein
P is alkyl, aryl or heteroaryl, each optionally substituted, wherein the heteroaryl is connected at P via a ring carbon atom;
$R^1$ is chlorodifluoromethyl or trifluoromethyl;
$R^2$ is aryl or heteroaryl, each optionally substituted;
with a source of cyanide in the presence a chiral catalyst to give a compound of formula IIa

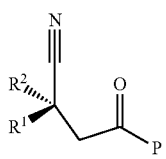
(IIa)

wherein P, $R^1$ and $R^2$ are as defined for the compound of formula Ia; and
(a-2) oxidizing the compound of formula II a with a peroxide to give a compound of formula XVIII

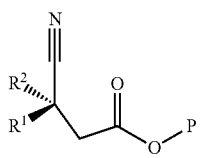
(XVIII)

wherein P, $R^1$ and $R^2$ are as defined for the compound of formula Ia; and
(a-3) reducing the compound of formula XVIII with a suitable reducing agent to give a compound of formula III

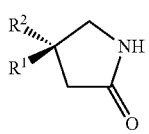
(III)

wherein $R^1$ and $R^2$ are as defined for the compound of formula Ia; and
and wherein the reaction optionally comprises
(a-4-1) reducing the compound of formula III with a suitable reducing agent to give a compound of formula IX

(IX)

wherein $R^1$ and $R^2$ are as defined for the compound of formula Ia;
and optionally
(a-5-1) reacting the compound of formula IX with a compound of formula (XIII)

$X^B$-A'  (XIII)

wherein $X^B$ is a leaving group such as halogen, and A' is optionally substituted aryl or optionally substituted heteroaryl to give a compound of formula XVI

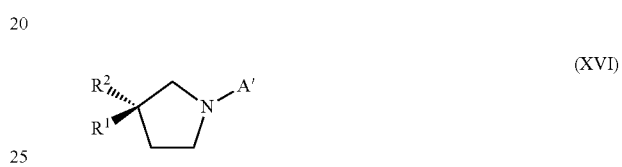
(XVI)

wherein $R^1$ and $R^2$ are as defined for the compound of formula Ia and A' is as defined for the compound of formula XIII;
or the reaction optionally comprises
(a-4-2) reacting the compound of formula III with a compound of formula (XIII) to give a compound of formula XVII

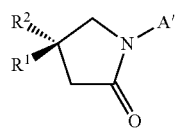
(XVII)

wherein $R^1$ and $R^2$ are as defined for the compound of formula Ia and A' is as defined for the compound of formula XIII;
and optionally
(a-5-2) reducing the compound of formula XVII with a suitable reducing agent to give a compound of formula XVI. In a further aspect the invention provides a process for the enantio-selective preparation of a pyrrolidine derivative comprising
(b-i) reacting a compound of formula Ib

(Ib)

wherein
P is optionally substituted heteroaryl, and wherein the heteroaryl contains at least one ring nitrogen or oxygen atom, wherein the heteroaryl is connected at P via a ring carbon atom;
$R^1$ is chlorodifluoromethyl or trifluoromethyl;
$R^2$ is aryl or heteroaryl, each optionally substituted;

with a source of cyanide in the presence a chiral catalyst to give a compound of formula IIb

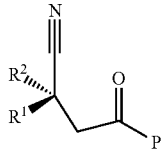
(IIb)

wherein P, R¹ and R² are as defined for the compound of formula Ib; and (b-ii-1) oxidatively cleaving the compound of formula IIb to give a compound of formula XIX

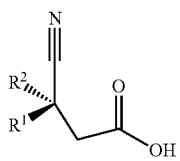
(XIX)

wherein R¹ and R² are as defined for the compound of formula Ib; and (b-ii-2) hydrolysing and dehydrating the compound of formula XIX to give a compound of formula VI

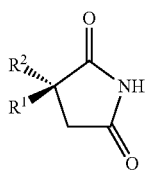
(VI)

wherein R¹ and R² are as defined for the compound of formula Ib;

wherein dehydration is performed in the presence of acid; or (b-ii) reductively cyclising the compound of formula IIb with a suitable reducing agent to give a compound of formula III

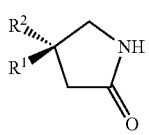
(III)

wherein R¹ and R² are as defined for the compound of formula I.

In a further aspect the invention provides a process for the enantio-selective preparation of a pyrrolidine derivative comprising (c-ii) reductively cyclising the compound of formula IIb with a suitable reducing agent to give a compound of formula III

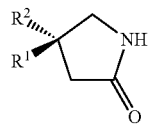
(III)

wherein R¹ and R² are as defined for the compound of formula I;

(c-i) reacting a compound of formula I

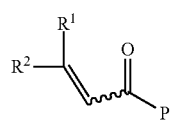
(I)

wherein
P is hydroxy, alkoxy, aryloxy, alkylsulfinyl, arylsulfinyl or heteroaryl, each optionally substituted, and wherein the heteroaryl contains at least one ring nitrogen atom, and the heteroaryl is connected at P via a ring nitrogen atom,
R¹ is chlorodifluoromethyl or trifluoromethyl;
R² is aryl or heteroaryl, each optionally substituted;
with a source of cyanide in the presence a chiral catalyst to give a compound of formula II

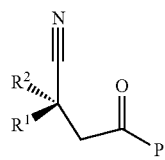
(II)

wherein P, R¹ and R² are as defined for the compound of formula I; and (c-ii) reductively cyclising the compound of formula II with a suitable reducing agent to give a compound of formula III

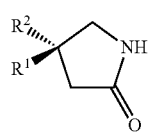
(III)

wherein R¹ and R² are as defined for the compound of formula I; or (c-iii-1) partially hydrolysing the compound of formula II to give a compound of formula V

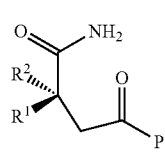
(V)

wherein P, R¹ and R² are as defined for the compound of formula I; and (c-iii-2) cyclising the compound of formula V, e.g. by heating, to give a compound of formula VI

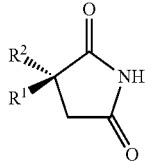
(VI)

wherein $R^1$ and $R^2$ are as defined for the compound of formula I; or
(c-iv-1) hydrolysing the compound of formula II to give a compound of formula VII

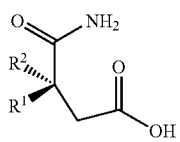
(VII)

wherein $R^1$ and $R^2$ are as defined for the compound of formula I; and
(c-iv-2) cyclising the compound of formula VII, e.g. by heating, to give a compound of formula VI

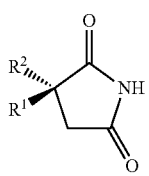
(VI)

wherein $R^1$ and $R^2$ are as defined for the compound of formula I; or
(c-v-1) reducing the compound of formula II with a suitable reducing agent to give a compound of formula VIII

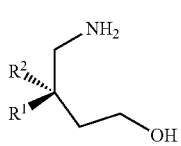
(VIII)

wherein $R^1$ and $R^2$ are as defined for the compound of formula I; and
(c-v-2) treating the compound of formula VIII with a suitable activating agent to give a compound of formula IX

(IX)

wherein $R^1$ and $R^2$ are as defined for the compound of formula I; or (c-vi-1) hydrolysing the compound of formula II to give a compound of formula X

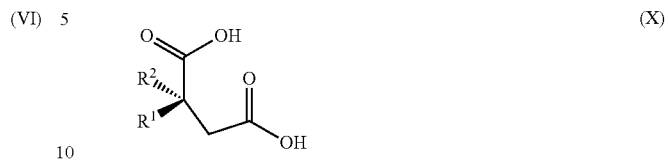
(X)

wherein $R^1$ and $R^2$ are as defined for the compound of formula I; and
(c-vi-2) reacting the compound of formula X with a compound of formula XI $$H_2N\text{-}A'$$ (XI)

wherein A' is optionally substituted aryl or optionally substituted heteroaryl to give a compound of formula XII

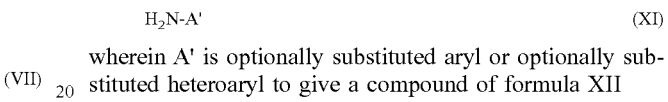
(XII)

wherein $R^1$ and $R^2$ are as defined for the compound of formula I and A' is as defined for the compound of formula XI; or
(c-vii-1) reducing the compound of formula I with a suitable reducing agent to give a compound of formula IV

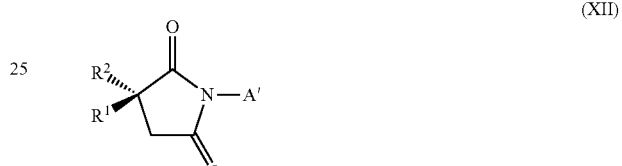
(IV)

wherein P, $R^1$ and $R^2$ are as defined for the compound of formula I; and
(c-vii-2) reacting the compound of formula IV with a compound of formula XIII $$X^B\text{-}A'$$ (XIII)

wherein A' is as defined for the compound of formula XII and $X^B$ is a leaving group, e.g. halogen such as bromo, to give a compound of formula XIV

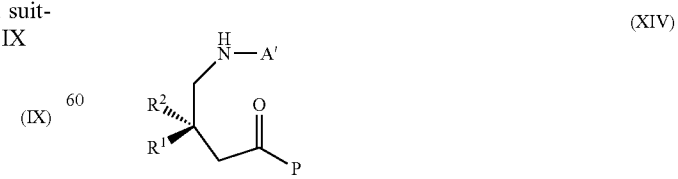
(XIV)

wherein P, $R^1$ and $R^2$ are as defined for the compound of formula I and A' is as defined for the compound of formula XII; and (c-vii-3) reducing the compound of formula XIV with a suitable reducing agent to give a compound of formula XV

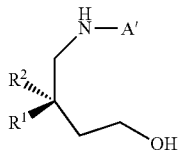
(XV)

wherein $R^1$ and $R^2$ are as defined for the compound of formula I and A' is as defined for the compound of formula XII; and (c-vii-4) treating the compound of formula XV with a suitable activating agent to give a compound of formula XVI

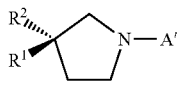
(XVI)

wherein $R^1$ and $R^2$ are as defined for the compound of formula I and A' is as defined for the compound of formula XII; or (c-viii-1) preparing a compound of formula XIV as described in a-vii-2;

(c-viii-2) cyclising the compound of formula XIV, e.g. by heating, to give a compound of formula XVII

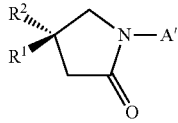
(XVII)

wherein $R^1$ and $R^2$ are as defined for the compound of formula I and A' is as defined for the compound of formula XII.

In a further aspect the invention provides a process for the enantio-selective preparation of a pyrrolidine derivative comprising (d-i) reacting a compound of formula II

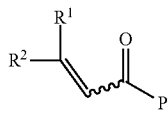
(I)

wherein

P is hydroxy, alkoxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, $R^1$ is chlorodifluoromethyl or trifluoromethyl;

$R^2$ is aryl or heteroaryl, each optionally substituted;

with a nitromethane in the presence a chiral catalyst to give a compound of formula XX.

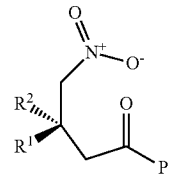
(XX)

wherein P, $R^1$ and $R^2$ are as defined for the compound of formula I; and (d-ii-1) reducing the compound of formula XX with a suitable reducing agent to give a compound of formula IV

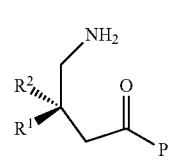
(IV)

wherein P, $R^1$ and $R^2$ are as defined for the compound of formula I; and (d-ii-2) cyclising the compound of formula IV, e.g. by heating, to give a compound of formula III

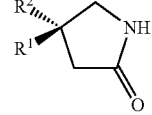
(III)

wherein $R^1$ and $R^2$ are as defined for the compound of formula I; or (d-iii-1) reducing the compound of formula XX with a suitable reducing agent to give a compound of formula VIII

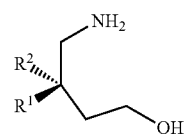
(VIII)

wherein $R^1$ and $R^2$ are as defined for the compound of formula I; and (d-iii-2) treating the compound of formula VIII with an activating agent to give a compound of formula IX

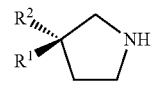
(IX)

wherein $R^1$ and $R^2$ are as defined for the compound of formula I.

In a further aspect the invention provides a process for the enantio-selective preparation of a pyrrolidine derivative comprising
(e-i) reacting a compound of formula XXI

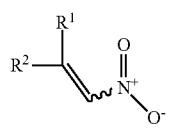
(XXI)

wherein
R¹ is chlorodifluoromethyl or trifluoromethyl;
R² is aryl or heteroaryl, each optionally substituted;
with a compound of formula XXII

(XXII)

P is hydroxy, alkoxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom; and
(e-ii-1) reducing the compound of formula XX with a suitable reducing agent to give a compound of formula IV

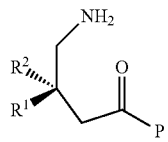
(IV)

wherein P, R¹ and R² are as defined for the compound of formula I; and
(e-ii-2) cyclising the compound of formula IV, e.g. by heating, to give a compound of formula III

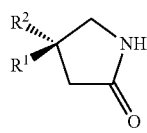
(III)

wherein R¹ and R² are as defined for the compound of formula I; or
(e-iii-1) reducing the compound of formula XX with a suitable reducing agent to give a compound of formula VIII

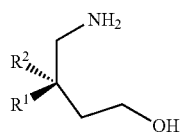
(VIII)

wherein R¹ and R² are as defined for the compound of formula I; and
(e-iii-2) treating the compound of formula VIII with an activating agent, such as SOCl₂ to give a compound of formula IX

(IX)

wherein R¹ and R² are as defined for the compound of formula I.

In a further aspect the invention provides a process for the enantio-selective preparation of a pyrrolidine derivative comprising
(f-i) reacting a compound of formula XXI

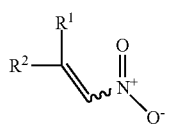
(XXI)

wherein
R¹ is chlorodifluoromethyl or trifluoromethyl;
R² is aryl or heteroaryl, each optionally substituted;
with a compound of formula XXIII

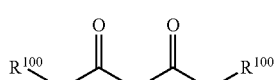
(XXIII)

wherein R¹⁰⁰ is alkyl, aryl or heteroaryl, each optionally substituted;
in the presence of a chiral catalyst to give a compound of formula XXIV

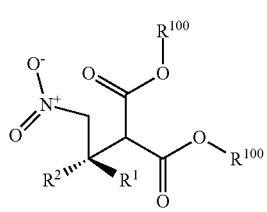
(XXIV)

wherein R¹, R² are as defined for the compound of formula XXI and R¹⁰⁰ is as defined for the compound of formula XXIII; and
(f-ii) reductively cyclising the compound of formula XXIV with a suitable reducing agent to give a compound of formula XXV

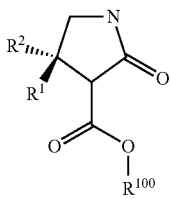

(XXV)

wherein $R^1$, $R^2$ are as defined for the compound of formula XXI and $R^{100}$ is as defined for the compound of formula XXIII; and (f-iii) treating the compound of formula XXV with base followed by treatment with acid to give a compound of formula III

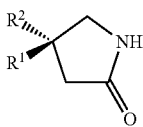

(III)

wherein $R^1$ and $R^2$ are as defined for the compound of formula XXI.

The processes of the invention may also comprise one or more of the following:

reducing a compound of formula III to a compound of formula IX with a suitable reducing agent;

reducing a compound of formula IV to a compound of formula III with a suitable reducing agent;

reducing a compound of formula IV to a compound of formula IX with a suitable reducing agent;

reducing a compound of formula XII to a compound of formula XVII with a suitable reducing agent;

reducing a compound of formula XII to a compound of formula XVI with a suitable reducing agent;

reducing a compound of formula XVII to a compound of formula XVI with a suitable reducing agent.

Suitable reducing agents for the above processes will be apparent to the person skilled in the art, and are examples are described in more detail below.

In a further aspect the invention provides a compound of formula IIc

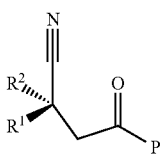

(IIc)

wherein

P is alkyl, hydroxy, alkoxy, aryloxy, alkylsulfinyl, or arylsulfinyl, each optionally substituted;

$R^1$ is chlorodifluoromethyl or trifluoromethyl;

$R^2$ is aryl or heteroaryl, each optionally substituted.

Preferred substituent definitions are given below.

In a further aspect the invention provides a compound of formula III

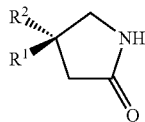

(III)

wherein $R^1$ is chlorodifluoromethyl or trifluoromethyl;

$R^2$ is aryl or heteroaryl, each optionally substituted.

Preferred substituent definitions are given below.

In a further aspect the invention provides a compound of formula IV

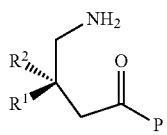

(IV)

wherein

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, $R^1$ is chlorodifluoromethyl or trifluoromethyl;

$R^2$ is aryl or heteroaryl, each optionally substituted.

Preferred substituent definitions are given below.

In a further aspect the invention provides a compound of formula V

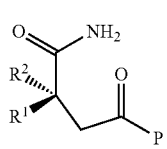

(V)

wherein

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, $R^1$ is chlorodifluoromethyl or trifluoromethyl;

$R^2$ is aryl or heteroaryl, each optionally substituted.

Preferred substituent definitions are given below.

In a further aspect the invention provides a compound of formula VI

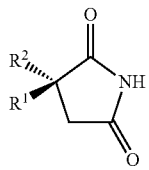

(VI)

wherein
R¹ is chlorodifluoromethyl or trifluoromethyl;
R² is aryl or heteroaryl, each optionally substituted.
Preferred substituent definitions are given below.
In a further aspect the invention provides a compound of formula VII

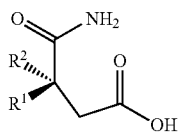
(VII)

wherein
R¹ is chlorodifluoromethyl or trifluoromethyl;
R² is aryl or heteroaryl, each optionally substituted.
Preferred substituent definitions are given below.
In a further aspect the invention provides a compound of formula VIII

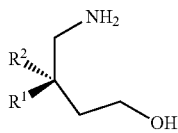
(VIII)

wherein
R¹ is chlorodifluoromethyl or trifluoromethyl;
R² is aryl or heteroaryl, each optionally substituted.
Preferred substituent definitions are given below.
In a further aspect the invention provides a compound of formula IX

(IX)

wherein
R¹ is chlorodifluoromethyl or trifluoromethyl;
R² is aryl or heteroaryl, each optionally substituted.
Preferred substituent definitions are given below.
In a further aspect the invention provides a compound of formula X

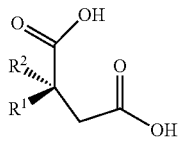
(X)

wherein
R¹ is chlorodifluoromethyl or trifluoromethyl;
R² is aryl or heteroaryl, each optionally substituted.
Preferred substituent definitions are given below.

In a further aspect the invention provides a compound of formula XII

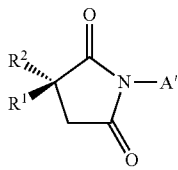
(XII)

wherein
R¹ is chlorodifluoromethyl or trifluoromethyl;
R² is aryl or heteroaryl, each optionally substituted;
A' is optionally substituted aryl or optionally substituted heteroaryl.
Preferred substituent definitions are given below.
In a further aspect the invention provides a compound of formula XIV

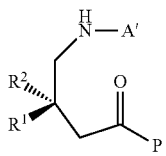
(XIV)

wherein
P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom,
R¹ is chlorodifluoromethyl or trifluoromethyl;
R² is aryl or heteroaryl, each optionally substituted;
A' is optionally substituted aryl or optionally substituted heteroaryl.
Preferred substituent definitions are given below.
In a further aspect the invention provides a compound of formula XV

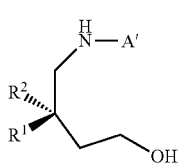
(XV)

wherein
R¹ is chlorodifluoromethyl or trifluoromethyl;
R² is aryl or heteroaryl, each optionally substituted;
A' is optionally substituted aryl or optionally substituted heteroaryl.
Preferred substituent definitions are given below.
In a further aspect the invention provides a compound of formula XVI

(XVI)

wherein
R¹ is chlorodifluoromethyl or trifluoromethyl;
R² is aryl or heteroaryl, each optionally substituted;
A' is optionally substituted aryl or optionally substituted heteroaryl.
Preferred substituent definitions are given below.
In a further aspect the invention provides a compound of formula XVII

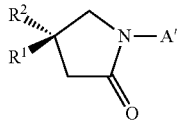
(XVII)

wherein
R¹ is chlorodifluoromethyl or trifluoromethyl;
R² is aryl or heteroaryl, each optionally substituted;
A' is optionally substituted aryl or optionally substituted heteroaryl.
Preferred substituent definitions are given below.
In a further aspect the invention provides a compound of formula XVIII

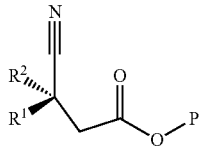
(XVIII)

wherein
P is alkyl, aryl or heteroaryl, each optionally substituted, wherein the heteroaryl is connected at P via a ring carbon atom;
R¹ is chlorodifluoromethyl or trifluoromethyl;
R² is aryl or heteroaryl, each optionally substituted.
Preferred substituent definitions are given below.
In a further aspect the invention provides a mixture comprising a compound of IIc and a compound of formula IIIA

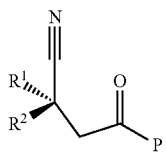
(IIcA)

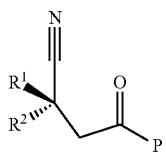
(IIc)

wherein
P is alkyl, hydroxy, alkoxy, aryloxy, alkylsulfinyl, or arylsulfinyl, each optionally substituted;
R¹ is chlorodifluoromethyl or trifluoromethyl;
R² is aryl or heteroaryl, each optionally substituted;
wherein the mixture is enriched for the compound of formula IIc.
Preferred substituent definitions are given below.

In a further aspect the invention provides a mixture comprising a compound of formula III and a compound of formula IIIA

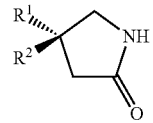
(IIIA)

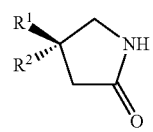
(III)

wherein
R¹ is chlorodifluoromethyl or trifluoromethyl;
R² is aryl or heteroaryl, each optionally substituted;
wherein the mixture is enriched for the compound of formula III.
Preferred substituent definitions are given below.
In a further aspect the invention provides a mixture comprising a compound of formula IV and a compound of formula WA

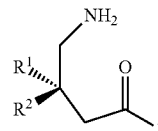
(IVA)

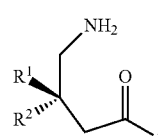
(IV)

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom,
R¹ is chlorodifluoromethyl or trifluoromethyl;
R² is aryl or heteroaryl, each optionally substituted.
Preferred substituent definitions are given below.
In a further aspect the invention provides a mixture comprising a compound of formula V and a compound of formula VA

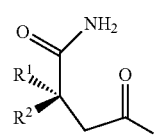
(VA)

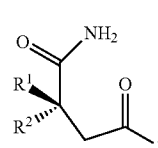
(V)

wherein

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, $R^1$ is chlorodifluoromethyl or trifluoromethyl;

$R^2$ is aryl or heteroaryl, each optionally substituted wherein the mixture is enriched for the compound of formula V.

Preferred substituent definitions are given below.

In a further aspect the invention provides a mixture comprising a compound of formula VI and a compound of formula VIA

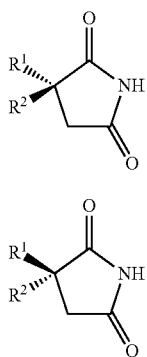

(VIA)

(VI)

wherein $R^1$ is chlorodifluoromethyl or trifluoromethyl;

$R^2$ is aryl or heteroaryl, each optionally substituted;

wherein the mixture is enriched for the compound of formula VI.

In a further aspect the invention provides a mixture comprising a compound of formula VII and a compound of formula VIIA

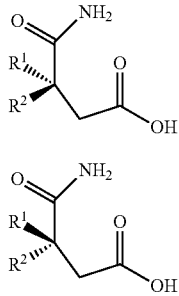

(VIIA)

(VII)

wherein $R^1$ is chlorodifluoromethyl or trifluoromethyl;

$R^2$ is aryl or heteroaryl, each optionally substituted;

wherein the mixture is enriched for the compound of formula VII.

Preferred substituent definitions are given below.

In a further aspect the invention provides a mixture comprising a compound of formula VIII and a compound of formula VIIIA

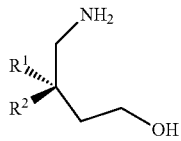

(VIIIA)

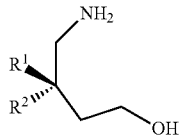

(VIII)

wherein $R^1$ is chlorodifluoromethyl or trifluoromethyl;

$R^2$ is aryl or heteroaryl, each optionally substituted;

wherein the mixture is enriched for the compound of formula VIII.

Preferred substituent definitions are given below.

In a further aspect the invention provides a mixture comprising a compound of formula IX and a compound of formula IXA

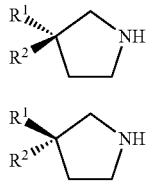

(IXA)

(IX)

wherein $R^1$ is chlorodifluoromethyl or trifluoromethyl;

$R^2$ is aryl or heteroaryl, each optionally substituted;

wherein the mixture is enriched for the compound of formula IX.

Preferred substituent definitions are given below.

In a further aspect the invention provides a mixture comprising a compound of formula X and a compound of formula XA

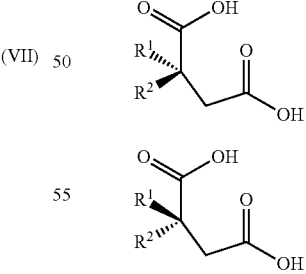

(XA)

(X)

$R^1$ is chlorodifluoromethyl or trifluoromethyl;

$R^2$ is aryl or heteroaryl, each optionally substituted;

wherein the mixture is enriched for the compound of formula X.

Preferred substituent definitions are given below.

In a further aspect the invention provides a mixture comprising a compound of formula XII and a compound of formula XIIA

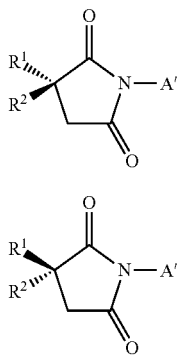

(XIIA)

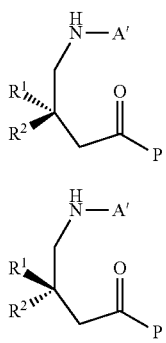

(XII)

wherein
R¹ is chlorodifluoromethyl or trifluoromethyl;
R² is aryl or heteroaryl, each optionally substituted;
A' is optionally substituted aryl or optionally substituted heteroaryl; wherein the mixture is enriched for the compound of formula XII.
Preferred substituent definitions are given below.
In a further aspect the invention provides a mixture comprising a compound of formula XIV and a compound of formula XIVA (XIVA)

(XIV)

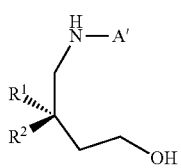

wherein
P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom,
R¹ is chlorodifluoromethyl or trifluoromethyl;
R² is aryl or heteroaryl, each optionally substituted;
A' is optionally substituted aryl or optionally substituted heteroaryl;
wherein the mixture is enriched for the compound of formula XIV.
Preferred substituent definitions are given below.
In a further aspect the invention provides a mixture comprising a compound of formula XV and a compound of formula XVA (XVA)

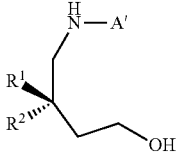

(XV)

wherein
R¹ is chlorodifluoromethyl or trifluoromethyl;
R² is aryl or heteroaryl, each optionally substituted;
A' is optionally substituted aryl or optionally substituted heteroaryl;
wherein the mixture is enriched for the compound of formula XV.
Preferred substituent definitions are given below.
In a further aspect the invention provides a mixture comprising a compound of formula XVI and a compound of formula XVIA (XVIA)

(XVI)

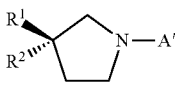

wherein
R¹ is chlorodifluoromethyl or trifluoromethyl;
R² is aryl or heteroaryl, each optionally substituted;
A' is optionally substituted aryl or optionally substituted heteroaryl;
wherein the mixture is enriched for the compound of formula XVI.
Preferred substituent definitions are given below.
In a further aspect the invention provides a mixture comprising a compound of formula XVII and a compound of formula XVIIA (XVIIA)

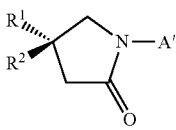

(XVII)

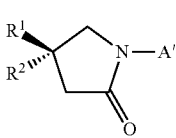

R¹ is chlorodifluoromethyl or trifluoromethyl;
R² is aryl or heteroaryl, each optionally substituted;
A' is optionally substituted aryl or optionally substituted heteroaryl;
wherein the mixture is enriched for the compound of formula XVII.
Preferred substituent definitions are given below.
In a further aspect the invention provides a mixture comprising a compound of formula XVIII and a compound of formula XVIIIA

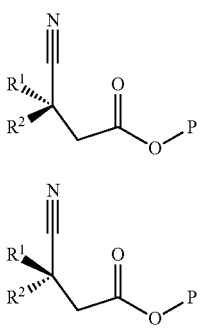

(XVIIIA)

(XVIII)

wherein
P is alkyl, aryl or heteroaryl, each optionally substituted, wherein the heteroaryl is connected at P via a ring carbon atom;
$R^1$ is chlorodifluoromethyl or trifluoromethyl;
$R^2$ is aryl or heteroaryl, each optionally substituted;
wherein the mixture is enriched for the compound of formula XVIII.
Preferred substituent definitions are given below.
In a further aspect the invention provides a compound of formula XXIX.
In a further aspect the invention provides a compound of formula XXX.
In a further aspect the invention provides a compound of formula XXXI.
In a further aspect the invention provides a compound of formula XXXII.
In a further aspect the invention provides a compound of formula XXXIII.

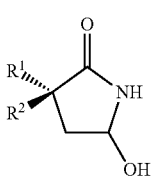

(XXIX)

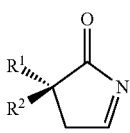

(XXX)

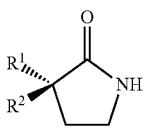

(XXXI)

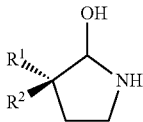

(XXXII)

(XXXIII)

In the above compounds $R^1$ and $R^2$ are as defined for the compound of formula IIa.

In a further aspect the invention provides a mixture comprising a compound of formula XXIX and a compound of formula XXIXA, wherein the mixture is enriched for the compound of formula XXIX.
In a further aspect the invention provides a compound of formula XXX and a compound of formula XXXA wherein the mixture is enriched for the compound of formula XXX.
In a further aspect the invention provides a compound of formula XXXI and a compound of formula XXXIA wherein the mixture is enriched for the compound of formula XXXI.
In a further aspect the invention provides a compound of formula XXXII and a compound of formula XXXIIA wherein the mixture is enriched for the compound of formula XXXII.
In a further aspect the invention provides a compound of formula XXXIII and a compound of formula XXXIIA wherein the mixture is enriched for the compound of formula XXXII.
The compound of formula XXIXA, XXXA, XXXIA, XXXIIA and XXXIIIA have the opposite stereochemistry to XXIX, XXX, XXXI, XXXII and XXXIII at the carbon bonded to $R^1$ and $R^2$.
In a further aspect the invention provides a process for preparing pyrrolidine derivatives comprising
(a-i) reacting a compound of formula Ia

(Ia)

wherein
P is alkyl, aryl or heteroaryl, each optionally substituted, wherein the heteroaryl is connected at P via a ring carbon atom;
$R^1$ is chlorodifluoromethyl or trifluoromethyl;
$R^2$ is aryl or heteroaryl, each optionally substituted;
with a source of cyanide to give a compound of formula IIa

(IIa-1)

wherein P, $R^1$ and $R^2$ are as defined for the compound of formula Ia; and
(a-ii) oxidising the compound of formula IIa with a peroxide in the presence of strong acid to give a compound of formula VI-1

(VI-1)

wherein $R^1$ and $R^2$ are as defined for the compound of formula Ia.

The cyanide addition can be done in presence of a base and/or a catalyst. Examples of bases include triethyl amine, sodium carbonate, potassium carbonate, sodium hydroxide, potassium hydroxide.

Examples of chiral catalysts include crown ethers and phase transfer catalysts such as tetrabutylammonium bromide.

In addition, the reaction optionally comprises (a-iii-1) reducing the compound of formula VI-1 with a suitable reducing agent to give a compound of formula IX-1

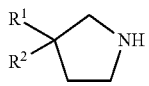

(IX-1)

wherein $R^1$ and $R^2$ are as defined for the compound of formula Ia.

and optionally (a-iv-1) reacting the compound of formula IX with a compound of formula (XIII)

$$X^B\text{-}A'$$ (XIII)

wherein $X^B$ is a leaving group such as halogen, and A' is optionally substituted aryl or optionally substituted heteroaryl to give a compound of formula XVI-1

(XVI-1)

wherein $R^1$ and $R^2$ are as defined for the compound of formula Ia and A' is as defined for the compound of formula XIII;

or the reaction optionally comprises (a-iii-2) reacting the compound of formula VI-1 with a compound of formula XIII-1 to give a compound of formula XII-1

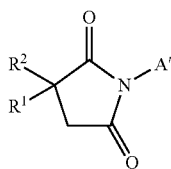

(XII-1)

wherein $R^1$ and $R^2$ are as defined for the compound of formula Ia and A' is as defined for the compound of formula XIII;

and optionally (a-iv-2) reducing the compound of formula XII-1 with a suitable reducing agent to give a compound of formula XVI-1.

In a further aspect the invention provides a compound of formula VI-1.

In a further aspect the invention provides a compound of formula XXIX-1.

In a further aspect the invention provides a compound of formula XXX-1.

In a further aspect the invention provides a compound of formula XXXI-1.

In a further aspect the invention provides a compound of formula XXXII-1.

In a further aspect the invention provides a compound of formula XXXIII-1.

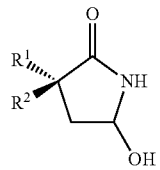

(XXIX-1)

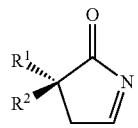

(XXX-1)

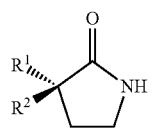

(XXXI-1)

(XXXII-1)

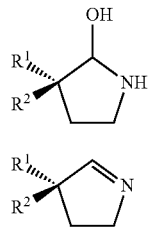

(XXXIII-1)

In the compounds above $R^1$ and $R^2$ are as defined for the compound of formula Ia.

In enantiomerically enriched mixtures of the invention, the molar proportion of the enriched compound in the mixture compared to the total amount of both enantiomers is for example greater than 50%, e.g. at least 55, 60, 65, 70, 75, 80, 85, 90, 95, 96, 97, 98, or at least 99%.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are, unless indicated to the contrary, preferably $C_1$-$C_6$, more preferably $C_1$-$C_4$, most preferably $C_1$-$C_3$ alkyl groups.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are, unless indicated to the contrary, preferably $C_1$-$C_6$, more preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are, unless indicated to the contrary, preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are, unless indicated to the contrary, preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl-, haloalkylsulfonyl-, haloalkylcarbonyl- or haloalkoxycarbonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups can be in mono- or bi-cyclic form and are, for example, cyclopropyl, cyclobutyl, cyclohexyl and bicyclo[2.2.1]heptan-2-yl. The cycloalkyl groups are, unless indicated to the contrary, preferably $C_3$-$C_8$, more preferably $C_3$-$C_6$ cycloalkyl groups.

Aryl groups are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is, unless indicated to the contrary, preferably substituted by one to four substituents, most preferably by one to three substituents.

Heteroaryl groups are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl, benzothiazolyl and benzotriazolyl. Monocyclic heteroaryl groups are preferred, pyridyl being most preferred. Where a heteroaryl moiety is said to be substituted, the heteroaryl moiety is, unless indicated to the contrary, preferably substituted by one to four substituents, most preferably by one to three substituents.

Heterocyclyl groups are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is, unless indicated to the contrary, preferably substituted by one to four substituents, most preferably by one to three substituents.

Unless stated otherwise where groups are optionally substituted they may be substituted e.g. by one to five groups, e.g. by one to three groups, preferably independently selected from nitro, cyano, hydroxy, halogen, mercapto, isocyano, cyanate, isothiocyanate, carboxy, carbamoyl, aminosulfonyl, monoalkylamino, dialkylamino, N-alkylcarbonylamino, alkyl, alkenyl, alkynyl, cycloalkyl, cycloalkenyl, $SF_5$, alkoxy, alkenyloxy, alkynyloxy, cycloalkyloxy, cycloalkenyloxy, alkoxy-carbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfenyl, alkylsulfinyl including isomers, alkylsulfonyl, monoalkylaminosulfonyl, dialkylaminosulfonyl, alkylphosphinyl, alkylphosphonyl, alkylphosphinyl including isomers, alkylphosphonyl including isomers, N-alkyl-aminocarbonyl, -dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, arylamino, benzylamino, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl or haloalkoxyalkyl, cycloalkylamino-carbonyl, alkylsulfinylimino, alkylsulfonylimino, alkoxyimino, and a heterocyclic group;

preferably nitro, cyano, hydroxy, mercapto, isocyano, cyanate, isothiocyanate, carboxy, carbamoyl, aminosulfonyl, mono-$C_1$-$C_{12}$alkylamino, di-$C_2$-$C_{24}$alkylamino, N—$C_1$-$C_{12}$alkylcarbonylamino, $C_1$-$C_{12}$alkyl, $C_2$-$C_6$alkenyl, $C_2$-$C_6$alkynyl, $C_3$-$C_8$cycloalkyl, $C_3$-$C_8$cycloalkenyl, $SF_5$, $C_1$-$C_{12}$alkoxy, $C_2$-$C_6$alkenyloxy, $C_2$-$C_6$alkynyloxy, $C_3$-$C_8$cycloalkyloxy, $C_3$-$C_8$cycloalkenyloxy, $C_1$-$C_{12}$alkoxycarbonyl, $C_2$-$C_6$alkenyloxycarbonyl, $C_2$-$C_6$alkynyloxycarbonyl, aryloxycarbonyl, $C_1$-$C_{12}$alkylcarbonyl, $C_2$-$C_6$alkenylcarbonyl, $C_2$-$C_6$alkynylcarbonyl, arylcarbonyl, $C_1$-$C_{12}$alkylthio, $C_3$-$C_8$cycloalkylthio, $C_2$-$C_6$alkenylthio, $C_3$-$C_8$cycloalkenylthio, $C_2$-$C_6$alkynylthio, $C_1$-$C_{12}$alkylsulfenyl, $C_1$-$C_{12}$alkylsulfinyl including isomers, $C_1$-$C_{12}$alkylsulfonyl, mono-$C_1$-$C_{12}$alkylaminosulfonyl, di-$C_2$-$C_{24}$alkylaminosulfonyl, $C_1$-$C_{12}$alkylphosphinyl, $C_1$-$C_{12}$alkylphosphonyl, $C_1$-$C_{12}$alkylphosphinyl including isomers, $C_1$-$C_{12}$alkylphosphonyl including isomers, N—$C_1$-$C_{12}$alkyl-aminocarbonyl, -di-$C_2$-$C_{24}$alkyl-aminocarbonyl, N—$C_1$-$C_{12}$alkylcarbonyl-aminocarbonyl, N—$C_1$-$C_{12}$alkylcarbonyl-N—$C_1$-$C_{12}$alkylaminocarbonyl, aryl, aryloxy, benzyl, benzyloxy, benzylthio, arylthio, arylamino, benzylamino, trialkylsilyl, $C_1$-$C_{12}$alkoxyalkyl, $C_1$-$C_{12}$alkylthioalkyl, $C_1$-$C_{12}$alkylthioalkoxy, $C_1$-$C_{12}$alkoxyalkoxy, phenethyl, benzyloxy, $C_1$-$C_{12}$haloalkyl, $C_1$-$C_{12}$haloalkoxy, $C_1$-$C_{12}$haloalkylthio, $C_1$-$C_{12}$haloalkylcarbonyl, $C_1$-$C_{12}$haloalkoxycarbonyl, $C_1$-$C_{12}$haloalkoxyalkoxy, $C_1$-$C_{12}$haloalkoxy$C_1$-$C_{12}$alkylthio, $C_1$-$C_{12}$haloalkoxy$C_1$-$C_{12}$alkylcarbonyl or $C_1$-$C_{12}$haloalkoxy-$C_1$-$C_{12}$alkyl, $C_3$-$C_8$cycloalkylamino-carbonyl, $C_1$-$C_{12}$alkylsulfinylimino, $C_1$-$C_{12}$alkylsulfonylimino, $C_1$-$C_{12}$alkoxyimino, and a heterocyclic group, wherein aryl is phenyl and heterocyclic groups are heteroaryl groups as defined above. Preferred optional substituents are cyano, halogen, $C_1$-$C_4$alkyl, $C_1$-$C_4$haloalkyl, $C_1$-$C_4$alkoxy, and $C_1$-$C_4$haloalkoxy.

Bearing in mind the stereocentre which is the subject of the invention, the invention otherwise includes all isomers of compounds of formula I, salts and N-oxides thereof, including enantiomers, diastereomers and tautomers. Tautomers of the compounds of formula I include the enamine form, for example. These are covered by the invention.

Preferred substituent values in compounds of formula I are as follows, which may be combined in any order. These preferred substituent values also apply to other compounds of the invention in which the same substituents are present.

Preferably $R^1$ is trifluoromethyl.

Preferably R² is aryl or aryl substituted by one to five Q¹, or heteroaryl or heteroaryl substituted by one to five Q¹. Preferably R² is group A

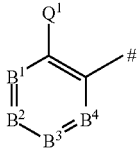
(A)

wherein B¹, B², B³, B⁴ and Q¹ are as defined below. More preferably R² is group A1 or A2

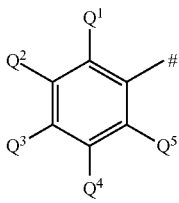
(A1)

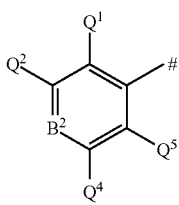
(A2)

More preferably R² is group A3 or A4

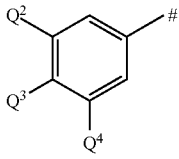
(A3)

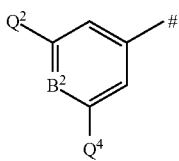
(A4)

B¹, B², B³, B⁴ are independently C-Q¹ or nitrogen.

Q¹, Q², Q³, Q⁴, and Q⁵ are independently hydrogen, halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkylamino, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, optionally substituted aryl or optionally substituted heterocyclyl. Preferably, Q¹, Q², Q³, Q⁴, and Q⁵ are each independently hydrogen, halogen, cyano, $C_1$-$C_8$alkyl, $C_1$-$C_8$haloalkyl, $C_1$-$C_8$alkoxy or $C_1$-$C_8$haloalkoxy, more preferably bromo, chloro, fluoro, cyano, methyl, trifluoromethyl, methoxy or trifluoromethoxy, preferably bromo, chloro or trifluoromethyl. Preferably at least two of Q¹, Q², Q³, Q⁴, and Q⁵ are not hydrogen.

When P is defined as hydroxy, alkoxy, aryloxy, alkylsulfinyl, arylsulfinyl or heteroaryl, each optionally substituted, and wherein the heteroaryl contains at least one ring nitrogen atom, and the heteroaryl is connected at P via a ring nitrogen atom, then P is preferably hydroxy, $C_1$-$C_{12}$alkoxy, $C_1$-$C_{12}$haloalkoxy phenyloxy, $C_1$-$C_{12}$sulfinyl, phenylsulfinyl or heteroaryl, wherein phenyl (including phenyloxy) and heteroaryl are optionally substituted by one to five groups independently selected from cyano, halogen, $C_1$-$C_4$alkyl, $C_1$-$C_4$haloalkyl, $C_1$-$C_4$alkoxy, and $C_1$-$C_4$haloalkoxy, and heteroaryl is pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl, quinolinyl, cinnolinyl, quinoxalinyl, indolyl, indazolyl, benzimidazolyl, benzothiophenyl, benzothiazolyl or benzotriazolyl, more preferably P is hydroxyl, $C_1$-$C_6$alkoxy, N-pyrrolyl, N-imidazolyl, N-1,2-4-triazolyl, N-benzotriazolyl, or $C_1$-$C_6$alkylsulfinyl.

When P is defined as alkyl, aryl or heteroaryl, each optionally substituted (and e.g. wherein the heteroaryl is connected to at P via a ring carbon atom), then preferably P is $C_1$-$C_{12}$alkyl, $C_1$-$C_{12}$haloalkyl, phenyl or heteroaryl, and heteroaryl is pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl, quinolinyl, cinnolinyl, quinoxalinyl, indolyl, indazolyl, benzimidazolyl, benzothiophenyl, benzothiazolyl or benzotriazolyl, e.g. wherein phenyl and heteroaryl are each optionally substituted by one to five groups independently selected from cyano, halogen, $C_1$-$C_4$alkyl, $C_1$-$C_4$haloalkyl, $C_1$-$C_4$alkoxy and $C_1$-$C_4$haloalkoxy.

When P is defined as optionally substituted heteroaryl, and wherein the heteroaryl contains at least one ring nitrogen or oxygen atom, wherein the heteroaryl is connected at P via a ring carbon atom, then preferably P is pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl, quinolinyl, cinnolinyl, quinoxalinyl, indolyl, indazolyl, benzimidazolyl, benzothiophenyl, benzothiazolyl or benzotriazolyl, each optionally substituted by one to five groups independently selected from cyano, halogen, $C_1$-$C_4$alkyl, $C_1$-$C_4$haloalkyl, $C_1$-$C_4$alkoxy, and $C_1$-$C_4$haloalkoxy.

When P is defined as P is alkyl, hydroxy, alkoxy, aryloxy, alkylsulfinyl, or arylsulfinyl, each optionally substituted, then preferably P is $C_1$-$C_{12}$alkyl, $C_1$-$C_{12}$haloalkyl, hydroxy, $C_1$-$C_{12}$alkoxy, $C_1$-$C_{12}$haloalkoxy, phenyloxy, $C_1$-$C_{12}$sulfinyl, phenylsulfinyl, wherein phenyl is optionally substituted by one to five groups independently selected from cyano, halogen, $C_1$-$C_4$alkyl, $C_1$-$C_4$haloalkyl, $C_1$-$C_4$alkoxy, and $C_1$-$C_4$haloalkoxy.

Preferably A' is selected from P1 to P6

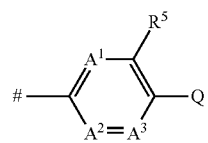
(P1)

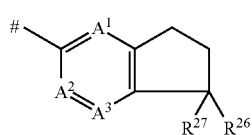 (P2)
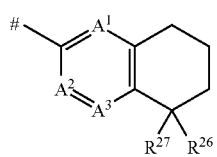 (P3)
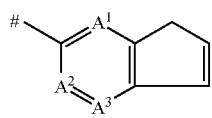 (P4)
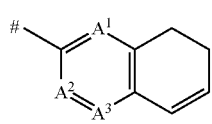 (P5)
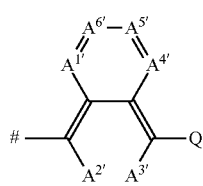 P6
In one group of compounds A' is P1. In another group of compounds A' is P2. In another group of compounds A' is P3. In another group of compounds A' is P4. In another group of compounds A' is P5. In another group of compounds A' is P6. In another group of compounds A' is selected from P3 to P5. When P is P2 to P5, P is preferably P7 to P22
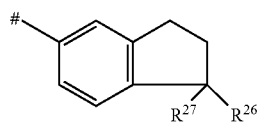 P7
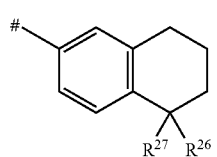 P8
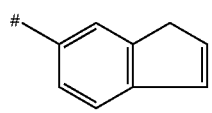 P9
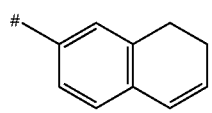 P10
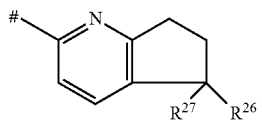 P11
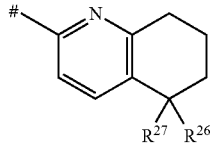 P12
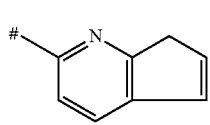 P13
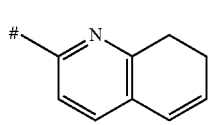 P14
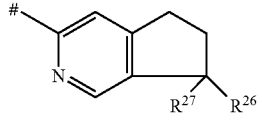 P15
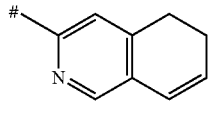 P16
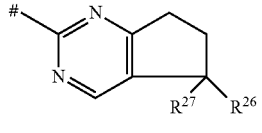 P17
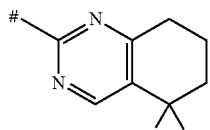 P18
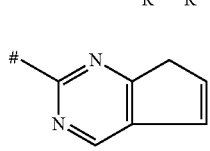 P19
P20
P21

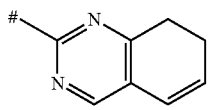

P22

A$^1$, A$^2$ and A$^3$ are independently of each other C—H, C—R$^5$, or nitrogen. Preferably no more than two of A$^1$, A$^2$ and A$^3$ are nitrogen. In one group of compounds A$^1$, A$^2$ and A$^3$ are each C—R$^5$. In one group of compounds A$^1$ is nitrogen and A$^2$ and A$^3$ are both C—R$^5$. In another group of compounds A$^2$ is nitrogen and A$^1$ and A$^3$ are both C—R$^5$. In another group of compounds A$^1$ and A$^2$ are both nitrogen and A$^3$ is C—R$^5$. In one group of compounds A$^1$, A$^2$ and A$^3$ are each C—H. In one group of compounds A$^1$ is nitrogen and A$^2$ and A$^3$ are both C—H. In another group of compounds A$^2$ is nitrogen and A$^1$ and A$^3$ are both C—H. In another group of compounds A$^1$ and A$^2$ are both nitrogen and A$^3$ is C—H. Preferably A$^1$, A$^2$ and A$^3$ are each C—H.

A$^{1'}$, A$^{2'}$, A$^{3'}$, A$^{4'}$, A$^{5'}$ and A$^{6'}$ are independently of each other C—H, C—R$^5$ or nitrogen provided that no more than two of A$^{1'}$, A$^{2'}$, A$^{3'}$, A$^{4'}$, A$^{5'}$ and A$^{6'}$ are nitrogen. Preferably A$^{1'}$, A$^{2'}$, A$^{3'}$, A$^{4'}$, A$^{5'}$ and A$^{6'}$ are C—H.

The ring formed by A$^1$, A$^2$, and A$^3$, or A$^{1'}$, A$^{2'}$, A$^{3'}$, A$^{4'}$, A$^{5'}$ and A$^{6'}$ may, for example, be phenyl, pyridyl, pyrimidine, pyrazine, pyridazine, naphthyl or quinoline.

Each R$^5$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, C$_3$-C$_{10}$cycloalkyl, C$_1$-C$_8$alkoxy, C$_1$-C$_8$haloalkoxy, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl or C$_1$-C$_8$haloalkylsulfonyl. Preferably, each R$^5$ is independently halogen, C$_1$-C$_8$alkyl, C$_1$-C$_8$haloalkyl or C$_2$-C$_8$alkenyl. More preferably, each R$^5$ is independently bromo, chloro, fluoro, methyl, trifluoromethyl or vinyl, most preferably each R$^5$ is methyl.

Q is hydrogen, halogen, nitro, NH$_2$, cyano, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_3$-C$_8$haloalkynyl, C$_3$-C$_{10}$cycloalkyl, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl, C$_1$-C$_8$haloalkylsulfonyl, arylsulfonyl or arylsulfonyl substituted by one to five groups independently selected from C$_1$-C$_4$alkyl and nitro, —N(R$^6$)R$^{7b}$, —C(W$^5$)N(R$^6$)R$^7$, —C(R$^{15}$)(R$^{16}$)N(R$^{17}$)R$^{18}$, C(=W$^5$)OR$^{7a}$, —C(=W$^5$)R$^{13}$, —OR$^{14}$, aryl or aryl substituted by one to five Z$^1$, heterocyclyl or heterocyclyl substituted by one to five Z$^1$. Preferably, Q is cyano, halogen, nitro, NH$_2$, arylsulfonyl or arylsulfonyl substituted by one to five groups independently selected from C$_1$-C$_4$alkyl and nitro, heterocyclyl or heterocyclyl substituted by one to five Z$^1$, —OR$^{14}$, —C(=O)N(R$^6$)R$^7$, —CO(=O)R$^{7a}$, —C(=O)R$^{13}$, or —C(R$^{15}$)(R$^{16}$)N(R$^{17}$)R$^{18}$. More preferably, Q is cyano, halogen, nitro, NH$_2$, phenylsulfonyl or phenylsulfonyl substituted by one to five groups independently selected from C$_1$-C$_4$alkyl and nitro, —OR$^{14}$, —C(=O)N(R$^6$)R$^7$, —CO(=O)R$^{7a}$, —C(=O)R$^{13}$, —C(R$^{15}$)(R$^{16}$)N(R$^{17}$)R$^{18}$, or a heterocycle selected from H1 to H9

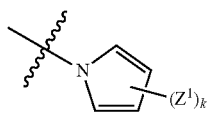

H1

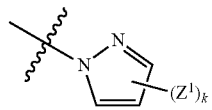

H2

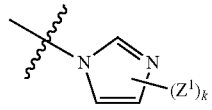

H3

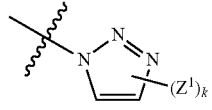

H4

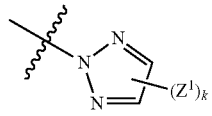

H5

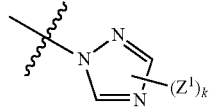

H6

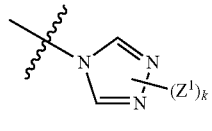

H7

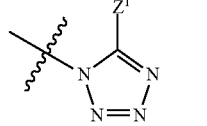

H8

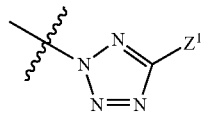

H9

Even more preferably, Q is cyano, halogen, nitro, NH$_2$, C$_1$-C$_8$alkoxy, phenylsulfonyl or phenylsulfonyl substituted by one to five groups independently selected from C$_1$-C$_4$ alkyl and nitro, —C(=O)N(R$^6$)R$^7$, —CO(=O)R$^{7a}$, —C(=O)R$^{13}$, —C(R$^{15}$)(R$^{16}$)N(R$^{17}$)R$^{18}$, or a heterocycle selected from H1 to H9.

k is 0, 1, or 2, preferably 0.

R$^6$ is hydrogen, C$_1$-C$_8$alkyl, C$_1$-C$_8$alkoxy, C$_2$-C$_8$alkenyl, C$_2$-C$_8$alkynyl, C$_3$-C$_{10}$cycloalkyl, C$_3$-C$_{10}$cycloalkyl-C$_1$-C$_4$alkylene, C$_1$-C$_8$alkylcarbonyl or C$_1$-C$_8$alkoxycarbonyl. Preferably, R$^6$ is hydrogen, C$_1$-C$_8$alkyl, C$_1$-C$_8$alkoxy, C$_1$-C$_8$alkylcarbonyl, or C$_1$-C$_8$alkoxycarbonyl. More preferably, R$^6$ is hydrogen, methyl, ethyl, methylcarbonyl or methoxycarbonyl, more preferably hydrogen, methyl or ethyl, most preferably hydrogen.

R$^7$ is hydrogen, alkyl or alkyl substituted by one to five R$^8$, alkenyl or alkenyl substituted by one to five R$^8$, alkynyl or alkynyl substituted by one to five R$^8$, C$_3$-C$_{10}$cycloalkyl or C$_3$-C$_{10}$cycloalkyl substituted by one to five R$^9$, C$_3$-C$_{10}$cycloalkyl-C$_1$-C$_4$alkylene or C$_3$-C$_{10}$cycloalkyl-C$_1$-C$_4$alkylene wherein the cycloalkyl moiety is substituted by one to five R$^9$, C$_1$-C$_8$alkyl-N(R$^6$)—C(=O)—C$_1$-C$_4$alkylene, C$_1$-C$_8$haloalkyl-N(R$^6$)—C(=O)—C$_1$-

$C_4$alkylene, $C_3$-$C_8$cycloalkyl-aminocarbonyl-$C_1$-$C_4$alkylene, $C_1$-$C_6$alkyl-O—N=CH—, $C_1$-$C_6$haloalkyl-O—N=CH—, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, aryl or aryl substituted by one to five $R^{10}$, heterocyclyl or heterocyclyl substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$. Preferably, $R^7$ is hydrogen, $C_1$-$C_5$alkyl or $C_1$-$C_5$alkyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, aryl or aryl substituted by one to five $R^{10}$, heterocyclyl or heterocyclyl substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, $C_1$-$C_8$alkyl-N($R^6$)—C(=O)—$C_1$-$C_4$ alkylene, $C_1$-$C_8$haloalkyl-N($R^6$)—C(=O)—$C_1$-$C_4$alkylene, $C_3$-$C_8$cycloalkylaminocarbonyl-$C_1$-$C_4$alkylene, $C_1$-$C_6$alkyl-O—N=CH—, or $C_1$-$C_6$haloalkyl-O—N=CH—. More preferably, $R^7$ is hydrogen, $C_1$-$C_8$alkyl, $C_1$-$C_8$haloalkyl, phenyl-$C_1$-$C_6$alkylene or phenyl-$C_1$-$C_6$alkylene wherein the phenyl moiety is substituted by one to five $R^{10}$, pyridyl-$C_1$-$C_6$alkylene or pyridyl-$C_1$-$C_6$alkylene wherein the pyridyl moiety is substituted by one to four $R^{10}$, thiazolyl-$C_1$-$C_6$alkylene or thiazolyl-$C_1$-$C_6$alkylene wherein the thiazolyl moiety is substituted by one or two $R^{10}$, phenyl or phenyl substituted by one to five $R^{10}$, pyridyl or pyridyl substituted by one to four $R^{10}$, thiazolyl or thiazolyl substituted by one or two $R^{10}$, $C_3$-$C_6$cycloalkyl or $C_3$-$C_6$cycloalkyl wherein one ring atom is replaced by O or S, $C_1$-$C_4$alkyl-O—N=CH—, $C_1$-$C_4$haloalkyl-O—N=CH—, $C_1$-$C_4$alkyl-N($R^6$)—C(=O)—$CH_2$—, $C_1$-$C_4$haloalkyl-N($R^6$)—C(=O)—$CH_2$—, or a group of formula (Y)

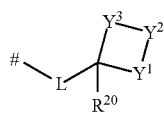

(Y)

In one group of compounds $R^7$ is not a group of formula (Y)

L is a single bond or $C_1$-$C_6$alkylene;

$Y^1$, $Y^2$ and $Y^3$ are independently of another O, $CR^{21}R^{22}$, C=O, C=N—$OR^{12}$, N—$R^{12}$, S, SO, $SO_2$, S=N—$R^{12}$ or SO=N—$R^{12}$, provided that at least one of $Y^1$, $Y^2$ or $Y^3$ is not $CR^{21}R^{22}$, C=O or C=N—$OR^{12}$. In the group of formula (Y), preferably two of $Y^1$, $Y^2$ and $Y^3$ are $CR^{21-22}$, x and the other is O, N—$R^{12}$, S, SO, $SO_2$, S=N—$R^{12}$ or SO=N—$R^{12}$, more preferably two of $Y^1$, $Y^2$ and $Y^3$ are $CH_2$ and the other is S, SO or $SO_2$. When L is a bond $Y^1$ and $Y^3$ are preferably $CH_2$ and $Y^2$ is S, SO, $SO_2$, S=N—$R^{12}$ or SO=N—$R^{12}$. When L is alkylene, $Y^1$ is preferably S, SO, $SO_2$, S=N—$R^{12}$ or SO=N—$R^{12}$ and $Y^2$ and $Y^3$ are $CH_2$.

$R^{7a}$ is hydrogen, alkyl or alkyl substituted by one to five $R^8$, alkenyl or alkenyl substituted by one to five $R^8$, alkynyl or alkynyl substituted by one to five $R^8$, cycloalkyl or cycloalkyl substituted by one to five $R^9$, aryl-alkylene or aryl-alkylene wherein the aryl moiety is substituted by one to five $R^{10}$, heteroaryl-alkylene or heteroaryl-alkylene wherein the heteroaryl moiety is substituted by one to five $R^{10}$, aryl or aryl substituted by one to five $R^{10}$, or heteroaryl or heteroaryl substituted by one to five $R^{10}$. Preferably, $R^{7a}$ is hydrogen, $C_1$-$C_{15}$alkyl or $C_1$-$C_{15}$alkyl substituted by one to five $R^8$, $C_2$-$C_{15}$alkenyl or $C_2$-$C_{15}$alkenyl substituted by one to five $R^8$, $C_2$-$C_{15}$alkynyl or $C_2$-$C_{15}$alkynyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heteroaryl-$C_1$-$C_6$alkylene or heteroaryl-$C_1$-$C_6$alkylene wherein the heteroaryl moiety is substituted by one to five $R^{10}$, or heteroaryl or heteroaryl substituted by one to five $R^{10}$. More preferably $R^{7a}$ is hydrogen, $C_1$-$C_{15}$alkyl, $C_1$-$C_{15}$haloalkyl, $C_2$-$C_{15}$alkenyl, $C_2$-$C_{15}$haloalkenyl, $C_2$-$C_{15}$alkynyl, $C_2$-$C_{15}$haloalkynyl, phenyl-$C_1$-$C_4$alkylene or phenyl-$C_1$-$C_4$alkylene wherein the phenyl moiety is substituted by one to five halogen, pyridyl-$C_1$-$C_4$alkyl or pyridyl-$C_1$-$C_4$alkyl wherein the pyridyl moiety is substituted by one to four halogen, pyridyl or pyridyl substituted by one to four $R^{10}$, most preferably $R^{7a}$ is $C_1$-$C_{15}$alkyl, $C_1$-$C_{15}$haloalkyl, $C_2$-$C_{15}$alkenyl, $C_2$-$C_{15}$haloalkenyl, pyridyl or benzyl.

$R^{7b}$ is hydrogen, alkyl, haloalkyl, alkenyl, haloalkenyl, alkynyl, haloalkynyl cycloalkyl, halocycloalkyl, alkylcarbonyl, haloalkylcarbonyl, alkoxycarbonyl, haloalkoxycarbonyl, or benzyl, more preferably $R^{7b}$ is hydrogen, $C_1$-$C_{15}$alkyl, $C_1$-$C_{15}$haloalkyl, $C_2$-$C_{15}$alkenyl, $C_2$-$C_{15}$haloalkenyl, $C_2$-$C_{15}$alkynyl, $C_2$-$C_{15}$haloalkynyl, $C_3$-$C_{10}$cycloalkyl, $C_1$-$C_{15}$alkylcarbonyl or $C_1$-$C_{15}$alkoxycarbonyl; most preferably $R^{7b}$ is $C_1$-$C_{15}$alkyl, $C_1$-$C_{15}$haloalkyl, $C_2$-$C_{15}$ alkenyl or $C_2$-$C_{15}$haloalkenyl.

Each $R^8$ is independently halogen, cyano, nitro, hydroxy, $NH_2$, mercapto, $C_1$-$C_8$alkyl, $C_1$-$C_8$haloalkyl, $C_1$-$C_8$alkoxy, $C_1$-$C_8$haloalkoxy, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylamino, $C_2$-$C_8$dialkylamino, $C_3$-$C_8$cycloalkylamino, $C_1$-$C_8$alkylcarbonyl, $C_1$-$C_8$alkoxycarbonyl, $C_1$-$C_8$alkylaminocarbonyl, $C_1$-$C_8$dialkylaminocarbonyl, $C_1$-$C_8$haloalkylcarbonyl, $C_1$-$C_8$haloalkoxycarbonyl, $C_1$-$C_8$haloalkylaminocarbonyl, $C_1$-$C_8$halodialkylaminocarbonyl. Preferably, each $R^8$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl. More preferably, each $R^8$ is independently halogen, cyano, nitro, hydroxy, $C_1$-$C_8$alkoxy, $C_1$-$C_8$haloalkoxy, mercapto, $C_1$-$C_8$alkylthio, $C_1$-$C_8$haloalkylthio, more preferably bromo, chloro, fluoro, methoxy, or methylthio, most preferably chloro, fluoro, or methoxy.

Each $R^9$ is independently halogen or $C_1$-$C_8$alkyl. Preferably, each $R^9$ is independently chloro, fluoro or methyl, most preferably each $R^9$ methyl.

Each $R^{10}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^{11}$, or heterocyclyl or heterocyclyl substituted by one to five $R^{11}$. Preferably each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Each $R^4$ and $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkoxycarbonyl; more preferably each $R^4$ and $R^{11}$ is independently bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably each $R^4$ and $R^{11}$ is independently chloro, fluoro or methyl.

Each $R^{12}$ is independently hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkylene, $C_3$-$C_8$cycloalkyl-$C_1$-$C_8$alkylene where one carbon atom in the cycloalkyl group is replaced by O, S, S(O) or $SO_2$, or $C_3$-$C_8$cycloalkyl-$C_1$-$C_8$haloalkylene, $C_1$-$C_8$hydroxyalkyl, $C_1$-$C_8$alkoxy-$C_1$-$C_8$alkylene, $C_2$-$C_8$alkenyl, $C_2$-$C_8$haloalkenyl, $C_2$-$C_8$alkynyl, $C_2$-$C_8$haloalkynyl, aryl or aryl substituted by one to three $R^{11}$, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$, or $C_1$-$C_4$alkyl-$C_1$-$C_4$alkyl-O—N=)C—$CH_2$—. Preferably, each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$. More preferably, each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, phenyl-$C_1$-$C_4$alkylene or phenyl-$C_1$-$C_4$alkylene where the phenyl moiety is substituted by one to three $R^{11}$, or pyridyl-$C_1$-$C_4$alkylene or pyridyl-$C_1$-$C_4$alkylene where the pyridyl moiety is substituted by one to three $R^{11}$.

$R^{13}$ is halogen or imidazole, preferably chloro, fluoro or bromo.

Each $R^{14}$ is independently hydrogen, $C_1$-$C_8$alkyl, $C_2$-$C_8$alkenyl, $C_2$-$C_8$alkynyl, $C_3$-$C_{10}$cycloalkyl, $C_1$-$C_6$alkyl-$C_3$-$C_8$cycloalkyl, $C_3$-$C_8$cycloalkyl-$C_1$-$C_6$alkylene, $C_1$-$C_{10}$alkylcarbonyl, $C_1$-$C_8$alkoxycarbonyl, $C_1$-$C_8$alkylsulfonyl, $C_1$-$C_8$haloalkylsulfonyl, or arylsulfonyl or arylsulfonyl substituted by one to five groups independently selected from $C_1$-$C_4$alkyl and nitro; more preferably each $R^{14}$ is independently hydrogen, $C_1$-$C_8$alkyl, phenylsulfonyl or phenylsulfonyl substituted by one to five groups independently selected from $C_1$-$C_4$alkyl and nitro.

$R^{15}$ and $R^{16}$ are each independently hydrogen, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, cyano, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, or $R^{15}$ and $R^{16}$ together with the carbon atom to which they are attached may form a 3 to 6-membered carbocyclic ring. Preferably, $R^{15}$ and $R^{16}$ are each independently hydrogen, $C_1$-$C_1$ alkyl, $C_1$-$C_{12}$haloalkyl, $C_3$-$C_8$cycloalkyl, $C_3$-$C_8$halocycloalkyl, $C_2$-$C_{12}$alkenyl or $C_2$-$C_{12}$haloalkenyl, $C_2$-$C_{12}$alkynyl, $C_2$-$C_{12}$haloalkynyl cyano, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, or $R^{15}$ and $R^{16}$ together with the carbon atom to which they are attached may form a 3 to 6-membered carbocyclic ring. Preferably, $R^{15}$ and $R^{16}$ are each independently hydrogen, halogen, cyano, $C_1$-$C_4$alkyl or $C_1$-$C_4$haloalkyl.

$R^{17}$ is hydrogen, $NH_2$, hydroxyl, $C_1$-$C_{12}$ alkoxy or $C_1$-$C_{12}$alkoxy substituted by one to five $R^8$, $C_1$-$C_{12}$alkylcarbonylamino or $C_1$-$C_{12}$alkylcarbonylamino wherein the alkyl is substituted by one to five $R^8$, $C_1$-$C_{12}$alkylamino or $C_1$-$C_{12}$alkylamino wherein the alkyl is substituted by one to five $R^8$, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, cyano, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, $C_1$-$C_{12}$alkylcarbonyl or $C_1$-$C_{12}$alkylcarbonyl substituted by one to five $R^8$, $C_1$-$C_{12}$alkoxycarbonyl or $C_1$-$C_{12}$alkoxycarbonyl substituted by one to five $R^8$ or is selected from $CH_2$—$R^{25}$, $C(=O)R^{19}$ and $C(=S)R^{19}$. Preferably, $R^{17}$ is hydrogen, $NH_2$, hydroxyl, $C_1$-$C_{12}$alkoxy, $C_1$-$C_{12}$haloalkoxy, $C_1$-$C_{12}$alkylcarbonylamino, $C_1$-$C_{12}$haloalkylcarbonylamino, $C_1$-$C_{12}$alkylamino, $C_1$-$C_{12}$haloalkylamino, $C_1$-$C_{12}$alkyl, $C_1$-$C_{12}$haloalkyl, $C_3$-$C_8$cycloalkyl, $C_3$-$C_8$halocycloalkyl, cyano, $C_1$-$C_{12}$alkenyl, $C_1$-$C_{12}$haloalkenyl, $C_2$-$C_{12}$alkynyl, $C_2$-$C_{12}$haloalkynyl, $C_1$-$C_{12}$alkylcarbonyl, $C_1$-$C_{12}$haloalkylcarbonyl, $C_1$-$C_8$alkoxycarbonyl, or $C_1$-$C_8$haloalkoxycarbonyl. More preferably, $R^{17}$ is hydrogen, $C_1$-$C_8$alkyl, $C_1$-$C_8$alkoxy, $C_1$-$C_8$alkylcarbonyl, or $C_1$-$C_8$alkoxycarbonyl.

$R^{18}$ is hydrogen, cyano, carbonyl, thiocarbonyl, $C_1$-$C_{12}$alkylcarbonyl or $C_1$-$C_{12}$ alkylcarbonyl substituted by one to five $R^8$, $C_1$-$C_{12}$alkylthiocarbonyl or $C_1$-$C_{12}$alkylthiocarbonyl substituted by one to five $R^8$, $C_1$-$C_{12}$alkylaminocarbonyl or $C_1$-$C_{12}$alkylaminocarbonyl wherein the alkyl is substituted by one to five $R^8$, $C_1$-$C_{12}$alkylaminothiocarbonyl or $C_1$-$C_{12}$alkylaminothiocarbonyl wherein the alkyl is substituted by one to five $R^8$, $C_2$-$C_{24}$ (total carbon number) dialkylaminocarbonyl or $C_2$-$C_{24}$ (total carbon number) dialkylaminocarbonyl wherein one or both alkyl is substituted by one to five $R^8$, $C_2$-$C_{24}$ (total carbon number) dialkylaminothiocarbonyl or $C_2$-$C_{24}$ (total carbon number) dialkylaminothiocarbonyl wherein one or both alkyl is substituted by one to five $R^8$, $C_1$-$C_{12}$alkoxyaminocarbonyl or $C_1$-$C_{12}$alkoxyaminocarbonyl wherein the alkoxy is substituted by one to five $R^8$, $C_1$-$C_{12}$alkoxyaminothiocarbonyl or $C_1$-$C_{12}$alkoxyaminothiocarbonyl wherein the alkoxy is substituted by one to five $R^8$, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, $C_1$-$C_{12}$thioalkoxycarbonyl or $C_1$-$C_{12}$thioalkoxycarbonyl substituted by one to five $R^8$, $C_1$-$C_{12}$thioalkoxythiocarbonyl or $C_1$-$C_{12}$thioalkoxythiocarbonyl substituted by one to five $R^8$, $C_1$-$C_{12}$alkylsulfonyl or $C_1$-$C_{12}$alkylsulfonyl substituted by one to five $R^8$, $C_3$-$C_{12}$cycloalkylcarbonyl or $C_3$-$C_{12}$cycloalkylcarbonyl substituted by one to five $R^9$, $C_2$-$C_{12}$alkenylcarbonyl or $C_2$-$C_{12}$alkenylcarbonyl substituted by one to five $R^8$, $C_2$-$C_{12}$alkynylcarbonyl or $C_2$-$C_{12}$alkynylcarbonyl substituted by one to five $R^8$, $C_3$-$C_{12}$cycloalkyl-$C_1$-$C_{12}$alkylcarbonyl or $C_3$-$C_{12}$cycloalkyl-$C_1$-$C_{12}$alkylcarbonyl substituted by one to five $R^9$, $C_1$-$C_{12}$alkylsulfenyl-$C_1$-$C_{12}$alkylcarbonyl or $C_1$-$C_{12}$alkylsulfenyl-$C_1$-$C_{12}$alkylcarbonyl substituted by one to five $R^8$, $C_1$-$C_{12}$alkylsulfinyl-$C_1$-$C_{12}$alkylcarbonyl or $C_1$-$C_{12}$alkylsulfinyl-$C_1$-$C_{12}$alkylcarbonyl substituted by one to five $R^8$, $C_1$-$C_{12}$ alkylsulfonyl-$C_1$-$C_{12}$alkylcarbonyl or $C_1$-$C_{12}$alkylsulfonyl-$C_1$-$C_{12}$alkylcarbonyl substituted by one to five $R^8$, $C_1$-$C_{12}$alkylcarbonyl-$C_1$-$C_{12}$alkylcarbonyl or $C_1$-$C_{12}$alkylcarbonyl-$C_1$-$C_{12}$alkylcarbonyl substituted by one to five $R^8$, $C_3$-$C_{12}$cycloalkylaminocarbonyl or $C_3$-$C_{12}$cycloalkylaminocarbonyl wherein the cycloalkyl is substituted by one to five $R^9$, $C_2$-$C_{12}$alkenylaminocarbonyl or $C_2$-$C_{12}$alkenylaminocarbonyl wherein the alkenyl is substituted by one to five $R^8$, $C_2$-$C_{12}$alkynylaminocarbonyl or $C_2$-$C_{12}$alkynylaminocarbonyl wherein the alkynyl is substituted by one to five $R^8$, or is selected from $C(=O)R^{19}$ and $C(=S)R^{19}$. Preferably $R^{18}$ is hydrogen, cyano, carbonyl, thiocarbonyl, $C_1$-$C_{12}$alkylcarbonyl, $C_1$-$C_{12}$haloalkylcarbonyl, $C_1$-$C_{12}$alkylthiocarbonyl, $C_1$-$C_{12}$haloalkylthiocarbonyl, $C_1$-$C_{12}$alkylaminocarbonyl, $C_1$-$C_{12}$alkylaminothiocarbonyl, $C_2$-$C_{24}$ (total carbon number) dialkylaminocarbonyl, $C_2$-$C_{24}$ (total carbon number) dialkylaminothiocarbonyl, $C_1$-$C_{12}$alkoxyaminocarbonyl, $C_1$-$C_{12}$alkoxyaminothiocarbonyl, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, $C_1$-$C_{12}$thioalkoxycarbonyl, $C_1$-$C_{12}$thioalkoxythiocarbonyl, $C_1$-$C_{12}$alkylsulfonyl, $C_1$-$C_{12}$haloalkylsulfonyl, $C_3$-$C_{12}$cycloalkylcarbonyl, $C_3$-$C_{12}$halocycloalkylcarbonyl, $C_2$-$C_{12}$alkenylcarbonyl, $C_2$-$C_{12}$haloalkenylcarbonyl, $C_2$-$C_{12}$ alkynylcarbonyl, $C_2$-$C_{12}$haloalkynylcarbonyl, $C_3$-$C_{12}$cycloalkyl-$C_1$-$C_{12}$alkylcarbonyl, $C_3$-$C_{12}$halocycloalkyl-$C_1$-$C_{12}$alkylcarbonyl, $C_2$-$C_{12}$alkylsulfenyl-$C_1$-$C_{12}$alkylcarbonyl, $C_2$-$C_{12}$haloalkylsulfenyl-$C_1$-$C_{12}$alkylcarbonyl, $C_1$-$C_{12}$alkylsulfinyl-$C_1$-$C_{12}$alkylcarbonyl, $C_1$-$C_{12}$haloalkylsulfinyl-$C_1$-$C_{12}$alkylcarbonyl, $C_1$-$C_{12}$alkylsulfonyl-$C_1$-$C_{12}$alkylcarbonyl, $C_1$-$C_{12}$haloalkylsulfonyl-$C_1$-$C_{12}$alkylcarbonyl, $C_1$-$C_{12}$alkylcarbonyl-$C_1$-$C_{12}$alkylcarbonyl, $C_1$-$C_{12}$haloalkylcarbonyl-$C_1$-$C_{12}$alkylcarbonyl, $C_3$-$C_{12}$cycloalkylaminocarbonyl, $C_2$-$C_{12}$alkenylaminocarbonyl, $C_2$-$C_{12}$alkynylaminocarbonyl. More preferably, $R^{18}$ is $C_1$-$C_4$alkylcarbonyl or $C_1$-$C_4$alkylcarbonyl substituted by one to five $R^8$, $C_3$-$C_6$ cycloalkylcarbonyl or $C_3$-$C_6$cycloalkylcarbonyl wherein the cycloalkyl is substituted by one to five $R^9$; even more Preferably, $R^{18}$ is $C_1$-$C_4$alkylcarbonyl, $C_1$-$C_4$haloalkylcarbonyl, $C_3$-$C_6$cycloalkylcarbonyl or $C_3$-$C_6$halocycloalkylcarbonyl.

$R^{17}$ and $R^{18}$ together with the nitrogen atom to which they are bound may form a 3- to 6-membered heterocyclic ring which may be substituted by one to five $R^{11}$, or may be substituted with a keto, thioketo or nitroimino group.

$R^{19}$ is aryl or aryl substituted by one to five $R^{11}$, heterocyclyl or heterocyclyl substituted by one to five $R^{11}$. The aryl is preferably phenyl and the heterocyclyl is preferably pyridyl.

$R^{20}$ is hydrogen or $C_1$-$C_5$alkyl.

Each $R^{21}$ and $R^{22}$ is independently hydrogen, halogen, $C_1$-$C_5$alkyl or $C_1$-$C_8$haloalkyl.

Each $Z^1$ is independently halogen, $C_1$-$C_{12}$alkyl or $C_1$-$C_{12}$alkyl substituted by one to five $R^8$, nitro, $C_1$-$C_{12}$alkoxy or $C_1$-$C_{12}$alkoxy substituted by one to five $R^8$, cyano, $C_1$-$C_{12}$alkylsulfinyl, $C_1$-$C_{12}$ alkylsulfonyl, $C_1$-$C_{12}$haloalkylsulfinyl, $C_1$-$C_{12}$haloalkylsulfonyl, hydroxyl or thiol.

Preferably each $Z^1$ is independently halogen, cyano, $C_1$-$C_4$alkyl, $C_1$-$C_4$haloalkyl, $C_1$-$C_4$alkoxy, or $C_1$-$C_4$haloalkoxy, more preferably each $Z^1$ is independently hydrogen, halogen, methyl, halomethyl, methoxy or halomethoxy.

$R^{26}$ is hydrogen, azido, halogen, hydroxy, optionally substituted amino, optionally substituted alkoxy, optionally substituted alkoxycarbonyl or —$CO_2H$, more preferably —$N(R^{28})(R^{29})$, halogen, hydroxy, $C_1$-$C_8$alkoxy, $C_1$-$C_8$haloalkoxy, $C_1$-$C_8$alkoxycarbonyl, $C_1$-$C_8$haloalkoxycarbonyl, or —$CO_2H$.

$R^{27}$ is hydrogen, halogen, hydroxy, optionally substituted amino, optionally substituted alkyl, optionally substituted alkoxy, optionally substituted aloxycarbonyl, more preferably hydrogen, halogen, hydroxy, hydrogen, $C_1$-$C_8$alkyl, $C_1$-$C_8$alkoxy, $C_1$-$C_8$haloalkoxy, more preferably hydrogen, $C_1$-$C_8$alkyl, $C_1$-$C_8$alkoxy, or $C_1$-$C_8$haloalkoxy.

$R^{26}$ and $R^{27}$ may together be oxo, optionally substituted oxime, optionally substituted imine and optionally substituted hydrazone $R^{28}$ is hydrogen, cyano, formyl, thioformyl, alkylcarbonyl, haloalkylcarbonyl, alkyl-thiocarbonyl, haloalkyl-thiocarbonyl, mono- or di-alkylaminocarbonyl, mono- or di-alkylamino-thiocarbonyl, alkoxyaminocarbonyl, alkoxyamino-thiocarbonyl, alkoxycarbonyl, alkoxyalkylcarbonyl, alkoxy-thiocarbonyl, alkylthio-carbonyl, alkylthio-thiocarbonyl, alkylsulfonyl, haloalkylsulfonyl, cycloalkylcarbonyl, alkenylcarbonyl, alkynylcarbonyl, alkynylalkylcarbonyl, cycloalkyl-alkylcarbonyl, alkylthioalkyl-carbonyl, alkylsulfinylalkylcarbonyl, alkylsulfonylalkylcarbonyl, alkylcarbonylalkylcarbonyl, cycloalkylaminocarbonyl, alkenylaminocarbonyl, alkynylaminocarbonyl, —$CH_2$—$R^{30}$, —$C(O)R^{30}$ or —$C(S)R^{30}$, and each group from alkylcarbonyl to alkynylaminocarbonyl among the definitions of $R^8$ may be substituted; preferably $R^{28}$ is hydrogen, cyano, formyl, thioformyl, $C_1$-$C_{12}$alkylcarbonyl, $C_1$-$C_{12}$haloalkyl-carbonyl, $C_1$-$C_{12}$alkyl-thiocarbonyl, $C_1$-$C_{12}$haloalkyl-thiocarbonyl, mono-$C_1$-$C_{12}$ or di-$C_2$-$C_{24}$alkyl-aminocarbonyl, mono-$C_1$-$C_{12}$ or di-$C_2$-$C_{24}$alkylamino-thiocarbonyl, $C_1$-$C_{12}$alkoxy-aminocarbonyl, $C_1$-$C_{12}$alkoxyamino-thiocarbonyl, $C_1$-$C_{12}$alkoxy-carbonyl, $C_1$-$C_{12}$alkoxy-$C_1$-$C_{12}$alkyl-carbonyl, $C_1$-$C_{12}$alkoxy-thiocarbonyl, $C_1$-$C_{12}$alkylthio-carbonyl, $C_1$-$C_{12}$alkylthio-thiocarbonyl, $C_1$-$C_{12}$alkylsulfonyl, $C_1$-$C_{12}$haloalkylsulfonyl, $C_3$-$C_8$cycloalkyl-carbonyl, $C_2$-$C_6$alkenyl-carbonyl, $C_2$-$C_6$alkynyl-carbonyl, $C_2$-$C_6$alkynyl-$C_1$-$C_{12}$alkyl-carbonyl, $C_3$-$C_8$cycloalkyl-$C_1$-$C_{12}$alkyl-carbonyl, $C_1$-$C_{12}$alkylthio-$C_1$-$C_{12}$alkyl-carbonyl, $C_1$-$C_{12}$alkyl-sulfinyl-$C_1$-$C_{12}$alkyl-carbonyl, $C_1$-$C_{12}$alkylsulfonyl-$C_1$-$C_{12}$alkyl-carbonyl, $C_1$-$C_{12}$alkylcarbonyl-$C_1$-$C_{12}$alkyl-carbonyl, $C_3$-$C_8$cycloalkylamino-carbonyl, $C_2$-$C_6$alkenylamino-carbonyl, $C_2$-$C_6$alkynylamino-carbonyl, —$CH_2$—$R^{10}$, —$C(O)R^{10}$, or —$C(S)R^{10}$, and each group from $C_1$-$C_{12}$alkyl-carbonyl to $C_2$-$C_6$alkynyl-aminocarbonyl, among the definitions of $R^8$ may be optionally substituted; more preferably $R^{28}$ is hydrogen, cyano, carbonyl, thiocarbonyl, $C_1$-$C_6$alkyl-carbonyl, $C_1$-$C_6$haloalkyl-carbonyl, $C_1$-$C_6$alkyl-thiocarbonyl, $C_1$-$C_6$haloalkyl-thiocarbonyl, mono-$C_1$-$C_6$ or di-$C_2$-$C_{12}$) alkyl-aminocarbonyl, mono- $C_1$-$C_6$ or di-$C_2$-$C_{12}$)alkylamino-thiocarbonyl, $C_1$-$C_6$alkoxy-aminocarbonyl, $C_1$-$C_6$alkoxyamino-thiocarbonyl, $C_1$-$C_6$alkoxy-carbonyl, $C_1$-$C_6$alkoxy-$C_1$-$C_6$alkyl-carbonyl, $C_1$-$C_6$alkoxy-thiocarbonyl, $C_1$-$C_6$alkylthio-carbonyl, $C_1$-$C_6$alkylthio-thiocarbonyl, $C_1$-$C_6$alkylsulfonyl, $C_1$-$C_6$haloalkylsulfonyl, $C_3$-$C_6$cycloalkyl-carbonyl, $C_2$-$C_4$ alkenyl-carbonyl, $C_2$-$C_4$alkynyl-carbonyl, $C_2$-$C_4$alkynyl-$C_1$-$C_2$alkyl-carbonyl, $C_3$-$C_6$cycloalkyl-$C_1$-$C_2$alkyl- carbonyl, $C_1$-$C_6$alkylthio-$C_1$-$C_6$alkyl-carbonyl, $C_1$-$C_6$alkylsulfinyl-$C_1$-$C_6$alkyl-carbonyl, $C_1$-$C_6$ alkylsulfonyl-$C_1$-$C_6$alkyl-carbonyl, $C_1$-$C_6$alkylcarbonyl-$C_1$-$C_6$alkyl-carbonyl, $C_3$-$C_6$cycloalkylamino-carbonyl, $C_2$-$C_4$ alkenylamino-carbonyl, $C_1$-$C_6$alkynylamino-carbonyl, —$CH_2$—$R^{30}$-, —$C(O)R^{30}$ or —$C(S)R^{30}$ and each group from $C_1$-$C_6$alkyl-carbonyl to $C_1$-$C_6$alkynylamino-carbonyl among the definitions of $R^{28}$ may be optionally substituted. In one group of compounds $R^8$ is $C_1$-$C_6$alkyl-carbonyl, $C_1$-$C_6$haloalkyl-carbonyl, $C_3$-$C_6$cycloalkyl-$C_1$-$C_2$alkyl-carbonyl or $C_3$-$C_6$cycloalkyl-carbonyl.

$R^{29}$ is hydrogen, amino, hydroxy, cyano, alkyl, haloalkyl, cycloalkyl, alkenyl, alkynyl, alkylimino, alkoxy, alkylcarbonyl, alkylcarbonylamino, alkoxyalkyl, cyanoalkyl, alkoxycarbonylalkyl, —$CH_2$—$R^{30}$, —$C(O)R^{30}$ or —$C(S)R^{30}$, and each group from alkyl to alkylcarbonylamino among the definitions of $R^9$ may be substituted;

preferably $R^{29}$ is hydrogen, amino, hydroxy, cyano, $C_1$-$C_{12}$alkyl, $C_1$-$C_{12}$haloalkyl, $C_3$-$C_8$cycloalkyl, $C_2$-$C_6$alkenyl, $C_2$-$C_6$alkynyl, $C_1$-$C_{12}$alkylimino, $C_1$-$C_{12}$alkoxy, $C_1$-$C_{12}$alkyl-carbonyl, $C_1$-$C_{12}$alkyl-carbonylamino, $C_1$-$C_{12}$alkoxy-$C_1$-$C_{12}$alkyl, $C_1$-$C_{12}$cyanoalkyl, $C_1$-$C_{12}$alkoxycarbonyl-$C_1$-$C_{12}$alkyl, —$CH_2$—$R^{30}$, —$C(O)R^{30}$, or —$C(S)R^{30}$ and each group from $C_1$-$C_{12}$alkyl alkyl to $C_1$-$C_{12}$alkoxycarbonyl-$C_1$-$C_{12}$alkyl among the definitions of $R^{29}$ may be optionally substituted; preferably $R^{29}$ is hydrogen, amino, hydroxy, cyano, $C_1$-$C_6$alkyl, $C_1$-$C_{12}$haloalkyl, $C_3$-$C_6$ cycloalkyl, $C_2$-$C_4$alkenyl, $C_2$-$C_4$alkynyl, $C_1$-$C_6$alkylimino, $C_1$-$C_6$alkoxy, $C_1$- $C_6$alkyl-carbonyl, $C_1$-$C_6$alkyl-carbonylamino, $C_1$-$C_6$alkoxy-$C_1$-$C_6$alkyl, $C_3$-$C_6$cyanoalkyl, $C_1$-$C_6$alkoxycarbonyl-$C_1$-$C_6$alkyl, —$CH_2$—$R^{30}$, —$C(O)R^{30}$ or —$C(S)R^{30}$, and each group from $C_1$-$C_6$alkyl to $C_1$-$C_6$alkoxycarbonyl-$C_1$-$C_6$alkyl, among the definitions of $R^{29}$ may be optionally substituted. In one group of compounds $R^9$ is hydrogen, $C_1$-$C_6$alkoxy or benzyl.

$R^{28}$ and $R^{29}$, together with the N atom to which they are bound, may form a 3- to 6-membered heterocyclic ring which may be substituted and may further comprise N, O or S.

$R^{30}$ is phenyl which may be substituted, a 5- to 6-membered heterocyclic group which may be substituted and comprises at least one of N, O and S, optionally substituted $C_1$-$C_{12}$alkyl, amino, mono-$C_1$-$C_{12}$ or di($C_2$-$C_{24}$)alkylamino; preferably optionally substituted phenyl, pyridyl, pyrimidinyl, or a group (H1) to (H9), or an optionally substituted $C_1$-$C_6$alkyl, amino, mono-$C_1$-$C_6$ or di($C_1$-$C_{12}$)alkylamino group.

Preferably $R^{100}$ is $C_1$-$C_{12}$ alkyl, phenyl or heteroaryl as defined above, optionally substituted with one to five groups independently selected from cyano, halogen, $C_1$-$C_4$alkyl, $C_1$-$C_4$haloalkyl, $C_1$-$C_4$alkoxy, and $C_1$-$C_4$haloalkoxy, more preferably $C_1$-$C_6$alkyl, most preferably ethyl.

In one group of compounds, group A1 (applicable to all compounds of the invention bearing a group $R^1$ and $R^2$):

$R^1$ is trifluoromethyl.

$R^2$ is group A

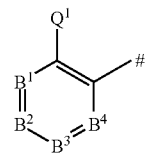

(A)

$B^1$, $B^2$, $B^3$, $B^4$ are independently C-$Q^1$ or nitrogen;

each $Q^1$ is independently hydrogen, halogen, cyano, $C_1$-$C_8$alkyl, $C_1$-$C_8$haloalkyl, $C_1$-$C_8$alkoxy or $C_1$-$C_8$haloalkoxy.

In one group of compounds, group A2, (applicable to all compounds bearing the group A') A' is selected from P1 to P6;

$A^1$, $A^2$, $A^3$, and $A^4$ are independently of each other C—H, C—$R^5$, or nitrogen;

$A^{1'}$, $A^{2'}$, $A^{3'}$, $A^{4'}$, $A^{5'}$ and $A^{6'}$ are independently of each other C—H, C—$R^5$ or nitrogen provided that no more than two of $A^{1'}$, $A^{2'}$, $A^{3'}$, $A^{4'}$, $A^{5'}$ and $A^{6'}$ are nitrogen;

each $R^5$ is independently hydrogen, halogen, $C_1$-$C_8$alkyl, $C_1$-$C_8$haloalkyl or $C_2$-$C_8$alkenyl;

Q is cyano, halogen, nitro, $NH_2$, arylsulfonyl or arylsulfonyl substituted by one to five groups independently selected from $C_1$-$C_4$alkyl and nitro, heterocyclyl or heterocyclyl substituted by one to five $Z^1$, —$OR^{14}$, —$C(=O)N(R^6)R^7$, —$CO(=O)R^{7a}$, —$C(=O)R^{13}$, or —$C(R^{15})(R^{16})N(R^{17})R^{18}$;

k is 0, 1, or 2;

$R^6$ is hydrogen, methyl, ethyl, methylcarbonyl or methoxycarbonyl;

$R^7$ is hydrogen, $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heterocyclyl-$C_1$-$C_6$alkylene or heterocyclyl-$C_1$-$C_6$alkylene wherein the heterocyclyl moiety is substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, aryl or aryl substituted by one to five $R^{10}$, heterocyclyl or heterocyclyl substituted by one to five $R^{10}$ and wherein each heterocyclyl moiety contains one or more ring members independently selected from O, N, C=O, C=N—$OR^{12}$, N—$R^{12}$, S, SO, $SO_2$, S=N—$R^{12}$ and SO=N—$R^{12}$, $C_1$-$C_8$ alkyl-N($R^6$)—C(=O)—$C_1$-$C_4$ alkylene, $C_1$-$C_8$haloalkyl-N($R^6$)—C(=O)—$C_1$-$C_4$alkylene, $C_3$-$C_8$cycloalkylaminocarbonyl-$C_1$-$C_4$alkylene, $C_1$-$C_6$alkyl-O—N=CH—, or $C_1$-$C_6$haloalkyl-O—N=CH;

$R^{7a}$ is hydrogen, $C_1$-$C_{15}$alkyl or $C_1$-$C_{15}$alkyl substituted by one to five $R^8$, $C_2$-$C_{15}$alkenyl or $C_2$-$C_{15}$alkenyl substituted by one to five $R^8$, $C_2$-$C_{15}$alkynyl or $C_2$-$C_{15}$alkynyl substituted by one to five $R^8$, $C_3$-$C_{10}$cycloalkyl or $C_3$-$C_{10}$cycloalkyl substituted by one to five $R^9$, aryl-$C_1$-$C_6$alkylene or aryl-$C_1$-$C_6$alkylene wherein the aryl moiety is substituted by one to five $R^{10}$, heteroaryl-$C_1$-$C_6$alkylene or heteroaryl-$C_1$-$C_6$alkylene wherein the heteroaryl moiety is substituted by one to five $R^{10}$, or heteroaryl or heteroaryl substituted by one to five $R^{10}$;

$R^{7b}$ is hydrogen, $C_1$-$C_{15}$ alkyl, $C_1$-$C_{15}$haloalkyl, $C_2$-$C_{15}$ alkenyl, $C_2$-$C_{15}$haloalkenyl, $C_2$-$C_{15}$ alkynyl, $C_2$-$C_{15}$haloalkynyl, $C_3$-$C_{10}$cycloalkyl, $C_1$-$C_{15}$ alkylcarbonyl or $C_1$-$C_{15}$alkoxycarbonyl;

each $R^8$ is independently halogen, cyano, nitro, hydroxy, $C_1$-$C_8$alkoxy, $C_1$-$C_8$haloalkoxy, $C_1$-$C_8$alkylcarbonyl, $C_1$-$C_8$alkoxycarbonyl, mercapto, $C_1$-$C_8$alkylthio, $C_1$-$C_8$haloalkylthio, $C_1$-$C_8$ alkylsulfinyl, $C_1$-$C_8$haloalkylsulfinyl, $C_1$-$C_8$alkylsulfonyl;

each $R^9$ is independently halogen or $C_1$-$C_8$alkyl. Preferably, each $R^9$ is independently chloro, fluoro or methyl;

each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy;

each $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkoxycarbonyl;

each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, aryl-$C_1$-$C_4$alkylene or aryl-$C_1$-$C_4$alkylene where the aryl moiety is substituted by one to three $R^{11}$, or heteroaryl-$C_1$-$C_4$alkylene or heteroaryl-$C_1$-$C_4$alkylene where the heteroaryl moiety is substituted by one to three $R^{11}$;

$R^{13}$ is halogen or imidazole;

each $R^{14}$ is independently hydrogen, $C_1$-$C_8$alkyl, phenylsulfonyl or phenylsulfonyl substituted by one to five groups independently selected from $C_1$-$C_4$alkyl and nitro;

$R^{15}$ and $R^{16}$ are each independently hydrogen, $C_1$-$C_{12}$alkyl, $C_1$-$C_{12}$haloalkyl, $C_3$-$C_8$cycloalkyl, $C_3$-$C_8$halocycloalkyl, $C_2$-$C_{12}$alkenyl or $C_2$-$C_{12}$haloalkenyl, $C_2$-$C_{12}$alkynyl, $C_2$-$C_{12}$haloalkynyl cyano, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, or $R^{15}$ and $R^{16}$ together with the carbon atom to which they are attached may form a 3 to 6-membered carbocyclic ring;

$R^{17}$ is hydrogen, $NH_2$, hydroxyl, $C_1$-$C_{12}$alkoxy, $C_1$-$C_{12}$haloalkoxy, $C_1$-$C_{12}$alkylcarbonylamino, $C_1$-$C_{12}$haloalkylcarbonylamino, $C_1$-$C_{12}$alkylamino, $C_1$-$C_{12}$haloalkylamino, $C_1$-$C_{12}$alkyl, $C_1$-$C_{12}$haloalkyl, $C_3$-$C_8$cycloalkyl, $C_3$-$C_8$halocycloalkyl, cyano, $C_1$-$C_{12}$alkenyl, $C_1$-$C_{12}$haloalkenyl, $C_2$-$C_{12}$alkynyl, $C_2$-$C_{12}$haloalkynyl, $C_1$-$C_{12}$alkylcarbonyl, $C_1$-$C_{12}$haloalkylcarbonyl, $C_1$-$C_8$alkoxycarbonyl, or $C_1$-$C_8$haloalkoxycarbonyl;

$R^{18}$ is hydrogen, cyano, carbonyl, thiocarbonyl, $C_1$-$C_{12}$alkylcarbonyl, $C_1$-$C_{12}$haloalkylcarbonyl, $C_1$-$C_{12}$alkylthiocarbonyl, $C_1$-$C_{12}$haloalkylthiocarbonyl, $C_1$-$C_{12}$alkylaminocarbonyl, $C_1$-$C_{12}$alkylaminothiocarbonyl, $C_2$-$C_{24}$ (total carbon number) dialkylaminocarbonyl, $C_2$-$C_{24}$ (total carbon number) dialkylaminothiocarbonyl, $C_1$-$C_{12}$alkoxyaminocarbonyl, $C_1$-$C_{12}$alkoxyaminothiocarbonyl, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, $C_1$-$C_{12}$thioalkoxythiocarbonyl, $C_1$-$C_{12}$thioalkoxythiocarbonyl, $C_1$-$C_{12}$alkylsulfonyl, $C_1$-$C_{12}$haloalkylsulfonyl, $C_3$-$C_{12}$cycloalkylcarbonyl, $C_3$-$C_{12}$halocycloalkylcarbonyl, $C_2$-$C_{12}$alkenylcarbonyl, $C_2$-$C_{12}$haloalkenylcarbonyl, $C_2$-$C_{12}$ alkynylcarbonyl, $C_2$-$C_{12}$haloalkynylcarbonyl, $C_3$-$C_{12}$cycloalkyl-$C_1$-$C_{12}$alkylcarbonyl, $C_3$-$C_{12}$halocycloalkyl-$C_1$-$C_{12}$alkylcarbonyl, $C_2$-$C_{12}$alkylsulfenyl-$C_1$-$C_{12}$alkylcarbonyl, $C_2$-$C_{12}$haloalkylsulfenyl-$C_1$-$C_{12}$alkylcarbonyl, $C_1$-$C_{12}$alkylsulfinyl-$C_1$-$C_{12}$alkylcarbonyl, $C_1$-$C_{12}$haloalkylsulfinyl-$C_1$-$C_{12}$alkylcarbonyl, $C_1$-$C_{12}$alkylsulfonyl-$C_1$-$C_{12}$alkylcarbonyl, $C_1$-$C_{12}$haloalkylsulfonyl-$C_1$-$C_{12}$alkylcarbonyl, $C_1$-$C_{12}$alkylcarbonyl-$C_1$-$C_{12}$alkylcarbonyl, $C_1$-$C_{12}$haloalkylcarbonyl-$C_1$-$C_{12}$alkylcarbonyl, $C_3$-$C_{12}$cycloalkylaminocarbonyl, $C_2$-$C_{12}$alkenylaminocarbonyl, $C_2$-$C_{12}$alkynylaminocarbonyl. More preferably, $R^{18}$ is $C_1$-$C_4$alkylcarbonyl or $C_1$-$C_4$alkylcarbonyl substituted by one to five $R^8$, $C_3$-$C_6$ cycloalkylcarbonyl or $C_3$-$C_6$cycloalkylcarbonyl wherein the cycloalkyl is substituted by one to five $R^9$; even more Preferably, $R^{18}$ is $C_1$-$C_4$alkylcarbonyl, $C_1$-$C_4$haloalkylcarbonyl, $C_3$-$C_6$cycloalkylcarbonyl or $C_3$-$C_6$halocycloalkylcarbonyl;

$R^{17}$ and $R^{18}$ together with the nitrogen atom to which they are bound may form a 3- to 6-membered heterocyclic ring which may be substituted by one to five $R^{11}$, or may be substituted with a keto, thioketo or nitroimino group;

$R^{19}$ is aryl or aryl substituted by one to five $R^{11}$, heterocyclyl or heterocyclyl substituted by one to five $R^{11}$ wherein aryl is phenyl and the heterocyclyl is preferably pyridyl;

$R^{20}$ is hydrogen or $C_1$-$C_8$alkyl;

each $R^{21}$ and $R^{22}$ is independently hydrogen, halogen, $C_1$-$C_8$alkyl or $C_1$-$C_8$haloalkyl;

each $Z^1$ is independently halogen, cyano, $C_1$-$C_4$alkyl, $C_1$-$C_4$haloalkyl, $C_1$-$C_4$alkoxy, or $C_1$-$C_4$haloalkoxy;

$R^{26}$ is —$N(R^{28})(R^{29})$, halogen, hydroxy, $C_1$-$C_8$alkoxy, $C_1$-$C_8$haloalkoxy, $C_1$-$C_8$alkoxycarbonyl, $C_1$-$C_8$haloalkoxycarbonyl, or —$CO_2H$;

$R^{27}$ is hydrogen, halogen, hydroxy, hydrogen, $C_1$-$C_8$alkyl, $C_1$-$C_8$alkoxy, $C_1$-$C_8$haloalkoxy, more preferably hydrogen, $C_1$-$C_8$alkyl, $C_1$-$C_8$alkoxy, or $C_1$-$C_8$haloalkoxy;

$R^{26}$ and $R^{27}$ may together be oxo, optionally substituted oxime, optionally substituted imine and optionally substituted hydrazone;

$R^{28}$ is hydrogen, cyano, formyl, thioformyl, $C_1$-$C_{12}$alkylcarbonyl, $C_1$-$C_{12}$haloalkyl-carbonyl, $C_1$-$C_{12}$alkyl-thiocarbonyl, $C_1$-$C_{12}$haloalkyl-thiocarbonyl, mono- $C_1$-$C_{12}$ or di-$C_2$-$C_{24}$alkyl-aminocarbonyl, mono-$C_1$-$C_{12}$ or di-$C_2$-$C_{24}$alkylamino-thiocarbonyl, $C_1$-$C_{12}$alkoxy-aminocarbonyl, $C_1$-$C_{12}$alkoxyamino-thiocarbonyl, $C_1$-$C_{12}$alkoxy-carbonyl, $C_1$-$C_{12}$alkoxy-$C_1$-$C_{12}$alkyl-carbonyl, $C_1$-$C_{12}$alkoxy-thiocarbonyl, $C_1$-$C_{12}$alkylthio-carbonyl, $C_1$-$C_{12}$alkylthio- thiocarbonyl, $C_1$-$C_{12}$alkylsulfonyl, $C_1$-$C_{12}$haloalkylsulfonyl, $C_3$-$C_8$cycloalkyl-carbonyl, $C_2$-$C_6$alkenyl-carbonyl, $C_2$-$C_6$alkynyl-carbonyl, $C_2$-$C_6$alkynyl-$C_1$-$C_{12}$alkyl-carbonyl, $C_3$-$C_8$cycloalkyl-$C_1$-$C_{12}$alkyl-carbonyl, $C_1$-$C_{12}$alkylthio-$C_1$-$C_{12}$alkyl-carbonyl, $C_1$-$C_{12}$alkyl-sulfinyl-$C_1$-$C_{12}$alkyl-carbonyl, $C_1$-$C_{12}$alkylsulfonyl-$C_1$-$C_{12}$alkyl-carbonyl, $C_1$-$C_{12}$alkylcarbonyl-$C_1$-$C_{12}$alkyl-carbonyl, $C_3$-$C_8$cycloalkylamino-carbonyl, $C_2$-$C_6$alkenylamino-carbonyl, $C_2$-$C_6$alkynylamino-carbonyl, —$CH_2$—$R^{10}$, —$C(O)R^{10}$, or —$C(S)R^{10}$, and each group from $C_1$-$C_{12}$alkylcarbonyl to $C_2$-$C_6$alkynyl-amino-carbonyl, among the definitions of $R^8$ may be optionally substituted;

$R^{29}$ is hydrogen, amino, hydroxy, cyano, $C_1$-$C_{12}$alkyl, $C_1$-$C_{12}$haloalkyl, $C_3$-$C_8$cycloalkyl, $C_2$-$C_6$alkenyl, $C_2$-$C_6$alkynyl, $C_1$-$C_{12}$alkylimino, $C_1$-$C_{12}$alkoxy, $C_1$-$C_{12}$alkyl-carbonyl, $C_1$-$C_{12}$alkyl-carbonylamino, $C_1$-$C_{12}$alkoxy-$C_1$-$C_{12}$alkyl, $C_1$-$C_{12}$cyanoalkyl, $C_1$-$C_{12}$alkoxycarbonyl-$C_1$-$C_{12}$alkyl, —$CH_2$—$R^{30}$, —$C(O)R^{30}$, or —$C(S)R^{30}$ and each group from $C_1$-$C_{12}$alkyl alkyl to $C_1$-$C_{12}$alkoxycarbonyl-$C_1$-$C_{12}$alkyl among the definitions of $R^{29}$ may be optionally substituted;

$R^{28}$ and $R^{29}$, together with the N atom to which they are bound, may form a 3- to 6-membered heterocyclic ring which may be substituted and may further comprise N, O or S;

optionally substituted phenyl, pyridyl, pyrimidinyl, or a group (H1) to (H9), or an optionally substituted $C_1$-$C_6$alkyl, amino, mono-$C_1$-$C_6$ or di($C_1$-$C_{12}$)alkylamino group;

wherein unless otherwise stated optionally substituents are independently selected from cyano, halogen, $C_1$-$C_4$alkyl, $C_1$-$C_4$haloalkyl, $C_1$-$C_4$alkoxy, and $C_1$-$C_4$haloalkoxy.

In one group of compounds, group A3, (applicable to all compounds of the invention bearing group A') A' is P1 or P2;

$A^1$, $A^2$ and $A^3$ are C—H;

Q is cyano, halogen, nitro, $NH_2$, $C_1$-$C_8$alkoxy, phenylsulfonyl or phenylsulfonyl substituted by one to five groups independently selected from $C_1$-$C_4$ alkyl and nitro, —C(=O)N($R^6$)$R^7$, —CO(=O)$R^{7a}$, —C(=O)$R^{13}$, —C($R^{15}$)($R^{16}$)N($R^{17}$)$R^{18}$, or a heterocycle selected from H1 to H9;

k is 0, 1 or 2, preferably 0;

each $R^5$ is independently halogen, $C_1$-$C_8$alkyl, $C_1$-$C_8$haloalkyl or $C_2$-$C_8$alkenyl;

$R^6$ is hydrogen;

$R^7$ is hydrogen, $C_1$-$C_8$alkyl, $C_1$-$C_8$haloalkyl, phenyl-$C_1$-$C_6$alkylene or phenyl-$C_1$-$C_6$alkylene wherein the phenyl moiety is substituted by one to five $R^{10}$, pyridyl-$C_1$-$C_6$alkylene or pyridyl-$C_1$-$C_6$alkylene wherein the pyridyl moiety is substituted by one to four $R^{10}$, thiazolyl-$C_1$-$C_6$alkylene or thiazolyl-$C_1$-$C_6$alkylene wherein the thiazolyl moiety is substituted by one or two $R^{10}$, phenyl or phenyl substituted by one to five $R^{10}$, pyridyl or pyridyl substituted by one to four $R^{10}$, thiazolyl or thiazolyl substituted by one or two $R^{10}$, $C_3$-$C_6$cycloalkyl or $C_3$-$C_6$cycloalkyl wherein one ring atom is replaced by O or S, $C_1$-$C_4$alkyl O—N=CH—, $C_1$-$C_4$haloalkyl-O—N=CH—, $C_1$-$C_4$alkyl-N($R^6$)—C(=O)—$CH_2$—, $C_1$-$C_4$haloalkyl-N($R^6$)—C(=O)—$CH_2$—, or a group of formula (Y)

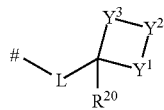

(Y)

L is a single bond or $C_1$-$C_6$alkylene, preferably a bond;

$Y^1$, $Y^2$ and $Y^3$ are independently of another O, $CR^{21}R^{22}$, C=O, C=N—$OR^{12}$, N—$R^{12}$, S, SO, $SO_2$, S=N—$R^{12}$ or SO=N—$R^{12}$, provided that at least one of $Y^1$, $Y^2$ or $Y^3$ is not $CR^{21}R^{22}$, C=O or C=N—$OR^{12}$, preferably two of $Y^1$, $Y^2$ and $Y^3$ are $CH_2$ and the other is S, SO or SO;

$R^{7a}$ is $C_1$-$C_{15}$alkyl, $C_1$-$C_{15}$haloalkyl, $C_2$-$C_{15}$alkenyl, $C_2$-$C_{15}$haloalkenyl, pyridyl or benzyl;

each $R^8$ is independently halogen, cyano, nitro, hydroxy, $C_1$-$C_8$alkoxy, $C_1$-$C_8$haloalkoxy, mercapto, $C_1$-$C_8$alkylthio, $C_1$-$C_8$haloalkylthio;

each $R^9$ is independently halogen or $C_1$-$C_8$alkyl;

each $R^{10}$ is independently halogen, cyano, nitro, $C_1$-$C_8$alkyl, $C_1$-$C_8$haloalkyl, $C_1$-$C_8$alkoxy, $C_1$-$C_8$haloalkoxy;

each $R^{11}$ is independently halogen, cyano, nitro, $C_1$-$C_8$alkyl, $C_1$-$C_8$haloalkyl, $C_1$-$C_8$alkoxy, $C_1$-$C_8$haloalkoxy or $C_1$-$C_8$alkoxycarbonyl;

each $R^{12}$ is independently hydrogen, cyano, $C_1$-$C_8$alkyl, $C_1$-$C_8$haloalkyl, $C_1$-$C_8$alkylcarbonyl, $C_1$-$C_8$haloalkylcarbonyl, $C_1$-$C_8$alkoxycarbonyl, $C_1$-$C_8$haloalkoxycarbonyl, $C_1$-$C_8$alkylsulfonyl, $C_1$-$C_8$haloalkylsulfonyl, phenyl-$C_1$-$C_4$alkylene or phenyl-$C_1$-$C_4$alkylene where the phenyl moiety is substituted by one to three $R^{11}$, or pyridyl-$C_1$-$C_4$alkylene or pyridyl-$C_1$-$C_4$alkylene where the pyridyl moiety is substituted by one to three $R^{11}$;

$R^{13}$ is halogen or imidazole, preferably chloro, fluoro or bromo;

$R^{15}$ and $R^{16}$ are each independently hydrogen, halogen, cyano, $C_1$-$C_4$alkyl or $C_1$-$C_4$haloalkyl;

$R^{17}$ is hydrogen, $C_1$-$C_5$alkyl, $C_1$-$C_5$alkoxy, $C_1$-$C_5$alkylcarbonyl, or $C_1$-$C_5$alkoxycarbonyl;

$R^{18}$ is $C_1$-$C_4$alkylcarbonyl or $C_1$-$C_4$alkylcarbonyl substituted by one to five $R^8$, $C_3$-$C_6$ cycloalkylcarbonyl or $C_3$-$C_6$cycloalkylcarbonyl wherein the cycloalkyl is substituted by one to five $R^9$;

$R^{20}$ is hydrogen or $C_1$-$C_5$alkyl, preferably hydrogen;

each $Z^1$ is independently hydrogen, halogen, methyl, halomethyl, methoxy or halomethoxy;

$R^{26}$ is —N($R^{28}$)($R^{29}$), halogen, hydroxy, $C_1$-$C_5$alkoxy, $C_1$-$C_8$haloalkoxy, $C_1$-$C_5$alkoxycarbonyl, $C_1$-$C_8$haloalkoxycarbonyl, or —$CO_2H$;

$R^{27}$ is hydrogen, $C_1$-$C_5$alkyl, $C_1$-$C_5$alkoxy, or $C_1$-$C_8$haloalkoxy.

$R^{28}$ is $C_1$-$C_6$alkyl-carbonyl, $C_1$-$C_6$haloalkyl-carbonyl, $C_3$-$C_6$cycloalkyl-$C_1$-$C_2$alkyl-carbonyl or $C_3$-$C_6$cycloalkyl-carbonyl;

$R^{29}$ is hydrogen, $C_1$-$C_6$alkoxy or benzyl.

In one group of compounds, group A4, applicable to all compounds of the invention bearing a group $R^1$, $R^2$ and A', $R^1$ and $R^2$ are as defined in group A1 and A' is as defined in group A2.

In one group of compounds, group A5, applicable to all compounds of the invention bearing a group $R^1$, $R^2$ and A', $R^1$ and $R^2$ are as defined in group A1 and A' is as defined in group A3.

In one group of compounds, group A6, applicable to all compounds of the invention bearing a group P, P is $C_1$-$C_6$alkoxy, N-pyrrolyl, N-imidazolyl, N-1,2,4-triazolyl, N-benzotriazolyl, or $C_1$-$C_6$alkylsulfinyl.

In one group of compounds, group A7, applicable to all compounds of the invention bearing a group P, optionally P is not $C_1$-$C_6$alkoxy, N-pyrrolyl, N-imidazolyl, N-1,2,4-triazolyl, N-benzotriazolyl, or $C_1$-$C_6$alkylsulfinyl.

In one group of compounds, group A8, applicable to all compounds of the invention bearing a group $R^2$, $R^2$ is aryl or aryl substituted by one to five $R^{70}$, or heteroaryl or heteroaryl substituted by one to five $R^{70}$, preferably phenyl or phenyl substituted by one to five $R^{70}$, more preferably phenyl substituted by one to three $R^{70}$, even more preferably $R^2$ is 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-, most preferably 3,5-dichloro-phenyl; each $R^{70}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_5$alkylthio-, $C_1$-$C_8$haloalkylthio-, $C_1$-$C_8$alkylsulfinyl-, $C_1$-$C_8$haloalkylsulfinyl-, $C_1$-$C_5$alkylsulfonyl-, $C_1$-$C_8$haloalkylsulfonyl-, $C_1$-$C_5$alkylcarbonyl-, $C_1$-$C_5$alkoxycarbonyl-, aryl or aryl substituted by one to five $R^{71}$, or heterocyclyl or heterocyclyl substituted by one to five $R^{71}$; preferably halogen, cyano, $C_1$-$C_5$alkyl, $C_1$-$C_8$haloalkyl or $C_1$-$C_8$alkoxy-, more preferably bromo, chloro, fluoro, cyano, methyl, trifluoromethyl, methoxy or trifluoromethoxy, preferably bromo, chloro, fluoro or trifluoromethyl, most preferably bromo or chloro; each $R^{71}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-, preferably bromo, chloro, fluoro, cyano, nitro, methyl, ethyl, trifluoromethyl, methoxy, difluoromethoxy or trifluoromethoxy, more preferably bromo, chloro, fluoro, nitro or methyl, most preferably chloro, fluoro or methyl.

In one group of compounds, group A9, applicable to all compounds of the invention bearing a group $R^2$, optionally $R^2$ is not aryl or aryl substituted by one to five $R^{70}$, or heteroaryl or heteroaryl substituted by one to five $R^{70}$, each $R^{70}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_5$alkoxycarbonyl, aryl or aryl substituted by one to five $R^{71}$, or heterocyclyl or heterocyclyl substituted by one to five $R^{71}$; each $R^{71}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-.

In one group of compounds, group A10, applicable to all compounds of the invention bearing a group $R^2$, $R^2$ is phenyl substituted by one to three $R^7$; each $R^7$ is independently halogen, cyano, $C_1$-$C_8$alkyl, $C_1$-$C_8$haloalkyl or $C_1$-$C_8$alkoxy-;

In one group of compounds, group A11, applicable to all compounds of the invention bearing a group $R^2$, optionally $R^2$ is not phenyl substituted by one to three $R^{70}$; each $R^{70}$ is independently halogen, cyano, $C_1$-$C_8$alkyl, $C_1$-$C_8$haloalkyl or $C_1$-$C_8$alkoxy-;

In one group of compounds, group A12, applicable to all compounds of the invention bearing a group $R^2$, $R^2$ is 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-.

In one group of compounds, group A13, applicable to all compounds of the invention bearing a group $R^2$, optionally $R^2$ is not 3-chloro-5-trifluoromethyl-phenyl-, 3,5-dichloro-phenyl-, 3,5-bis-(trifluoromethyl)-phenyl-, 3,5-dichloro-4-fluoro-phenyl-, 3,4,5-trichloro-phenyl- or 3-trifluoromethyl-phenyl-.

In one group of compounds, group A14, applicable to all compounds of the invention bearing a group $R^2$, $R^2$ is aryl or aryl substituted by one to five $R^{70}$, or heteroaryl or heteroaryl substituted by one to five $R^{70}$, preferably phenyl or phenyl substituted by one to five $R^7$; each $R^{70}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_5$alkylcarbonyl-, $C_1$-$C_8$alkoxycarbonyl-, aryl or aryl substituted by one to five $R^{71}$, or heterocyclyl or heterocyclyl substituted by one to five $R^{71}$; each $R^{71}$ is independently halogen, cyano, nitro, $C_1$-$C_8$alkyl, $C_1$-$C_8$haloalkyl, $C_1$-$C_8$alkoxy-, $C_1$-$C_8$haloalkoxy- or $C_1$-$C_8$alkoxycarbonyl-.

In one group of compounds, group A15, applicable to all compounds of the invention bearing a group $R^2$, optionally $R^2$ is not aryl or aryl substituted by one to five $R^{70}$, or heteroaryl or heteroaryl substituted by one to five $R^{70}$, preferably phenyl or phenyl substituted by one to five $R^7$; each $R^{70}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{71}$, or heterocyclyl or heterocyclyl substituted by one to five $R^{71}$; each $R^{71}$ is independently halogen, cyano, nitro, $C_1$-$C_8$alkyl, $C_1$-$C_8$halo alkyl, $C_1$-$C_8$alkoxy-, $C_1$-$C_8$haloalkoxy- or $C_1$-$C_8$alkoxycarbonyl-.

In one group of compounds, group A16, applicable to all compounds of the invention bearing a group A', A' may be group C

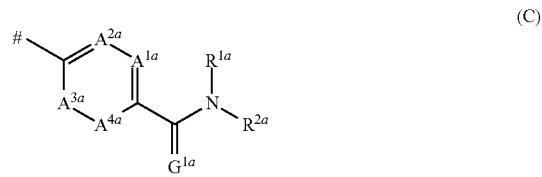

$A^{1a}$, $A^{2a}$, $A^{3a}$ and $A^{4a}$ are independently of each other C—H, C—$R^{5a}$ or nitrogen;

$G^{1a}$ is oxygen or sulfur;

$R^{1a}$ is hydrogen, $C_1$-$C_8$alkyl, $C_1$-$C_8$alkoxy-, $C_1$-$C_8$alkylcarbonyl-, $C_1$-$C_8$alkoxycarbonyl- or $C_1$-$C_8$haloalkoxycarbonyl-;

$R^{2a}$ is a group of formula D

where

La is a single bond or $C_1$-$C_6$alkylene; and $Y^{1a}$, $Y^{2a}$ and $Y^{3a}$ are independently of another $CR^{8a}R^{9a}$, C=O, C=N—$OR^{10a}$, N—$R^{10a}$, S, SO, $SO_2$, S=N—$R^{10a}$ or SO=N—$R^{10a}$, provided that at least one of $Y^{1a}$, $Y^{2a}$ or $Y^{3a}$ is not $CR^{8a}R^{9a}$, C=O or CN—$OR^{10a}$, preferably thietan-3-yl-, 1-oxo-thietan-3-yl-, 1,1-dioxo-thietan-3-yl- or 3-methyl-thietan-3-yl-, more preferably thietan-3-yl-, 1-oxo-thietan-3-yl-, or 1,1-dioxo-thietan-3-yl-;

each $R^{5a}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl- or $C_1$-$C_8$haloalkylsulfonyl-, or two $R^{5a}$ on adjacent carbon atoms together form a —CH=CH—CH=CH— bridge;

$R^{6a}$ is hydrogen, $C_1$-$C_8$haloalkyl or $C_1$-$C_8$alkyl;

each $R^{8a}$ and $R^{9a}$ is independently hydrogen, halogen, $C_1$-$C_8$alkyl or $C_1$-$C_8$haloalkyl;

each $R^{10a}$ is independently hydrogen, cyano, $C_1$-$C_8$alkyl, $C_1$-$C_8$haloalkyl, $C_1$-$C_8$alkylcarbonyl-, $C_1$-$C_8$haloalkylcarbonyl-, $C_1$-$C_8$alkoxycarbonyl-, $C_1$-$C_8$haloalkoxycarbonyl-, $C_1$-$C_8$alkylsulfonyl-, $C_1$-$C_8$haloalkylsulfonyl-, aryl-$C_1$-$C_4$alkylene- or aryl-$C_1$-$C_4$alkylene where the aryl moiety is substituted by one to three $R^{12a}$, or heteroaryl-$C_1$-$C_4$alkylene- or heteroaryl-$C_1$-$C_4$alkylene- where the heteroaryl moiety is substituted by one to three $R^{12a}$;

each $R^{11a}$ and $R^{12a}$ is independently halogen, cyano, nitro, $C_1$-$C_5$alkyl, $C_1$-$C_8$haloalkyl, $C_1$-$C_8$alkoxy-, $C_1$-$C_8$haloalkoxy- or $C_1$-$C_5$alkoxycarbonyl-.

In one group of compounds, group A17, applicable to all compounds of the invention bearing a group A', optionally A' is not A as defined in group A16.

Examples of chiral catalysts include chiral cinchona alkaloid derivatives, chiral thiourea derivatives, chiral urea derivatives, chiral aza-crown ether derivatives, chiral metal complexes, chiral amidine and guanidine derivatives, chiral pyrrolidine and imidazolidine derivatives, chiral scandium III complexes, chiral naphthyl phase transfer catalysts, chiral galodinium or strontium catalysts, chiral crown ether derivatives and chiral ligands for alkaline earth metals.

Chiral cinchona alkaloid derivatives are preferred and include alkaloid derivatives of the quaternary ammonium salts, tertiary amine derivatives, urea derivatives, thiourea derivatives and squaramide derivatives.

The term "chiral cinchona alkaloid derivatives" may overlap with the terms "chiral thiourea derivative" and "chiral urea derivative". Accordingly, the term "Chiral cinchona alkaloid derivatives" may in some embodiments exclude chiral thiourea derivatives and chiral urea derivatives. However, unless explicitly indicated the term "Chiral cinchona alkaloid derivatives" will include the relevant chiral thiourea derivatives and chiral urea derivatives.

In one embodiment the chiral catalysts are thiourea derivatives and chiral urea derivatives, in particular those that contain in the molecule a basic nitrogen atom in addition to the two nitrogen atoms of the urea or thiourea moiety, e.g. a primary, secondary or tertiary amine Examples include chiral cinchona alkaloid thiourea derivatives, chiral cinchona alkaloid urea derivatives, thiourea derivatives of cyclohexanediamine and urea derivatives of cyclohexanediamine Chiral cinchona alkaloid thiourea derivatives and thiourea derivatives of cyclohexanediamine are preferred.

For the nitromethane addition the preferred chiral catalysts are cinchona alkaloid derivatives, chiral thiourea derivatives and chiral metal complexes. These catalysts include those from groups 1, 2, 3, 4, 5, 7 and 11 below. Particularly preferred catalysts for are chiral cinchona alkaloid derivatives, particularly cinchona alkaloid derivatives of quaternary ammonium salts, cinchona alkaloid urea derivatives, cinchona alkaloid thiourea derivatives, and cinchona alkaloid squaramide derivatives. Even more preferred are cinchona alkaloid urea derivatives, cinchona alkaloid thiourea derivatives, most preferred being cinchona alkaloid thiourea derivatives.

For the cyanide addition the preferred catalysts are cinchona alkaloid derivatives, chiral ruthenium catalysts as well as gadolinium and strontium catalysts. These catalysts include those from groups 1, 2, 3, 4, 7 and 13. Most preferred catalysts are derivatives of cinchona alkaloid quaternary ammonium salts.

Examples of cinchona alkaloid quaternary ammonium salt derivatives include compounds of formula 1 (group 1)

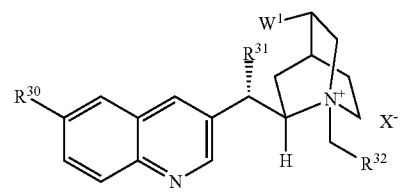

(1)

wherein
$W^1$ is ethyl or vinyl; $R^{30}$ is hydrogen or $C_1$-$C_4$alkoxy; $R^{31}$ is hydroxyl, $C_1$-$C_4$alkoxy, $C_2$-$C_4$alkenyloxy, optionally substituted aryloxy, optionally substituted heteroaryloxy or optionally substituted benzyloxy; $R^{32}$ is optionally substituted aryl or optionally substituted heteroaryl; X is an anion.

Preferably $W^1$ is vinyl.
Preferably $R^{30}$ is methoxy.
Preferably $R^{31}$ is hydroxyl, $C_1$-$C_4$alkoxy, $C_2$-$C_4$alkenyloxy, optionally substituted heteroaryloxy or benzyloxy, more preferably hydroxyl, optionally substituted pyrimidinyloxy or benzyloxy, most preferably hydroxyl.

Preferably X is a halogen, more preferably chloride or bromide. Preferably $R^{32}$ is phenyl or phenyl substituted by one to five $R^{33}$, naphthyl or naphthyl substituted by one to five $R^{33}$, anthracenyl or anthracenyl substituted by one to five $R^{33}$, or heteroaryl or heteroaryl substituted by one to four $R^{33}$; more preferably $R^{32}$ is phenyl or phenyl substituted by one to five $R^{33}$, naphthyl or naphthyl substituted by one to five $R^{33}$, anthracenyl or anthracenyl substituted by one to five $R^{33}$, pyrimidinyl or pyrimidinyl substituted by one to three $R^{33}$, or pyridyl or pyridyl substituted by one to four $R^{33}$; more preferably phenyl or phenyl substituted by one to five $R^{33}$, naphthyl or naphthyl substituted by one to five $R^{33}$, anthracenyl or anthracenyl substituted by one to five $R^{33}$, or pyridyl or pyridyl substituted by one to four $R^{33}$; more preferably $R^{32}$ is phenyl or phenyl substituted by one to five $R^{33}$, anthracenyl or anthracenyl substituted by one to five $R^{33}$, or pyridyl or pyridyl substituted by one to four $R^{33}$; even more preferably $R^{32}$ is phenyl or phenyl substituted by one to five substituents independently selected from halogen, methyl and methoxy, anthracenyl or anthracenyl substituted by one to five substituents independently selected from halogen, methyl and methoxy, pyridyl or pyridyl substituted by one to four halogen atoms, or group B

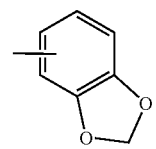

(B)

or group B substituted by one to four substituents independently selected from halogen, methyl and methoxy, even more preferably phenyl substituted by one to five substituents independently selected from halogen methyl and methoxy, anthracenyl or anthracenyl substituted by one to five substituents independently selected from halogen, methyl and methoxy or pyridyl or pyridyl substituted by one to four halogen atoms, even more preferably phenyl substituted by one to five substituents independently selected from halogen methyl and methoxy or anthracenyl. Each $R^{33}$ is independently halogen, cyano, nitro, $C_1$-$C_8$alkyl, $C_1$-$C_8$haloalkyl, $C_1$-$C_8$alkoxy, $C_1$-$C_8$haloalkoxy, $C_3$-$C_8$cycloalkyl, phenyl or phenyl substituted by one to five halogen, and wherein two $R^{33}$ substituents on adjacent carbon atoms may together form a partially saturated 5-7 membered ring containing one or two heteroatoms independently selected from O, N($R^{34}$) and S; and each $R^{34}$ is independently hydrogen or $C_1$-$C_4$ alkyl. Preferably each $R^{33}$ is independently halogen, cyano, nitro, $C_1$-$C_4$alkyl, $C_1$-$C_4$haloalkyl, $C_1$-$C_4$alkoxy, aryl or $C_1$-$C_4$haloalkoxy, and wherein any two $R^{33}$ substituents on adjacent carbon atoms may together form a partially saturated 5 membered ring containing one or two O atoms, more preferably each $R^{33}$ is independently halogen, methyl, halomethyl, methoxy, phenyl or halomethoxy, and wherein any two $R^{33}$ substituents on adjacent carbon atoms may together form a partially saturated 5 membered ring containing one or two O atoms, more preferably each $R^{33}$ is independently halogen, methyl, phenyl or methoxy, most preferably each $R^{33}$ is independently fluorine, methyl, phenyl or methoxy.

Examples include

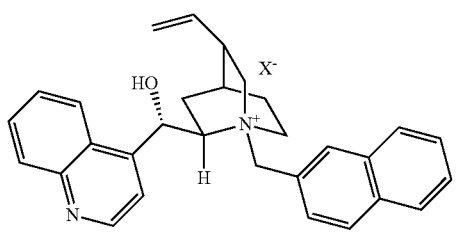

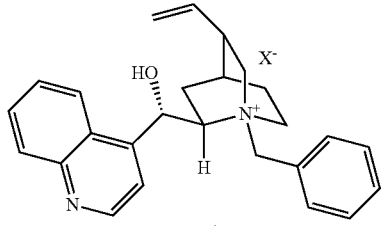

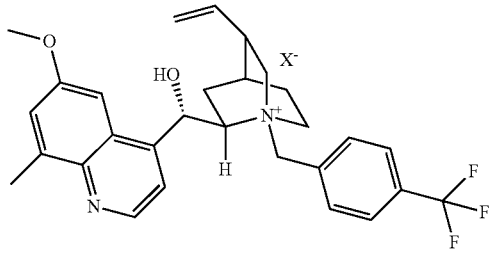

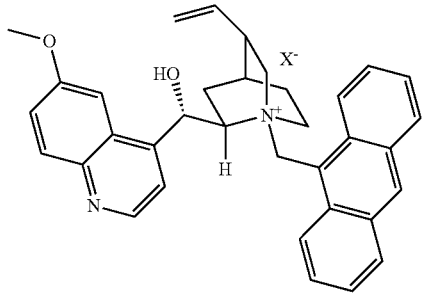

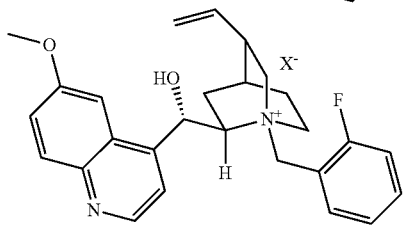

-continued

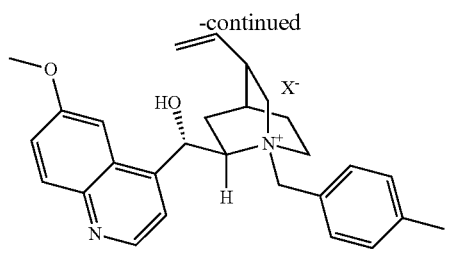

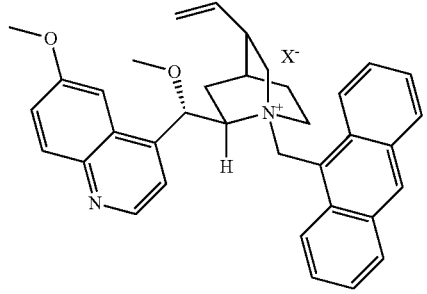

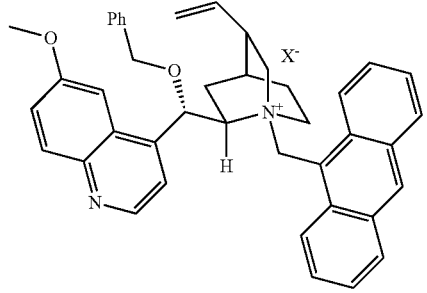

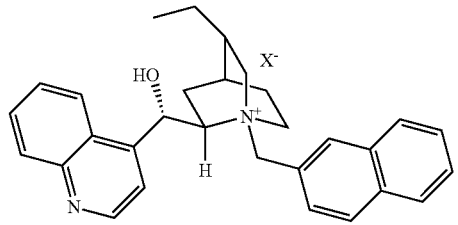

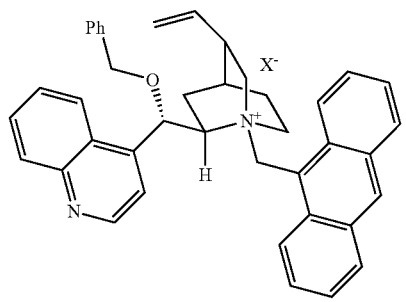

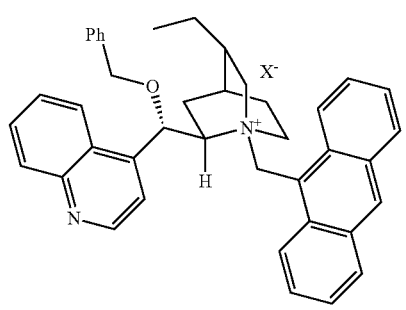

-continued
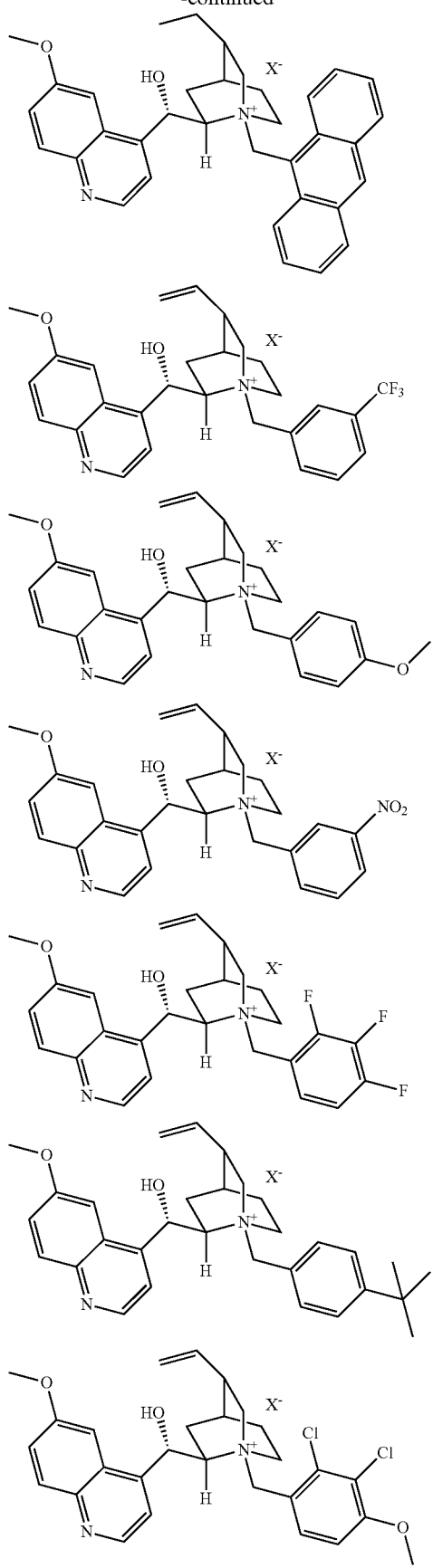
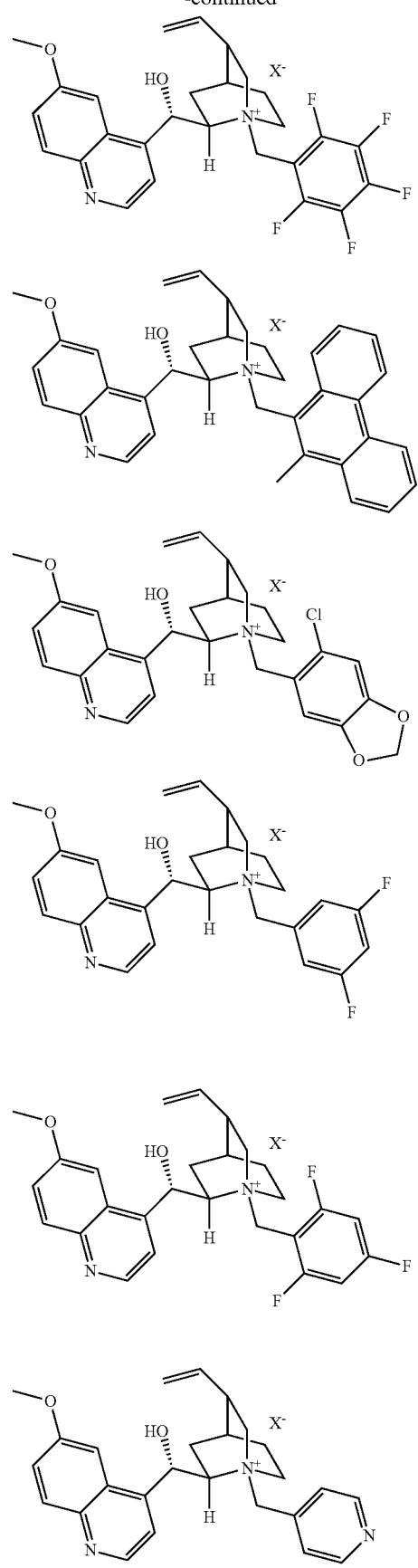

55
-continued
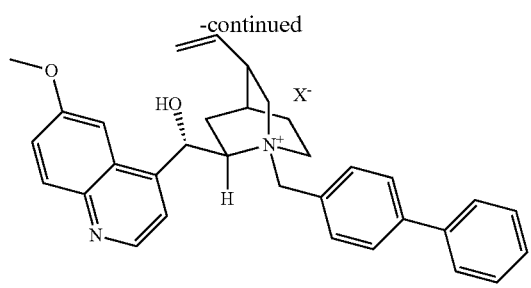
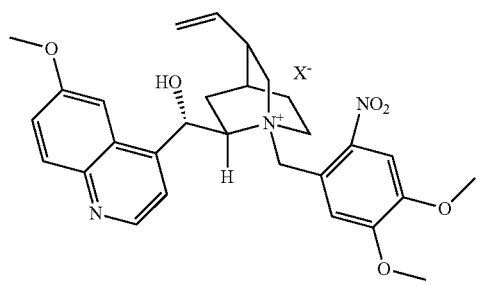
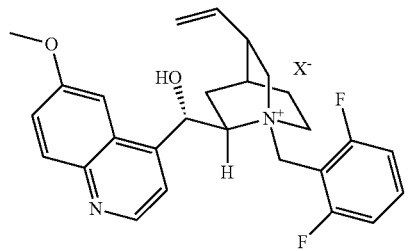
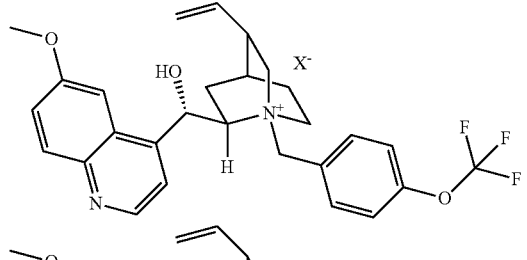
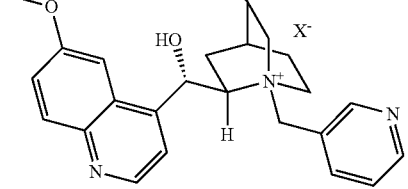
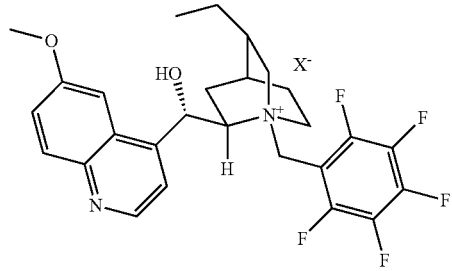
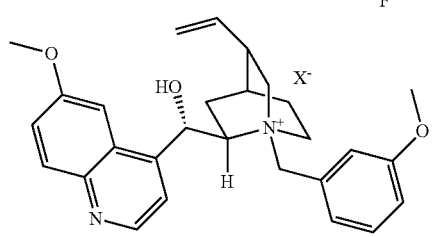
56
-continued
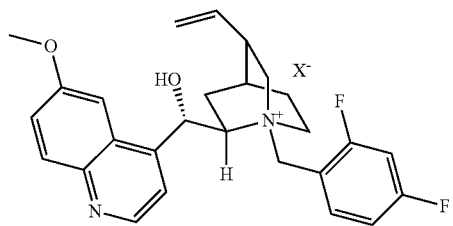
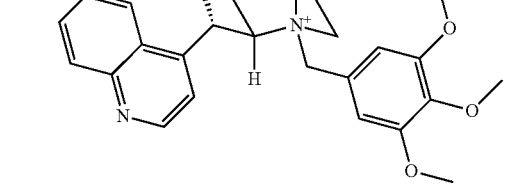
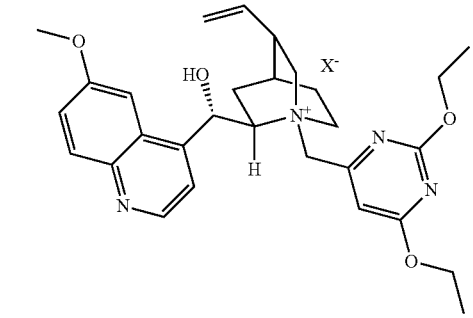
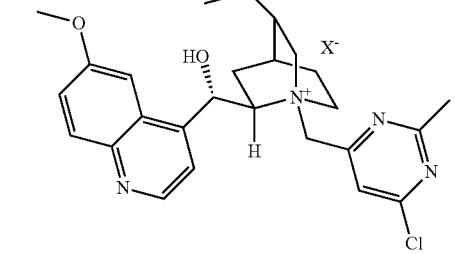
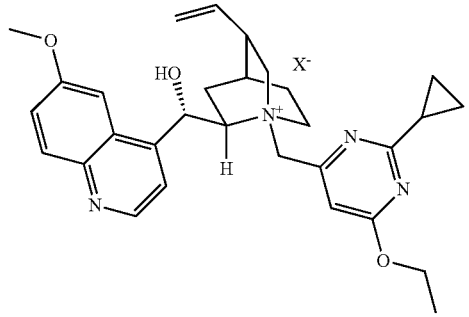
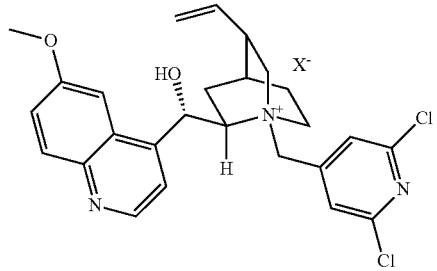

-continued

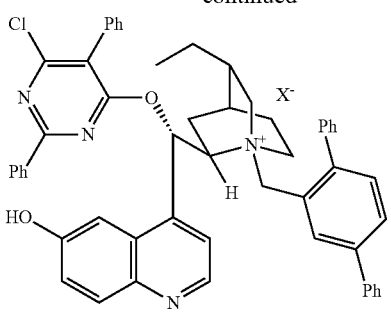

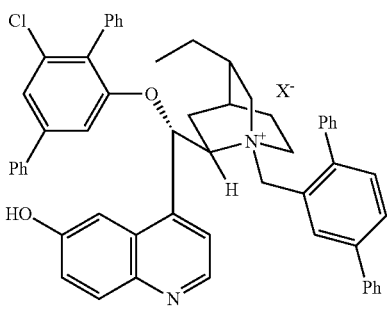

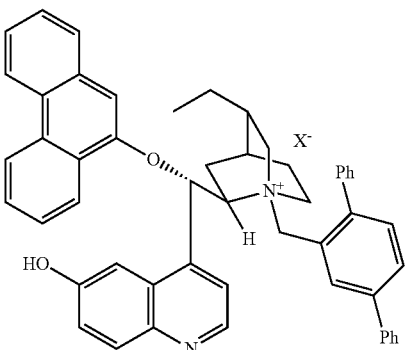

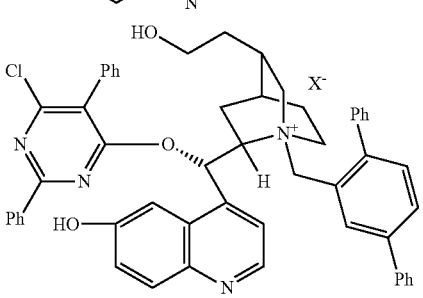

wherein X is an anion, preferably halogen, more preferably chloride or bromide.

Examples of cinchona alkaloid quaternary ammonium salt derivatives are described for example in Arai et al., *Tet. Lett.* 1999, 4215; S. Colonna, H. Hiemstra, H. Wynberg, *J. Chem. Soc. Chem. Commun.* 1978, 238; E. J. Corey, F. Y. Zhang, *Org. Lett.* 2000, 2, 4257; D. Y. Kim, S. C. Huh, *Tetrahedron* 2001, 57, 8933; M. Hua, H. Cui, L. Wang, J. Nie, J. Ma, *Angew. Chem.* 2010, 122, 2832; *Angew. Chem. Int. Ed.* 2010; and T. Ooi, K. Maruoka, *Acc. Chem. Res.* 2004, 37, 526; Provencher, B. A., Bartelson, K. J., Liu, Y., Foxman, B., Deng, L. *Angew. Chem. Int. Ed.* 2011, 50, 10565; Liu, Y., Provencher, B. A., Bartelson, K. J., Deng, L. *Chem. Sci.* 2011, 2, 1301

Examples of cinchona alkaloid tertiary amine derivatives include compounds of formula 2 (group 2)

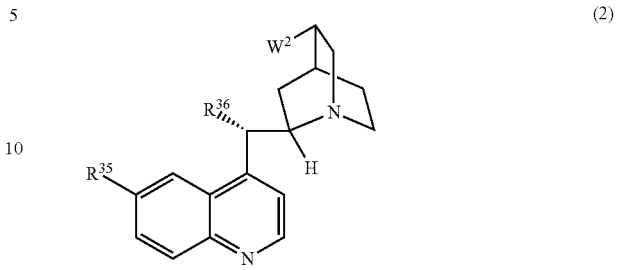

(2)

$W^2$ is ethyl or vinyl; $R^{35}$ is hydrogen or $C_1$-$C_4$alkoxy; $R^{36}$ is hydroxyl, $C_1$-$C_4$alkoxy, $C_2$-$C_4$alkenyloxy or optionally substituted benzyloxy.

Preferably $W^2$ is vinyl.
Preferably $R^{35}$ is methoxy.
Preferably $R^{36}$ is hydroxyl, $C_1$-$C_4$alkoxy, $C_2$-$C_4$alkenyloxy or benzyloxy, most preferably hydroxyl.
Examples include:

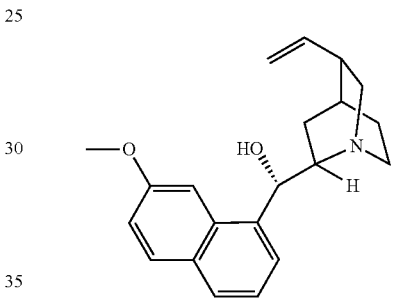

as described in A. Latvala, S. Stanchev, A. Linden, M. Hesse, *Tet. Asym.* 1993, 2, 173.

Examples of cinchona alkaloid urea and thiourea derivatives include compounds of formula 3 (group 3)

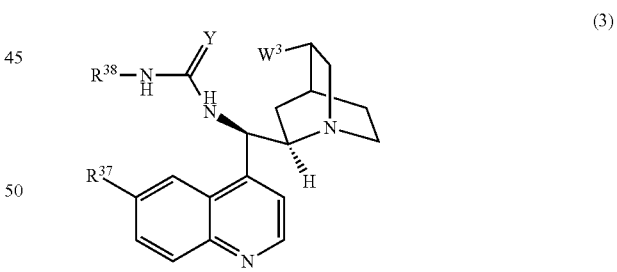

(3)

Y is S or O, $W^3$ is ethyl or vinyl; $R^{37}$ is hydrogen or $C_1$-$C_4$alkoxy; $R^{38}$ is optionally substituted aryl or optionally substituted $C_3$-$C_{10}$cycloalkyl.

Preferably Y is S.
Preferably $W^3$ is vinyl or ethyl.
Preferably $R^{37}$ is methoxy.
Preferably $R^{38}$ is phenyl optionally substituted by one to five $R^{39}$ or $C_5$-$C_6$cycloalkyl optionally substituted by $R^{40}$, more preferably phenyl optionally substituted by one to five $R^{39}$.

$R^{39}$ is halogen, cyano, $C_1$-$C_4$alkyl, $C_1$-$C_4$haloalkyl, $C_1$-$C_4$alkoxy, $C_1$-$C_4$haloalkoxy, preferably $C_1$-$C_4$ haloalkyl, more preferably $C_1$-$C_4$haloalkyl.

$R^{40}$ is $NH_2$, halogen, cyano, $C_1$-$C_4$alkyl, $C_1$-$C_4$haloalkyl, $C_1$-$C_4$alkoxy, $C_1$-$C_4$haloalkoxy, preferably $NH_2$.

Examples include

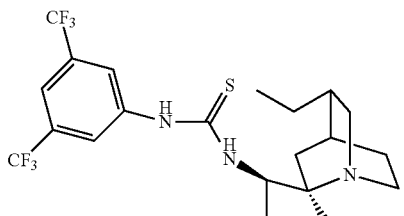

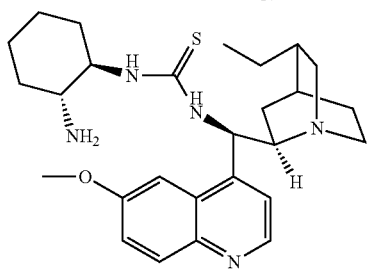

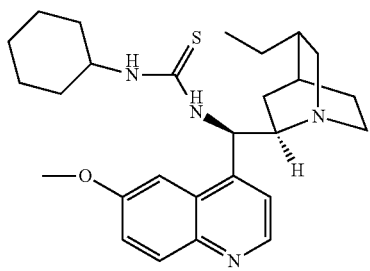

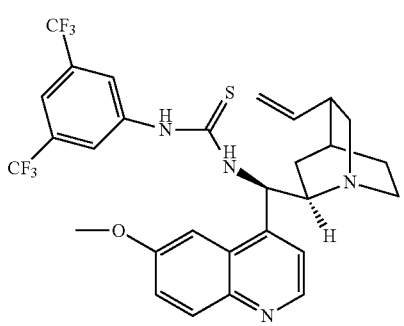

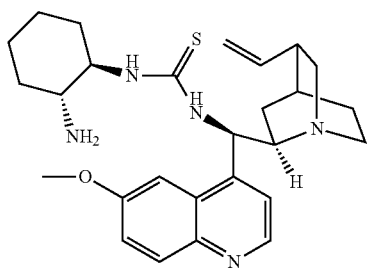

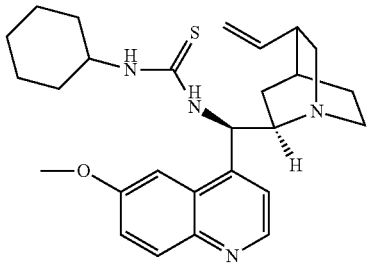

as described in B. Vakulya, S. Varga, A. Csampai, T. Soós, *Org. Lett.* 2005, 7, 1967; B. Vakulya, S. Varga, T. Soós, *J. Org. Chem.* 2008, 73, 3475; P. Li, Y. Wang, X. Liang, J. Ye, *Chem. Commun.* 2008, 3302; and C. Oliva, A. Silva, F. Paz, J. Calvaleiro, *Synlett,* 2010, 7, 1123-1127.

Examples of squaramide catalysts include compound of formula 4 (group 4)

(4)

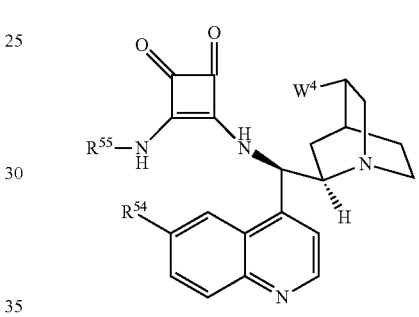

wherein $W^4$ is ethyl or vinyl; $R^{54}$ is hydrogen or $C_1$-$C_4$alkoxy; $R^{55}$ is optionally substituted aryl.

Preferably $W^4$ is vinyl

Preferably $R^{54}$ is methoxy.

Preferably $R^{55}$ is phenyl optionally substituted by one to five $R^{56}$ or $C_5$-$C_6$cycloalkyl optionally substituted by $R^{40}$.

$R^{56}$ is halogen, cyano, $C_1$-$C_4$alkyl, $C_1$-$C_4$haloalkyl, $C_1$-$C_4$alkoxy, $C_1$-$C_4$haloalkoxy, preferably $C_1$-$C_4$haloalkyl.

Examples include those wherein in the compound of formula X, $R^{54}$ is H or OMe and $R^{55}$ is 4-$CF_3$—$C_6H_4$ or 3,5-$(CF_3)_2$—$C_6H_3$ as described in Yang, W.; Du, D. Org. Lett., 2010, 12 (23), 5450-5453.

Examples of thiourea derivatives of cyclohexanediamine or diamines (group 5) include the following

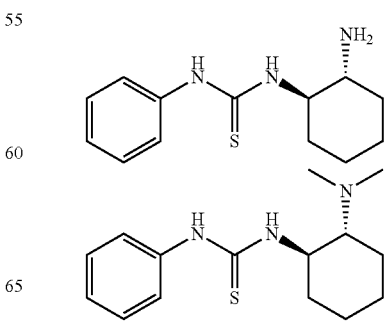

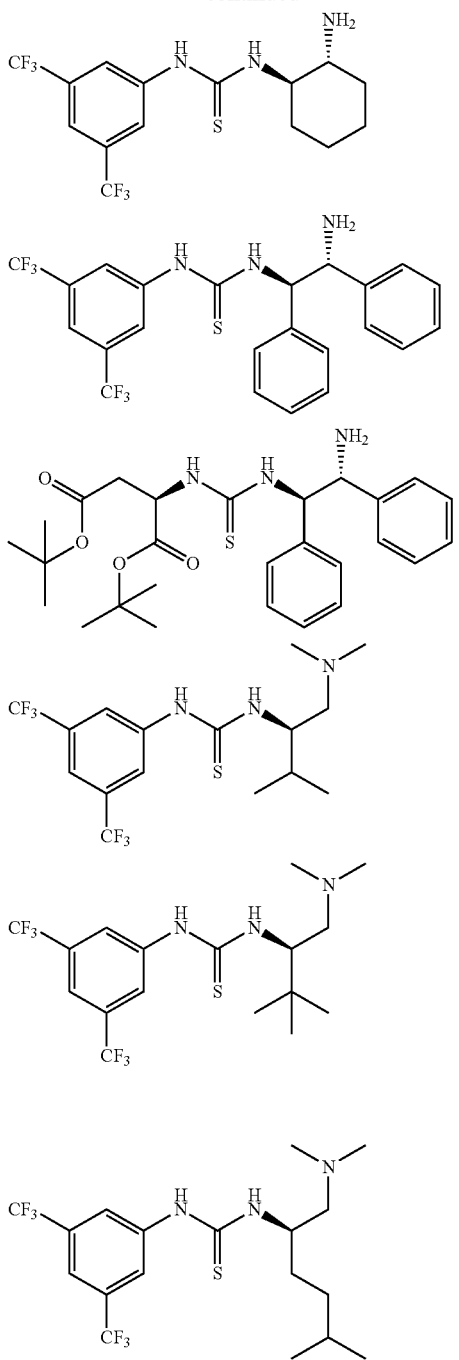

Examples of thiourea derivatives of cyclohexanediamine are described in K. Mei, M. Jin, S. Zhang, P. Li, W. Liu, X. Chen, F. Xue, W. Duan, W. Wang, *Org. Lett.* 2009, 11, 2864, and B. Vakulya, S. Varga, T. Soós, *J. Org. Chem.* 2008, 73, 3475.

Examples of thiourea derivatives of diamines are described in He, Tianxiong; Qian, Jing-Ying; Song, Hong-Liang; Wu, Xin-Yan Synlett 2009, 19, 3195-319 and Kokotos, C. G.; Kokotos, G., Advanced Synthesis & Catalysis 2009, 351(9), 1355-1362 and Manzano, R.; Andres, J. M.; Alvarez, R.; Muruzabal, M. D.; de Lera, A. R.; Pedrosa, R. Chem. Eur. J. 2011, 17, 5931.

Examples of aza-crown ethers (group 6) include compound of formula 5

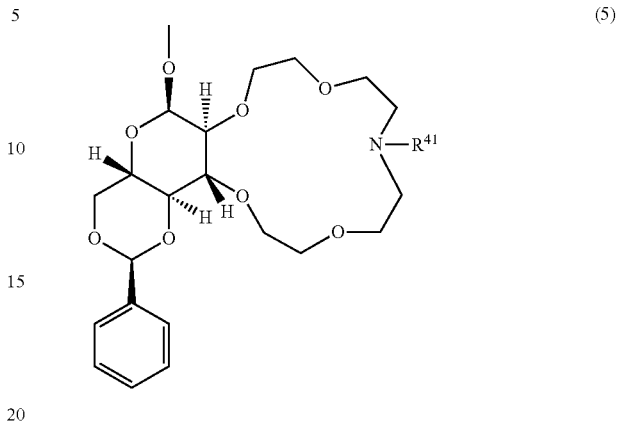

(5)

$R^{41}$ is hydrogen, $C_1$-$C_{10}$alkyl, $C_1$-$C_{10}$hydroxyalkyl $C_1$-$C_5$alkoxy-$C_1$-$C_5$alkyl, $C_1$-$C_8$alkoxycarbonyl, $C_1$-$C_8$alkyl optionally substituted aryl, aryl-$C_1$-$C_4$alkyl wherein the aryl is optionally substituted, $(aryl)_2P(O)C_1$-$C_4$ alkyl wherein each aryl is optionally substituted.

Preferably $R^{41}$ is hydrogen, $C_1$-$C_{10}$alkyl, $C_1$-$C_{10}$hydroxyalkyl, $C_1$-$C_5$alkoxy-$C_1$-$C_5$alkyl, $C_1$-$C_8$alkoxycarbonyl-$C_1$-$C_5$alkyl, phenyl, phenyl-$C_1$-$C_4$alkyl, $(phenyl)_2P(O)C_1$-$C_4$ alkyl.

Examples of aza crown ethers include those wherein $R^{41}$ is $C_6H_5$, $CH_2C_6H_5$, $CH_3$—$(CH_2)_3$, $CH_3$—$(CH_2)_9$, $CH_2CH_2OH$, $C_6H_{11}$, $CH_2CO_2CH_3$, hydrogen, $CH_2CH_2OCH_3$, $(CH_2)_4P(O)Ph_2$.

Examples of aza-crown ethers are described in P. Bakó, A. Szöllösy, P. Bombicz, L. Töke, *Synlett* 1997, 291 and T. Bakó, P. Bakó, A. Szöllösy, M. Czugler, G. Keglevich, L. Töke, *Tet. Asym.* 2002, 203.

Examples of chiral metal complexes (group 7) include the following as described in G. Sundararajan, N. Prabagaran, *Org. Lett.* 2001, 3, 389;

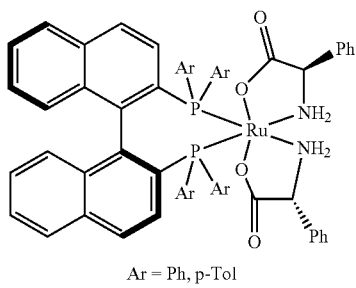

Ar = Ph, p-Tol as described in Kurono, N.; Nii, N.; Sakaguchi, Y.; Uemura, M.; Ohkuma, T. Angew. Chem. Int. Ed. 2011, 50, DOI: 10.1002/anie.201100939

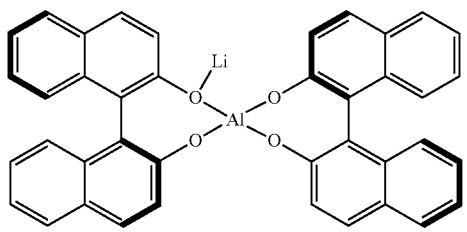

as described in. Keller, N. Veldman, A. L. Spek, B. L. Feringa, Tetrahedron: Asymmetry 1997, 8, 3403; LaK$_3$tris ((R)-binaphthoxide)) as described in K. Funabashi, Y. Saida, M. Kanai, T. Arai, H. Sasai, M. Shibasaki, Tetrahedron Lett. 1998, 39, 7557; and

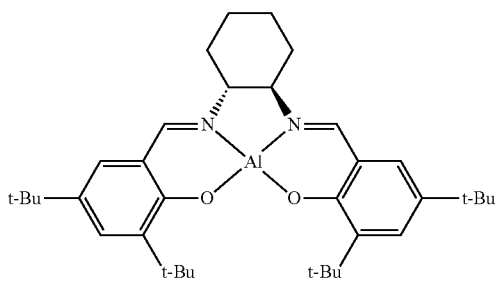

(S,S)-(salen)Al
variations thereof include [(S,S)-(salen)Al]$_2$O, (S,S)-(salen)AlMe, (S,S)-(salen)AlCl and are described in M. S. Taylor, D. N. Zalatan, A. M. Lerchner, E. N. Jacobsen, J. Am. Chem. Soc. 2005, 127, 1313;

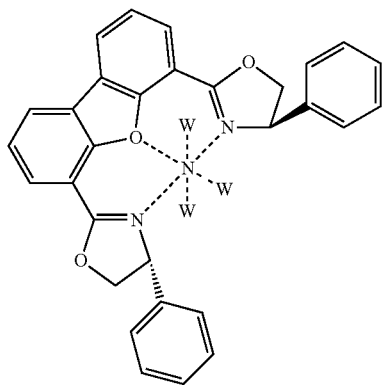

in combination with an achiral amine, e.g. 2,2,6,6-tetramethylpiperidine, as described in K. Itoh, S. Kanemasa, J. Am. Chem. Soc. 2002, 124, 13394.

Examples of chiral amidines and guanidines (group 8) include compounds of formula 6

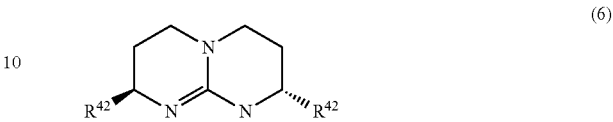

(6)

wherein each $R^{42}$ is C(H)Ph$_2$, or CH$_2$OR$^{43}$, wherein $R^{43}$ is t-BuPh$_2$Si, H or benzyl, e.g. as described in A. P. Davis, K. J. Dempsey, Tetrahedron: Asymmetry 1995, 6, 2829;

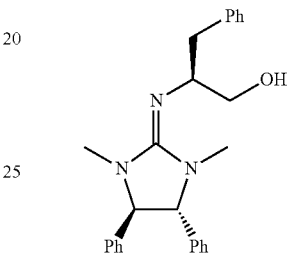

as described in Zhang, G.; Kumamoto, T.; Heima, T.; Ishikawa, T. Tetrahedron Lett. 2010, 51, 3927.

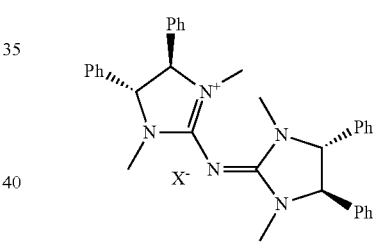

Where X is a halogen or BF$_4$ of PF$_6$, most preferably chloride as described in Ma, T.; Fu, X.; Kee, C. W.; Zong, L.; Pan, Y.; Huang, K.; Tan, C. J. Am. Chem. Soc. 2011, 133, 2828 and

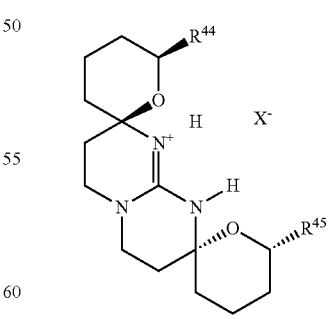

wherein $R^{44}$ and $R^{45}$ are independently C$_1$-C$_4$ alkyl, C$_1$-C$_4$ alkoxy-C$_1$-C$_4$ alkyl, TBDMS-C$_1$-C$_4$ alkyl or TBDPS-C$_1$-C$_4$ alkyl, preferably both $R^{44}$ and $R^{45}$ are either hydroxymethyl, TMDMS-methyl or TBDPS-methyl, and wherein X is an anion, preferably halogen or BF$_4$—, more preferably chloride or BF$_4$—, e.g. as described in M. T. Allingham, A. Howard-Jones, P. J. Murphy, D. A. Thomas, P. W. R. Caulkett, *Tetrahedron Lett.* 2003, 44, 8677.

Examples of the pyrrolidine derivatives as chiral catalysts (group 9) include proline, e.g. in combination with trans-2,5-dimethylpiperazine as described in S. Hanessian, V. Pham, *Org. Lett.* 2000, 2, 2975;

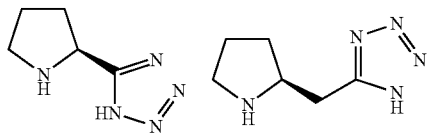

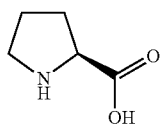

as described in C. E. T. Mitchell, S. E. Brenner and S. V. Ley, *Chem. Commun.,* 2005, 5346 and C. E. T. Mitchell, S. E. Brenner, J. Garcia-Fortanet and S. V. Ley, *Org. Biomol. Chem.,* 2006, 4, 2039;

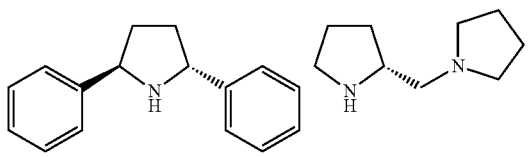

as described in N. Halland, R. G. Hazell, K. A. Jorgensen, *J. Org. Chem.* 2002, 67, 8331;

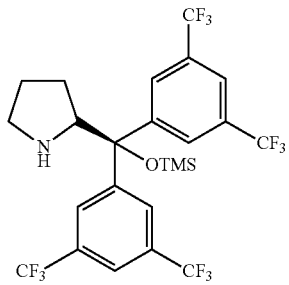

as described in C. Oliva, A. Silva, F. Paz, J. Calvaleiro, *Synlett,* 2010, 7, 1123-1127; and

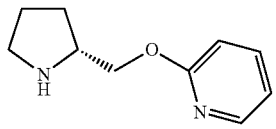 [SMILES: c1ccc(OC[C@H]2CCCN2)nc1]

as described in Xu, D.; Shi, S.; Wang, Y. European Journal of Organic Chemistry 2009, (28), 4848-4853.

Examples of chiral imidazoline catalysts (group 10) include

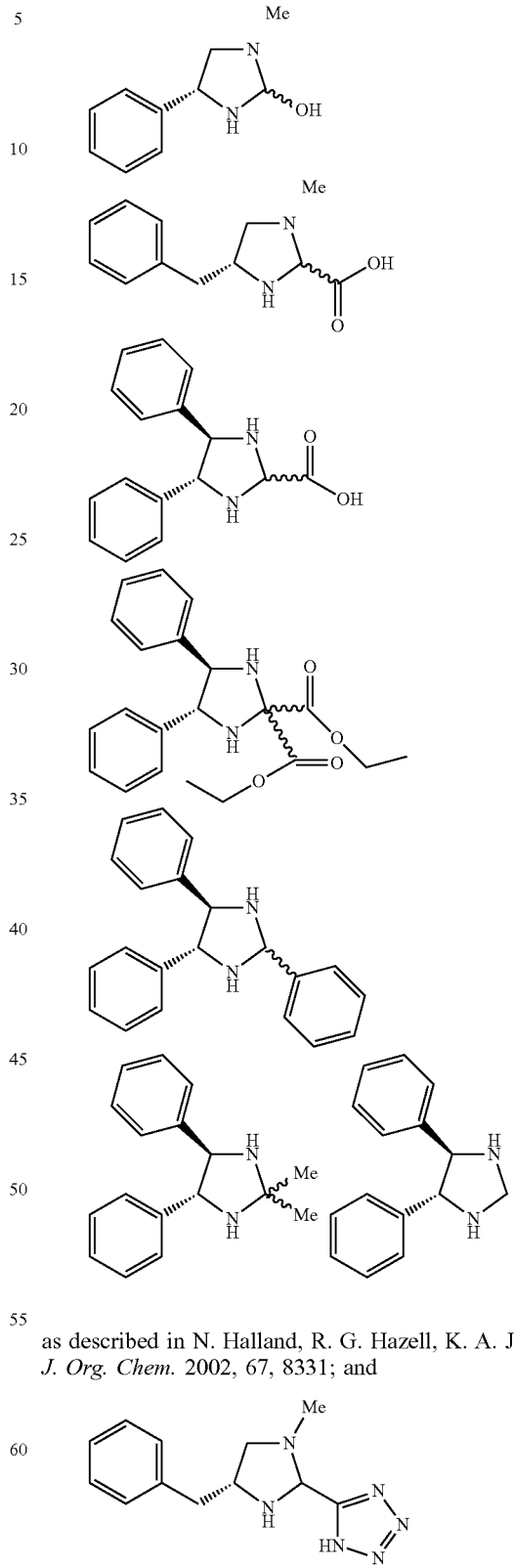

as described in N. Halland, R. G. Hazell, K. A. Jorgensen, *J. Org. Chem.* 2002, 67, 8331; and

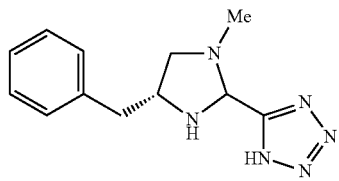 [SMILES: CN1C[C@@H](Cc2ccccc2)NC1c1nnn[nH]1]

as described in A. Prieto, N. Halland, K. A. Jøorgensen, *Org. Lett.* 2005, 7, 3897.

Examples of chiral N,N'-dioxide-scandium III complexes (group 11) include ligand-Sc(OTf)$_3$ complexes wherein the ligand is a compound of formula 7 or 8

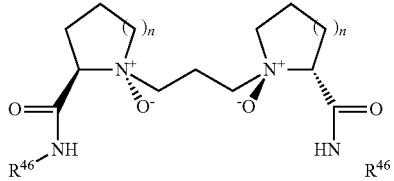
(9)

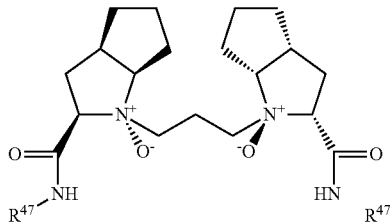
(10)

wherein $R^{46}$ and $R^{47}$ are phenyl optionally substituted by one to five halogen, $C_1$-$C_4$ alkyl, $C_1$-$C_4$ haloalkyl, $C_1$-$C_4$ alkoxy, $C_1$-$C_4$ haloalkoxy and wherein n is 1 or 2;
Examples include those wherein n is 1 and $R^{46}$ is 2,6-iPr$_2$C$_6$H$_3$; n is 1 and $R^{46}$ is C$_6$H$_5$; n is 1 and $R^{46}$ is 2-MeC$_6$H$_4$; n is 2 and $R^{46}$ is 2,6-iPr$_2$C$_6$H$_3$; $R^{47}$ is 2,6-iPr$_2$-C$_6$H$_3$; as described in L. Wang, Q. Zhang, X. Zhou, X. Liu, L. Lin, B. Qin, X. Feng, *Chemistry-A European Journal*, 2010, 16, (26), 7696-7699, Chiral binaphthyl phase transfer catalysts (group 12) include compounds of formula 11, 12, 13 and 14

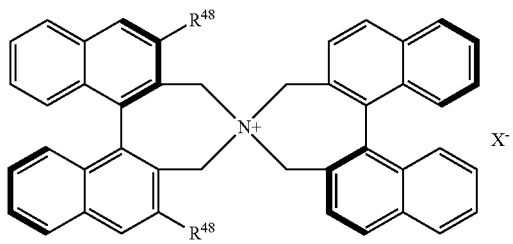
(11)

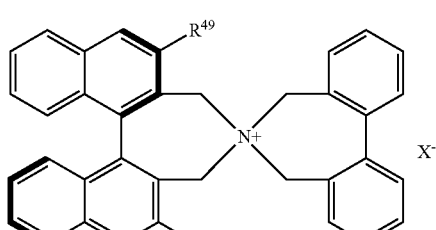
(12)

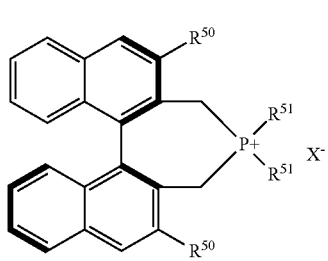
(13)

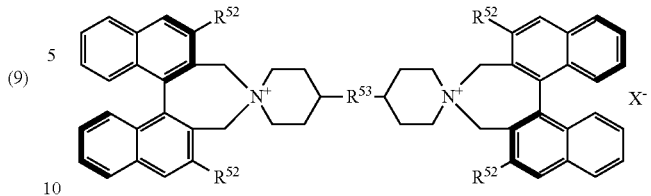
(14)

wherein $R^{48}$, $R^{29}$, $R^{50}$ and $R^{52}$ are each independently phenyl or naphthyl optionally substituted by one to five halogen, $C_1$-$C_4$ alkyl, $C_1$-$C_4$ haloalkyl, $C_1$-$C_4$ alkoxy, $C_1$-$C_4$ haloalkoxy; each $R^{51}$ is $C_1$-$C_5$ alkyl or $C_1$-$C_8$haloalkyl, $R^{53}$ is a bond or $C_1$-$C_8$ alkylene and X is an anion, e.g. a halogen, preferably chlorine or bromine Examples include those wherein each $R^{48}$ is 3,5-(CF$_3$)$_2$(C$_6$H$_3$); each $R^{48}$ is 3,4,5-F$_3$C$_6$H$_2$; each $R^{49}$ is 3,5-(CF$_3$)$_2$(C$_6$H$_3$); each $R^{49}$ is 3,4,5-F$_3$C$_6$H$_2$; each $R^{50}$ is 3,5-(CF$_3$)$_2$(C$_6$H$_3$); each $R^{50}$ is 3,4,5-F$_3$C$_6$H$_2$; each $R^{51}$ is n-butyl; each $R^{52}$ is H and $R^{53}$ is a bond; each $R^{52}$ is H and $R^{53}$ is ethylene; each $R^{52}$ is H and $R^{53}$ is propylene; each $R^{52}$ is phenyl and $R^{53}$ is a bond; each $R^{52}$ is phenyl and $R^{53}$ is ethylene; each $R^{52}$ is phenyl and $R^{53}$ is propylene; each $R^{52}$ is 3,4,5-F$_3$C$_6$H$_2$ and $R^{53}$ is a bond; each $R^{52}$ is 3,4,5-F$_3$C$_6$H$_2$ and $R^{53}$ is ethylene; each $R^{52}$ is 3,4,5-F$_3$C$_6$H$_2$ and $R^{53}$ is propylene; each $R^{52}$ is, 5-(CF$_3$)$_2$C$_6$H$_2$ and $R^{53}$ is a bond; each $R^{52}$ is, 5-(CF$_3$)$_2$C$_6$H$_2$ and $R^{53}$ is ethylene; each $R^{52}$ is 3,5-(CF$_3$)$_2$C$_6$H$_2$ and $R^{53}$ is propylene; each $R^{48}$ is 2-naphthyl as described in M. Hua, H. Cui, L. Wang, J. Nie, J. Ma, *Angew. Chem.* 2010, 122, 2832 and T. Ooi, K. Maruoka, *Acc. Chem. Res.* 2004, 37, 526.

Examples of ligands for galodinium or strontium catalysis (group 13) include compounds of formula 15 and 16

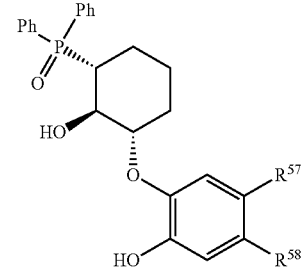
(15)

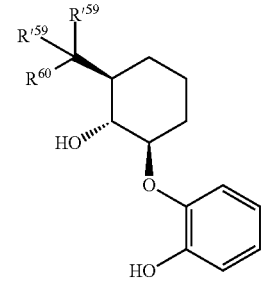
(16)

wherein $R^{57}$ is CN or F, $R^{58}$ is H or F; each $R^{59}$ is phenyl or p-tolyl; $R^{60}$ is OH, OMe or Oi-Bu as described in Tanaka, Y.; Kanai, M.; Shibasaki, M. *J. Am. Chem. Soc.* 2008, 130, 6072; Tanaka, Y.; Kanai, M.; Shibasaki, M. *J. Am. Chem. Soc.* 2010, 132, 8862.

Examples of crown ether phase transfer catalysis (group 14) include compounds of formula XXI

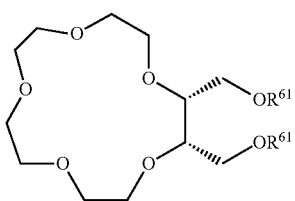

wherein each $R^{61}$ is is H or benzyl as described in Dehmlow, D. E.; Sauerbier, C. Liebigs Ann. Chem. 1989, 181-185.

Examples of ligands for alkaline earth metal catalysis (group 15) include

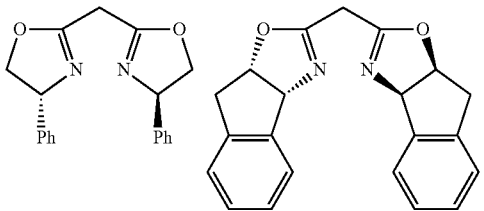

as described in Saito, S.; Tsubogo, T.; Kobayashi, S. J. Am. Chem. Soc. 2007, 129, 5364; Tsubogo, T.; Saibo, S.; Seki, K.; Yamashita, Y.; Kobayashi, S. J. Am. Chem. Soc. 2008, 130, 13321; Kobayashi, S.; Tsubogo, T.; Saito, S.; Yamashita, Y. Org. Lett. 2008, 10, 807

It will be clear to the person skilled in the art that in order to prepare the compounds of the invention with the indicated stereochemistry, the stereochemistry of the compound of formula II must be matched with the corresponding stereochemistry of the catalyst. It is understood that the stereochemistry of the catalysts depicted above is appropriate for a compound of formula IA:

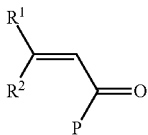

(Ia)

The following schemes describe the processes of the invention in more detail. In the schemes below the stereochemistry at * corresponds to the stereochemistry in the claims. The substituent definitions are as defined herein.

Scheme 1

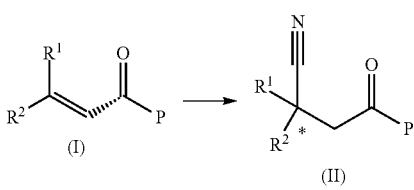

1) Enantioenriched compounds of formula (II) can be prepared by reacting a compound of formula (I) with a suitable cyanide source in the presence of a chiral catalyst. Suitable cyanide sources include, but are not limited to alkali metal cyanides, trimethylsilyl and tert-butyldimethylsilyl cyanides, hydrogen cyanide, $CNCO_2Et$ and acetone cyanohydrin. Depending from the catalyst used, suitable solvents include dioxane, tetrahydrofuran, dichloromethane, t-butylmethyl ether, 1,2-dichloroethane, dimethoxyethane, xylenes and toluene. In certain cases additives such as cesium fluoride, cesium chloride, lithium phenolate or 2,6-dimethylphenol are often required. In most cases it is advantageous to conduct the reaction in a suitable solvent at dilution between 0.1 M to 1 M, preferably 0.3 M to 0.5 M. The reaction temperature could be from −40° C. to 100° C., preferably between −20° C. and 50° C. The reaction time is usually between 1 hour and 96 hours, preferably between 6 hours and 24 hours. The amount of catalyst is usually between 0.02 and 0.2 molar equivalents, preferably between 0.05 and 0.1 molar equivalents. Certain catalysts require a presence of a Lewis acid, such as galodinium trifluoromethansulfonate or strontium trifluoromethanesulfonate. If chiral phase transfer catalysts of group I are used the addition of small amounts of water (between one and four molar equivalents) is often beneficial. Conducting the reaction in a biphasic system (water/suitable organic solvent) is, however, usually detrimental to chemical reactivity. Suitable conditions for this asymmetric reaction are disclosed in the literature: (a) Sammis, G. M.; Jacobsen, E. N. J. Am. Chem. Soc. 2003, 125, 4442. (b) Sammis, G. M.; Danjo, H.; Jacobsen, E. N. J. Am. Chem. Soc. 2004, 126, 9928. (c) Mazet, C.; Jacobsen, E. N. Angew. Chem., Int. Ed. 2008, 47, 1762. (d) Madhavana, N.; Weck, M. AdV. Synth. Catal. 2008, 350, 419. (e) Mita, T.; Sasaki, K.; Kanai, M.; Shibasaki, M. J. Am. Chem. Soc. 2005, 127, 514. (f) Fujimori, I.; Mita, T.; Maki, K.; Shiro, M.; Sato, A.; Furusho, S.; Kanaia, M.; Shibasaki, M. Tetrahedron 2007, 63, 5820. (g) Tanaka, Y.; Kanai, M.; Shibasaki, M. J. Am. Chem. Soc. 2008, 130, 6072. (h) Bernardi, L.; Fini, F.; Fochi, M.; Ricci, A. Synlett 2008, 1857. (i) Jun Wang, Wei Li, Yanling Liu, Yangyang Chu, Lili Lin, Xiaohua Liu, and Xiaoming Feng Organic Letters (2010), 12, (6), 1280-1283. (j) anaka, Yuta; Kanai, Motomu; Shibasaki, Masakatsu, Journal of the American Chemical Society 2010, 132, (26), 8862-8863. (k) Brian A. Provencher, Keith J. Bartelson, Yan Liu, Bruce M. Foxman, Li Deng, Angewandte Chemie International Edition.

Scheme 2

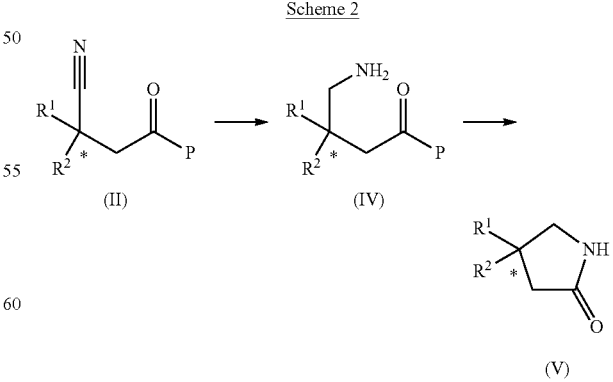

2) Enantioenriched compounds of formula (V) can be prepared by cyclization of enantioenriched compounds of formula (IV) wherein P is hydroxyl, $C_1$-$C_6$alkoxy, N-pyrrolyl, N-azolyl, N-imidazolyl, N-1,2-4-triazolyl, N-benzotriazolyl, $C_1$-$C_6$alkylsulfinyl under standard acidic or basic conditions.

3) Enantioenriched compounds of formula (IV) wherein P is e.g. hydroxyl, $C_1$-$C_6$alkoxy, N-pyrrolyl, N-imidazolyl, N-1,2-4-triazolyl, N-benzotriazolyl, $C_1$-$C_6$alkylsulfinyl can be prepared by selective reduction of enantioenriched compounds of formula (II) wherein P is e.g. hydroxyl, $C_1$-$C_6$alkoxy, N-pyrrolyl, N-imidazolyl, N-1,2-4-triazolyl, N-benzotriazolyl, $C_1$-$C_6$alkylsulfinyl. Suitable reducing agents include iron and zinc in the presence of a strong acid, Raney nickel under the atmosphere of hydrogen, a mixture of titanium (IV) chloride with zinc or titanium (III) chloride and a mixture of cobalt (II) or nickel (II) chloride with sodium borohydride. A reduction with Raney nickel is performed in a suitable alcoholic solvents, such as methanol or ethanol at dilution between 0.1 M to 1 M and in most cases it is advantageous to conduct the reaction between 0.3 M to 0.5 M, at temperatures from 20° C. to 60° C. Hydrogen pressure used is from 1 bar to 20 bars and the amount of catalyst used is between 5 and weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 1 hour. The reduction with cobalt (II) chloride and sodium borohydride is carried out in a suitable alcoholic solvent and the amount of sodium borohydride used is between 2 and 10 molar equivalents, preferably between 2 and 4 molar equivalents, amount of cobalt (II) chloride hexahydrate used is between 1 and 10 molar equivalents. The reaction time is usually between 30 min and 6 hours, preferably between 30 min and 2 hours.

4) Alternatively enantioenriched compounds of formula (V) can be directly obtained by a reductive cyclization of enantioenriched compound of formula (II) under the conditions described above.

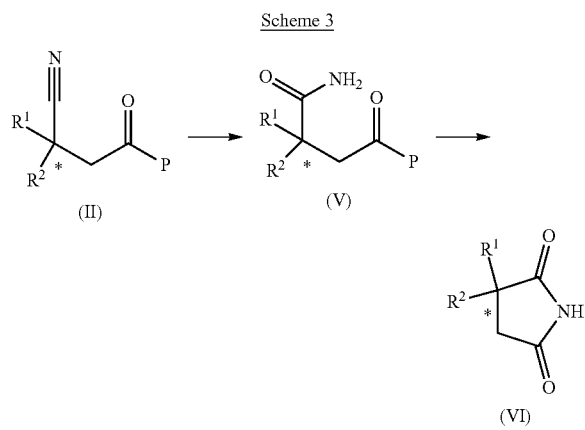

5) Enantioenriched Compounds of formula (VI) can be obtained by a cyclization of enantioenriched compound of formula (V) wherein P is e.g. $C_1$-$C_6$alkoxy, N-pyrrolyl, N-imidazolyl, N-1,2-4-triazolyl, N-benzotriazolyl, $C_1$-$C_6$alkylsulfinyl under basic conditions such as those described in Tetrahedron, 39(19), 3055-7; 1983.

6) Enantioenriched Compounds of formula (V) can be obtained by a selective hydrolysis of the nitrile function in Enantioenriched compounds of formula (II) by acidic or basic hydrolysis.

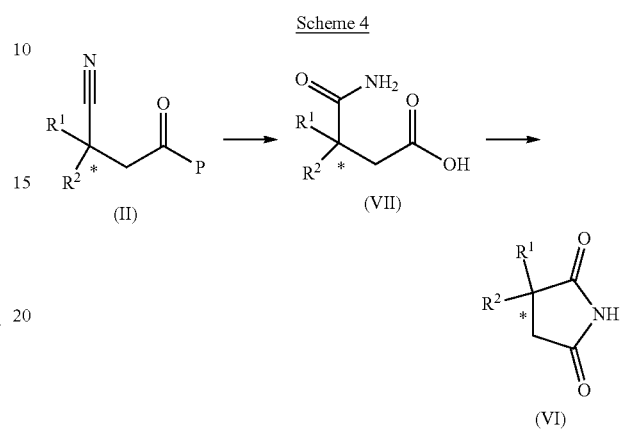

7) Enantioenriched compounds of formula (VI) can be obtained by a cyclization of enantioenriched compounds of formula (VII) by a dehydrating reaction such as those described in Chemistry—A European Journal, 9(14), 3270-3281; 2003.

8) Enantioenriched Compounds of formula (VII) can be obtained by complete hydrolysis of enantioenriched compound of formula (II) under basic aqueous conditions.

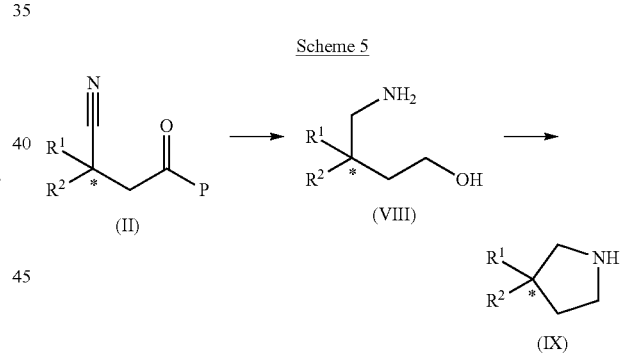

9) Enantioenriched Compounds of formula (IX) can be obtained by treating an enantioenriched compound of formula (II) with an activating agent under the conditions described in J. Org. Chem. 2008, 73, 312-315. Suitable activating agents include sulfonyl molecules e.g. $SOCl_2$ and HCl, trichlorophosphate, triphenylphosphine and diethylazodicarboxylate, 1H-imidazole and bromine and triphenylphosphine, phosphoric acid or catalysts such as dihydridotetrakis(triphenylphosphine)ruthenium(II).

10) Enantioenriched Compounds of formula (VIII) can be obtained by complete reduction of enantioenriched compounds of formula (II) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl for example with a metal hydride such as lithium aluminum hydride ($LiAlH_4$). For instance according to a method developed in the literature in Journal of Medicinal Chemistry, 51(22), 7144-7153; 2008. Alternatively, suitable conditions involve the treatment of Enantioenriched compounds of formula (II) under an atmosphere of hydrogen gas in the presence of a metal catalyst, such as those described in the literature in Bioorganic Chemistry, 36(5), 241-251; 2008.

Scheme 6

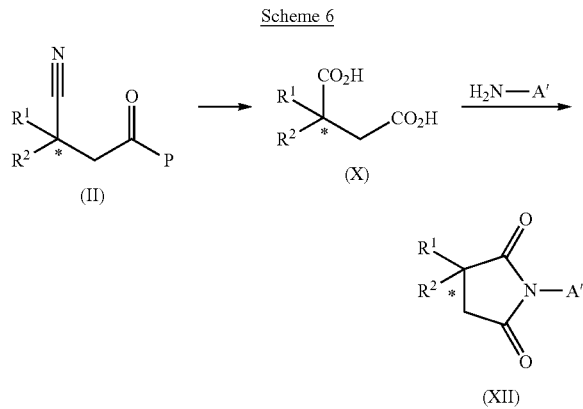

10) Enantioenriched Compounds of formula (XII) can be obtained by reacting a enantioenriched compound of formula (X) and an enantioenriched compound of formula (II) in the presence of a suitable dehydrating agent such as thionyl chloride ($SOCl_2$). For instance according to a method described in Asian Journal of Chemistry, 19(6), 4939-4941; 2007.

11) Enantioenriched Compounds of formula (X) can be obtained by hydrolysis of a enantioenriched compound of formula (II) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl in the presence of aqueous mineral acid, such as aqueous sulphuric acid between 1% and 100% weight/weight, or hydrochloric acid between 1% and 100% weight/weight between 0.1 M to 5 M. In most cases it is advantageous to conduct the reaction preferably 0.3 M to 0.5 M, at temperatures from 20° C. to 120° C.

Scheme 7

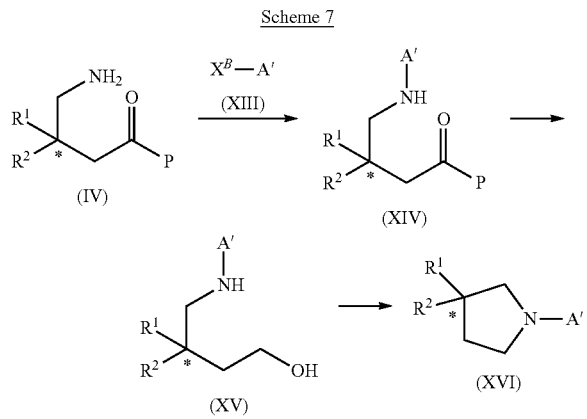

12) Enantioenriched Compounds of formula (XVI) can be obtained by treating a enantioenriched compound of formula (XV) with a suitable activating agent under the conditions described in the literature, such as in J. Org. Chem. 2008, 73, 312-315. Suitable activating agents include sulfonyl molecules e.g. $SOCl_2$, mesylate, tosylate, triflate etc 13) Enantioenriched compounds of formula (XV) can be obtained by reducing an enantioenriched compound of formula (XIV) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl with a suitable metal hydride such as Lithium aluminum hydride, for instance according to a method described in the literature in Journal of Medicinal Chemistry, 49(1), 399-406; 2006.

14) Enantioenriched Compounds of formula (XIV) can be obtained by reacting a enantioenriched compound of formula (IV) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl and a compound of formula (XIII) in the presence of a metal catalyst and a base. Suitable conditions can be found in the literature in Organic Letters, 11(6), 1449-1452; 2009 and in Journal of the American Chemical Society, 132(1), 413-426; 2010.

Scheme 8

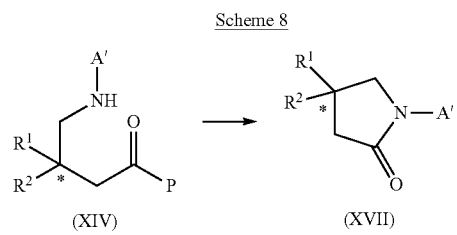

15) Enantioenriched compounds of formula (XVII) can be obtained by cyclising an enantioenriched compound of formula (XIV) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl under neutral conditions, such as those described in the literature in Bioorganic & Medicinal Chemistry Letters, 19(16), 4733-4739; 2009, or under basic conditions such as those described in Synlett, (4), 591-594; 2006.

Scheme 9

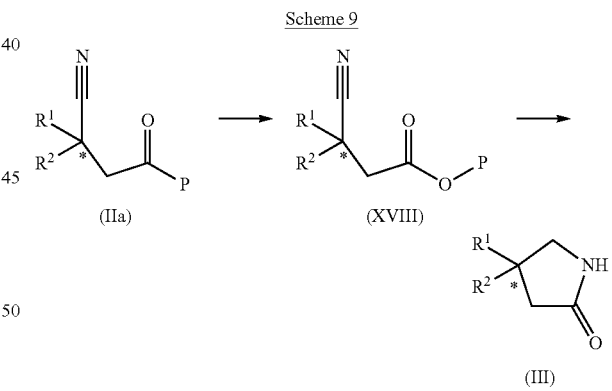

16) Enantioenriched compounds of formula (XVIII) can be obtained by carrying out a Baeyer-Villiger reactions (M. B. Smith, J. March: *March's advanced organic chemistry*. Wiley, New York 2001.) on compounds (IIa) wherein P is e.g. an optionally substituted aryl or an optionally substituted heteroaryl or optionally substituted alkyl. Suitable reagents for the reaction include, but are not limited to m-chloro peroxybenzoic acid and trifluoro peroxyacetic acid. The reaction can be conducted neat or in a suitable solvent such as dichloromethane, chloroform, 1,2-dichloroethane, acetic acid, acetonitrile, methanol, trifluoroacetic acid, 1,4-dioxane, benzene, tert-butyl alcohol. The reaction temperature could be from −50° C. to 150° C., preferably between −20° C. and 100° C. The reaction time is usually between 1 hour and 96 hours, preferably between 1 hour and 24 hours.

17) Enantioenriched compounds of formula (III) could be obtained by reductive cyclization of compounds of formula (XVIII) wherein P is as defined for compounds of formula (IIa). Suitable reducing agents include iron a late transition metal selected from Pd, Pt, Ni and Co and a source of hydride such as hydrogen gas, a borohydride salt or borane. A reduction with Raney nickel is performed in suitable alcoholic solvents, such as methanol or ethanol, at temperatures from 20° C. to 60° C. Hydrogen pressure used is from 1bar to 20 bar and the amount of catalyst used is between 5 and 20 weight percent. The reaction time is usually between 10 min and 6 hours, preferably between 30 min and 2 hours.

Alternatively, the reductive cyclization can be carried out in the presence of a borohydride salt, such as sodium borohydride, in the presence of a cobalt salt, such as cobalt(II) dichloride, in a suitable alcoholic solvent, such as methanol or ethanol, according to the conditions described in the literature Bioorganic & Medicinal Chemistry Letters, 20(2), 704-708; 2010

18) Alternatively the reductive cyclization can be carried out by reacting compounds of formula (XVIII) with borane complexed with a suitable acceptor such as dimethylsulfide or tetrahydrofuran. Suitable solvents induce tetrahydrofuran and 1,4-dioxane and the reaction temperature can range between 25 C and 100 C. Appropriate conditions are described in the literature Journal of the American Chemical Society (1988), 110(6), 1679-90.

Scheme 10

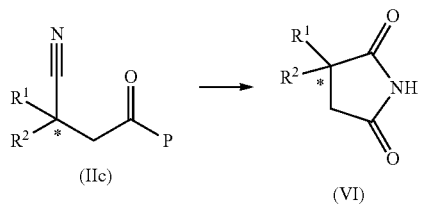

(IIc)          (VI)

19) Enantioenriched Compounds of formula (VI) can be obtained by carrying out a Baeyer-Villiger oxidation reaction on enantioenriched compounds of formula (IIc) wherein P is e.g. an optionally substituted aryl or an optionally substituted heteroaryl. Suitable reagents for the reaction include, but are not limited to m-chloro peroxybenzoic acid, trifluoro peroxyacetic acid and peroxy sulfuric acid. Particularly preferred reagent is peroxysulfuric acid. Between 1 and 100 equivalents of the reagent is typically used (e.g. at least 1 equivalent, e.g. up to 100 equivalents).

Alternatively, a suitable reagent is peroxide in the presence of acid, preferably a strong acid. Peroxides include, but are not limited to hydrogen peroxide, sodium peroxide, sodium perborate, sodium percarbonate, sodium persulfate, potassium persulfate. Particularly preferred is hydrogen peroxide. The concentration of hydrogen peroxide can be between 5% and 90%, preferably between 20-40% (e.g. at least 5%, at least 20%, e.g. up to 90%, up to 40%). (% refers to v/v.). Between 1 and 100 molar equivalents of the reagent is typically used (e.g. at least 1 molar equivalent, e.g. up to 100 molar equivalents).

Strong acids are e.g. any acid with pKa lower then acetic acid. Strong acids include, but are not limited to trifluoroacetic acid, nitrobenzoic acid, methanesulfonic acid, benzenesulfonic acid, p-toluenesulfonic acid, sulfuric acid, Nafion-H. Particularly preferred is sulphuric acid. The concentration of acid, which is preferably sulphuric acid, can be between 10% and 99%, preferably between 50-97% (e.g. at least 10%, at least 50%, e.g. up to 99%, up to 97%) (% refers to v/v.) Between 1 and 100 molar equivalents of the reagent is typically used (e.g. at least 1 molar equivalent, e.g. up to 100 molar equivalents).

The reaction can be conducted neat or in a suitable solvent. Suitable reagents for the reaction include, but are not limited to dichloromethane, dichloroethane, chloroform, carbon tetrachloride, acetic acid. The reaction temperature could be from −50° C. to 150° C., preferably between −20° C. and 100° C. (e.g. at least −50° C., at least −20° C., e.g. up to 150° C., up to 100° C.). The reaction time is usually between 1 hour and 96 hours, preferably between 1 hour and 24 hours (e.g. at least 1 hour, e.g. up to 96 hours, up to 24 hours).

Scheme 11

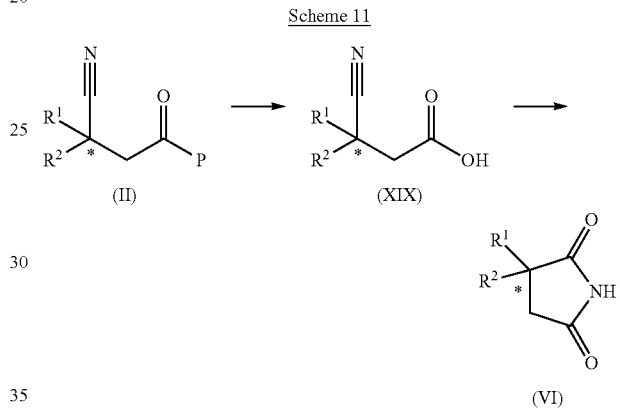

20) Enantioenriched Compounds of formula (VI) can be obtained by hydrolysis of the nitrile function in Enantioenriched compounds of formula (XIX) by acidic or basic hydrolysis followed by a dehydration reaction.

21) Enantioenriched Compounds of formula (XIX) can be obtained by hydrolysis of Enantioenriched compound of formula (II) under basic aqueous conditions.

Scheme 12

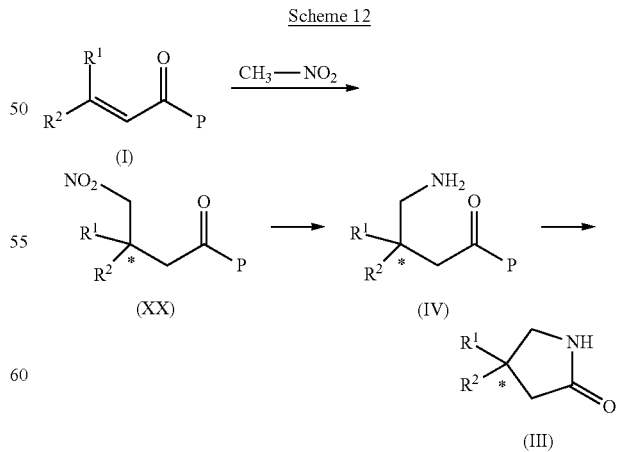

22) Enantioenriched Compounds of formula (III) can be prepared by cyclization of a enantioenriched compound of formula (IV) under basic, acidic or neutral conditions.

23) Enantioenriched Compounds of formula (IV) can be prepared by reducing a enantioenriched compound of formula (XX). Suitable reducing agents include iron and zinc in the presence of a strong acid, a mixture of titanium (IV) chloride with zinc or titanium (III) chloride, or a late transition metal selected from Pd, Pt, Ni and Co and a source of hydride such as hydrogen gas, a silane, formic acid, a formate salt, or a borohydride salt. A reduction with Raney nickel is performed in suitable alcoholic solvents, such as methanol or ethanol, at temperatures from 20° C. to 60° C. Hydrogen pressure used is from 1bar to 20 bar and the amount of catalyst used is between 5 and 20 weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 2 hours.

24) Alternatively, the reduction can be carried out in the presence of a silane, such as triethylsilane, in the presence of a source of palladium, such as palladium supported on charcoal, in a suitable alcoholic solvent, such as methanol or ethanol, according to the conditions described in the literature in Journal of Organic Chemistry, 72(17), 6599-6601; 2007.

25) Alternatively, the reduction can be carried out in the presence of formic acid or a formate salt, such as ammonium formate, in the presence of a source of palladium, such as palladium supported on charcoal, in a suitable alcoholic solvent, such as methanol or ethanol, according to the conditions described in the literature in Synthesis (1986), (2), 133-5 and in Organic Letters, 3, 3153-3155; (2001).

26) Alternatively, the reduction can be carried out in the presence of a borohydride salt, such as sodium borohydride, in the presence of a nickel salt, such as nickel(II) dichloride hexahydrate, in a suitable alcoholic solvent, such as methanol or ethanol, according to the conditions described in the literature in Organic Letters, 3, 1825-1827; (2001).

27) Alternatively, the reduction can be carried out in the presence of a borohydride salt, such as sodium borohydride, in the presence of a cobalt salt, such as cobalt(II) dichloride, in a suitable alcoholic solvent, such as methanol or ethanol, according to the conditions described in the literature in Journal of Organic Chemistry, 62(24), 8565-8568; 1997.

28) Alternatively enantioenriched compounds of formula (III) can be prepared by reducing and cyclizing enantioenriched compounds of formula (XX) under the reduction conditions described above.

29) Enantioenriched compounds of formula (XX) can be prepared by reacting a compound of formula (I) with nitromethane in an asymmetric fashion, in the presence of a chiral catalyst. Reaction with some chiral catalysts, notably bifunctional thiourea or urea catalysts, do not require any additives. The amount of catalyst is usually between 0.02 and 0.2 molar equivalents, preferably between 0.05 and 0.1 molar equivalents. In some instances an additional proton source such as 4-nitrophenol or t-butanol is needed or useful. Such methods have been described in the literature: (a) Benedek Vakulya, Szilárd Varga and Tibor Soós, Journal of Organic Chemistry (2008), 73, (9), 3475-3480. (b) Tetrahedron Letters (2008), 49, (35), 5220-5223. (c) Roberto Ballini, Giovanna Bosica, Dennis Fiorini, Alessandro Palmieri, and Marino Petrini, Chem Rev 2005, 105, 933.

In most other cases, however, it is necessary or useful to add a base to the reaction media. Suitable bases include amines, such as triethylamine, 2,5-dimethylpiperazine, tetramethylpiperidine, 4-dimethylamino pyridine, 1,8-diazabicyclo[5.4.0]undeca-7-ene, metal alkoxides, such as sodium t-butoxide, metal carbonates, such as potassium carbonate or metal fluorides, such as cesium fluoride or cesium chloride and tetrabutylammonium fluoride. In most cases it is advantageous to conduct the reaction using nitromethane as a solvent at dilution between 0.1 M to 1 M, preferably 0.3 M to 0.5 M. Alternatively suitable organic solvents could be used, for example toluene, 1,2-dichloroethane, dichloromethane, tetrahydrofuran, methanol or ethyl acetate at a temperature from 0° C. to 100° C., preferably between 40 and 100° C., and at dilution of e.g. between 0.1 M to 1 M. The reaction time is usually between 12 and 96 hours, preferably between 24 and 72 hours. If a solvent other than nitromethane is used, the amount of nitromethane added is between 1.5 and 20 molar equivalents, preferably between 1.5 and 5 molar equivalents.

Scheme 13

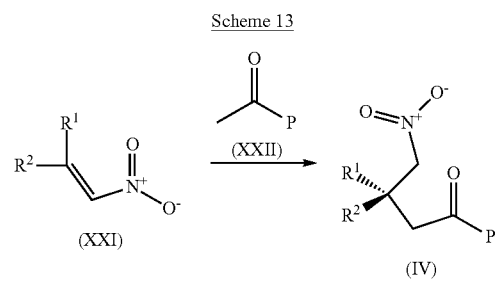

30) Enantioenriched compounds of formula (IV) can be prepared by reacting a compound of formula (XXI) with an acetophenone of formula (XXII) in the presence of a chiral catalyst. Compounds of formula (XXII) are known in the literature or can be prepared using methods known to a person skilled in the art (see for example Journal of the American Chemical Society (2008), 130(42), 13862-13863) and compounds of formula (XXI) are known in the literature or can be prepared using methods known to a person skilled in the art (see for example WO2009/080250). In most cases it is advantageous to conduct the reaction using suitable organic solvents, for example toluene, 1,2-dichloroethane, dichloromethane, tetrahydrofuran, methanol or ethyl acetate. The temperature is usually between 0° C. and 100° C., preferably between 40 and 100° C. Where a solvent is used the reactants are usually at a dilution of e.g. between 0.1 M to 1 M. The reaction time is usually between 1 and 96 hours, preferably between 1 and 24 hours. The amount of catalyst is usually between 0.02 and 0.2 molar equivalents, preferably between 0.05 and 0.1 molar equivalents. Reaction with some chiral catalysts, notably bifunctional thiourea or urea catalysts, do not require any additives. In some cases, however, it is necessary or useful to add an acid to the reaction media. Suitable acids are benzoic acids. In some instances an additional proton source such as 4-nitrophenol, phenols, naphthalenol or t-butanol is needed or useful.

Scheme 14

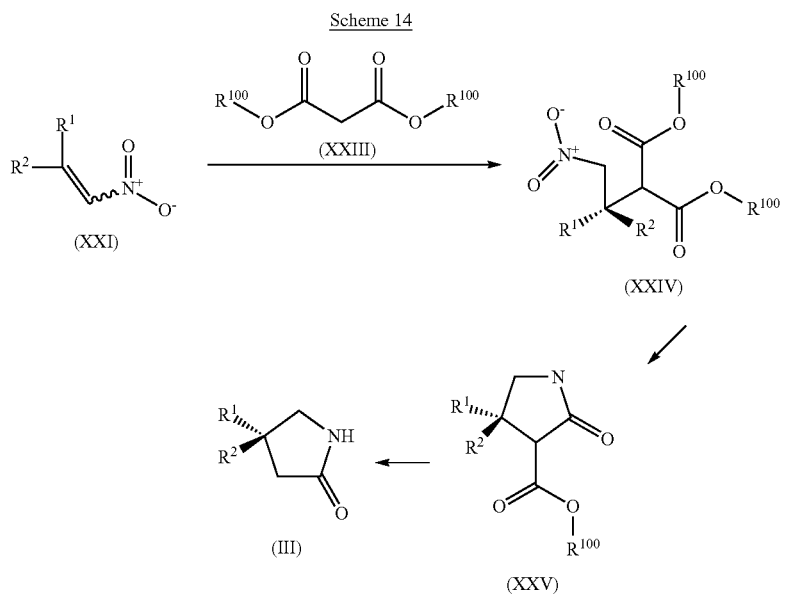

31) Enantioenriched compounds of formula (III) can be prepared by reacting compounds of formula (XXV) with an aqueous base followed by acidification. Suitable bases include but are not limited to alkali metal hydroxides. The reaction temperature could be between 25 C and 100 C, preferably between 40 C and 80 C. Between 1 and 5 equivalents of alkali metal hydroxide are used. Suitable solvents include, but are not limited to alcohols (such as ethanol), water and tetrahydrofuran. Suitable acids include sulphuric acid, hydrochloric acid, phosphoric acid and p-toluene sulfonic acid. In some cases heating in a nonpolar solvent such as toluene is sufficient for decarboxylation.

32) Enantioenriched compounds of formula (XXV) can be prepared by a reductive cyclization of compounds of formula (XXIV). Suitable reducing agents include iron and zinc in the presence of a strong acid, a mixture of titanium (IV) chloride with zinc or titanium (III) chloride, or a late transition metal selected from Pd, Pt, Ni and Co and a source of hydride such as hydrogen gas, a silane, formic acid, a formate salt, or a borohydride salt. A reduction with Raney nickel is performed in suitable alcoholic solvents, such as methanol or ethanol, at temperatures from 20° C. to 60° C. Hydrogen pressure used is from 1bar to 20 bar and the amount of catalyst used is between 5 and 20 weight percent. The reaction time is usually between 10 min and 6 hours, preferably between 30 min and 2 hours. The extent of reduction could potentially be controlled by varying temperature and pressure of hydrogen. A reduction with zinc and acid is carried out in suitable polar solvents, such as dimethylformamide, which are miscible with water. The pH of a solution is kept at 1-2 and the amount of zinc powder used is between 2 and 10 molar equivalents, preferably between 2 and 4 molar equivalents. The reaction time is usually between 30 min and 4 hours, preferably between 30 min and 2 hours. Suitable conditions for similar reductive cyclizations have been describe in the literature, for example: (a) Okino, Tomotaka; Hoashi, Yasutaka; Furukawa, Tomihiro; Xu, Xuenong; Takemoto, Yoshiji. J. Am. Chem. 1 Soc. (2005), 127(1), 119-125; (b) Ji, Jianguo; Barnes, David M.; Zhang, Ji; King, Steven A.; Wittenberger, Steven J.; Morton, Howard E. J. Am. Chem. Soc. (1999), 121(43), 10215-10216

33) Enantioenriched compounds of formula XXIV can be prepared can be prepared by reacting compounds of formula XXI with compounds of formula XXII in the presence of a chiral catalyst. Depending from the catalyst used, suitable solvents include dioxane, tetrahydrofuran, dichloromethane, acetonitrile, t-butylmethyl ether, 1,2-dichloromethane, xylenes and toluene. In most cases it is advantageous to conduct the reaction in a suitable solvent at dilution between 0.1 M to 1 M, preferably 0.3 M to 0.5 M. The reaction temperature could be from −40° C. to 100° C., preferably between −20° C. and 50° C. The reaction time is usually between 1 hour and 96 hours, preferably between 6 hours and 24 hours. The amount of catalyst is usually between 0.02 and 0.2 molar equivalents, preferably between 0.05 and 0.1 molar equivalents.

34) Suitable catalysts and conditions for this asymmetric step are well described in the literature. Representative examples include: (a) Ji, Jianguo; Barnes, David M.; Zhang, Ji; King, Steven A.; Wittenberger, Steven J.; Morton, Howard E. Journal of the American Chemical Society (1999), 121(43), 10215-10216. (b) Cooey, S. H.; Conno, S. J. Angew. Chem. Int. Ed. 2005, 6367. (c) Ye, J.; Dixon, J.; Hynes, P. Chem. Comm 2005, 448

Scheme 15

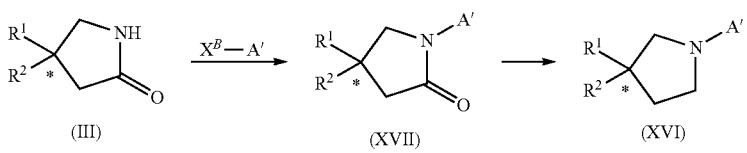

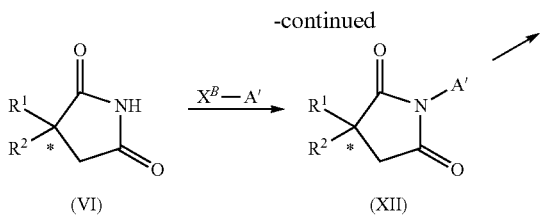

35) Enantioenriched compounds of formula (XVI) can be prepared by reduction of Enantioenriched compounds of formula (XVII) with a metal hydride, for instance according to a method developed in the literature: Journal of Pharmaceutical Sciences (1978), 67(7), 953-6.

36) Enantioenriched Compounds of formula (XVII) can be prepared by reaction of Enantioenriched compound of formula (III) with a compound of formula (Va) wherein $X^B$ is a leaving group, for example a halogen, such as bromo, as described above).

37) Enantioenriched Compounds of formula (XVI) can be prepared by reduction of enantioenriched compounds of formula (XII) with a metal hydride, for instance according to a method developed in the literature (ARKIVOC, 2003, 5, And U.S. Pat. No. 4,524,206).

Suitable reagents for the reaction include, but are not limited to . . . metal hydride The reaction can be conducted neat or in a suitable solvent The reaction temperature could be from −50° C. to 150° C., preferably between −20° C. and 100° C. The reaction time is usually between 1 hour and 96 hours, preferably between 1 hour and 24 hours. The reduction of such succinimides are known to proceed through one or several intermediates of formula (XXVI), (XXVII), and (XXVIII), which may be optionally isolated.

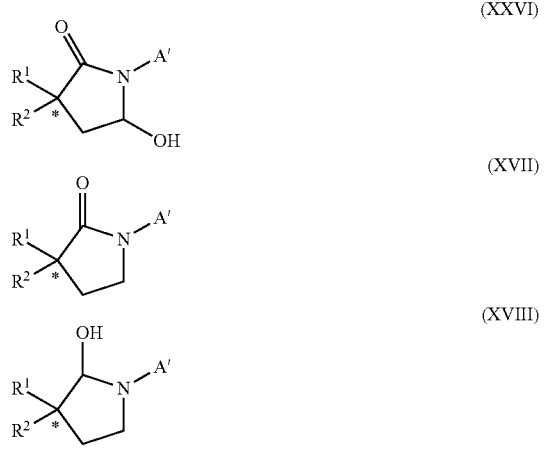

38) Enantioenriched compounds of formula (XI), can be prepared by reaction of enantioenriched compound of formula (XIII) wherein $X^B$ is a leaving group, for example a halogen, such as bromo, with a compound of formula (III) in the absence or the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

Scheme 17

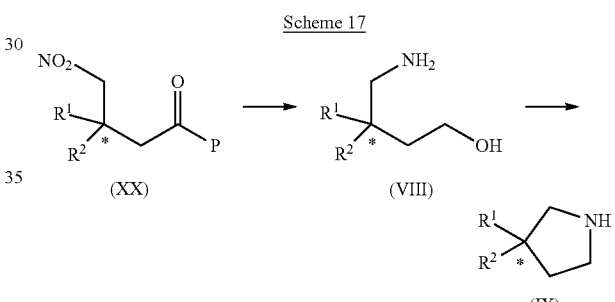

39) Enantioenriched Compounds of formula (VIII) can be obtained by reduction of Enantioenriched compound of formula (XX) wherein P is e.g. $C_1$-$C_6$alkoxy, N-pyrrolyl, N-imidazolyl, N-1,2-4-triazolyl, N-benzotriazolyl or $C_1$-$C_6$alkylsulfinyl using conditions described above.

Scheme 18

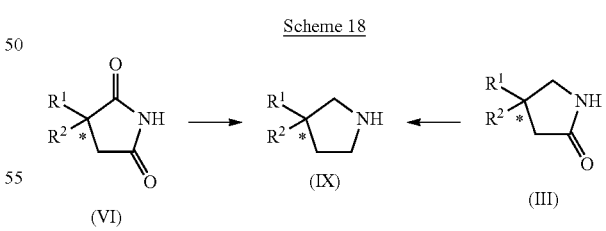

40) Enantioenriched compounds of formula (IX) can be prepared by reduction of Enantioenriched compounds of formula (III) or (VI). Suitable reagents for the reaction include, but are not limited to metal hydride The reaction can be conducted neat or in a suitable solvent. The reaction temperature could be from −50° C. to 150° C., preferably between −20° C. and 100° C. The reaction time is usually between 1 hour and 96 hours, preferably between 1 hour and 24 hours. The reduction of such succinimides are known to proceed through one or several intermediates of formula (XXIX), (XXX), (XXXI), (XXXIII) and ($$), which may be optionally isolated.

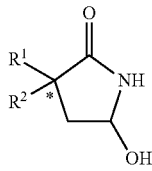
(XXIX)

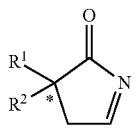
(XXX)

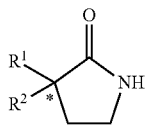
(XXXI)

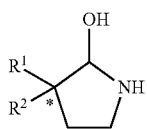
(XXXII)

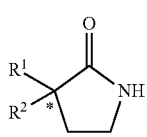
(XXXIII)

Scheme 19

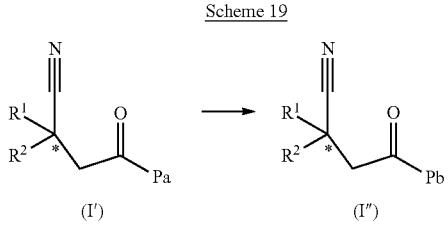

41) Enantioenriched Compounds of formula (I") wherein P is hydroxyl, $C_1$-$C_6$alkoxy, N-pyrrolyl, N-imidazolyl, N-1,2-4-triazolyl, N-benzotriazolyl or $C_1$-$C_6$alkylsulfinyl can be obtained by carrying out a Baeyer-Villiger oxidation reaction on enantioenriched compounds of formula (I') wherein P is an optionally substituted aryl or an optionally substituted heteroaryl. Suitable reagents for the reaction include, but are not limited to m-chloro peroxybenzoic acid, trifluoro peroxyacetic acid and peroxy sulfuric acid. The reaction can be conducted neat or in a suitable solvent. The reaction temperature could be from −50° C. to 150° C., preferably between −20° C. and 100° C. The reaction time is usually between 1 hour and 96 hours, preferably between 1 hour and 24 hours.

In the above schemes a leaving group may before example a halogen, $C_1$-$C_8$alkoxy, $C_1$-$C_8$alkylsulfonyloxy, $C_1$-$C_8$haloalkylsulfonyloxy, $C_1$-$C_5$ arylsulfonyloxy, optionally substituted $C_1$-$C_8$arylsulfonyloxy (aryl is preferably phenyl), diazonium salts (e.g. $X^B$ is $—N_2+Cl^-$, $—N_2^+BF_4^-$, $—N_2^+Br^-$, $—N_2^+PF_6^-$), phosphonate esters (e.g. $—OP(O)(OR)_2$, wherein R is methyl or ethyl), preferably bromo, iodo, chloro, trifluoromethylsulfoxy, p-toluenesulfoxy, diazonium chloride.

In the above schemes, where a reaction condition, e.g. temperature, time, concentration, is given as a range, e.g. value X to value Y, the skilled person will understand that these values serve as guidelines and that it may be possible to perform the reactions outside the given values. In addition, where such ranges are given, in each case these include separate disclosures of "at least X", and "Y or less". For example a range of 50° C. to 150° C. includes s disclosure of "at least 50° C." and a disclosure of "150° C. or less".

The following tables A to M illustrate compounds relating to the invention. In the compounds disclosed in Tables A to M the stereochemistry at * corresponds to that of formula II.

TABLE A

Compounds of formula A

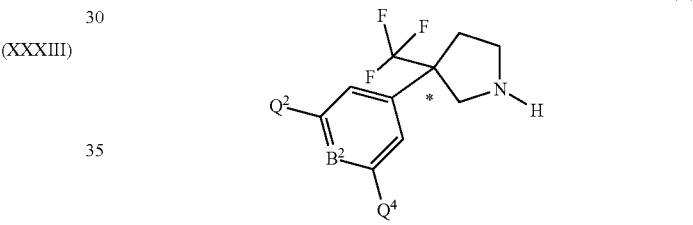
(A)

| Comp No. | Q2 | B2 | Q4 |
|---|---|---|---|
| 1 | Cl | C—Cl | Cl |
| 2 | Cl | C—H | Cl |
| 3 | CF$_3$ | C—H | CF$_3$ |
| 4 | Cl | C—H | CF$_3$ |
| 5 | Br | C—H | CF$_3$ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | CF$_3$ |
| 16 | CF$_3$ | C—Cl | CF$_3$ |
| 17 | CF$_3$ | C—H | H |
| 18 | Cl | N | Cl |
| 19 | Cl | N | H |
| 20 | CF$_3$ | N | CF$_3$ |
| 21 | CF$_3$ | N | H |

TABLE B

Compounds of formula B

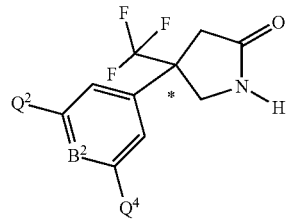
(B)

| Comp No. | Q2 | B2 | Q4 |
|---|---|---|---|
| 1 | Cl | C—Cl | Cl |
| 2 | Cl | C—H | Cl |
| 3 | $CF_3$ | C—H | $CF_3$ |
| 4 | Cl | C—H | $CF_3$ |
| 5 | Br | C—H | $CF_3$ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | $CF_3$ |
| 16 | $CF_3$ | C—Cl | $CF_3$ |
| 17 | $CF_3$ | C—H | H |
| 18 | Cl | N | Cl |
| 19 | Cl | N | H |
| 20 | $CF_3$ | N | $CF_3$ |
| 21 | $CF_3$ | N | H |

TABLE C

Compounds of formula C

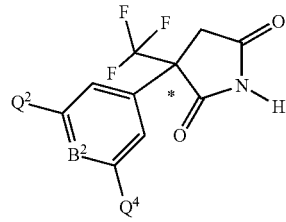
(C)

| Comp No. | Q2 | B2 | Q4 |
|---|---|---|---|
| 1 | Cl | C—Cl | Cl |
| 2 | Cl | C—H | Cl |
| 3 | $CF_3$ | C—H | $CF_3$ |
| 4 | Cl | C—H | $CF_3$ |
| 5 | Br | C—H | $CF_3$ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | $CF_3$ |
| 16 | $CF_3$ | C—Cl | $CF_3$ |
| 17 | $CF_3$ | C—H | H |
| 18 | Cl | N | Cl |
| 19 | Cl | N | H |

TABLE C-continued

Compounds of formula C

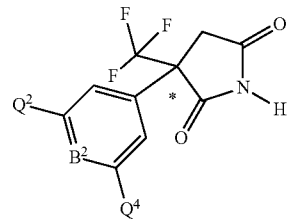
(C)

| Comp No. | Q2 | B2 | Q4 |
|---|---|---|---|
| 20 | $CF_3$ | N | $CF_3$ |
| 21 | $CF_3$ | N | H |

TABLE D

Compounds of formula D

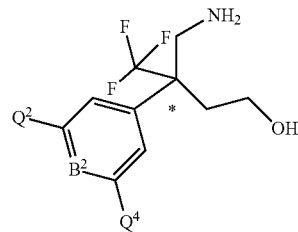
(D)

| Comp No. | Q2 | B2 | Q4 |
|---|---|---|---|
| 1 | Cl | C—Cl | Cl |
| 2 | Cl | C—H | Cl |
| 3 | $CF_3$ | C—H | $CF_3$ |
| 4 | Cl | C—H | $CF_3$ |
| 5 | Br | C—H | $CF_3$ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | $CF_3$ |
| 16 | $CF_3$ | C—Cl | $CF_3$ |
| 17 | $CF_3$ | C—H | H |
| 18 | Cl | N | Cl |
| 19 | Cl | N | H |
| 20 | $CF_3$ | N | $CF_3$ |
| 21 | $CF_3$ | N | H |

TABLE E

Compounds of formula E

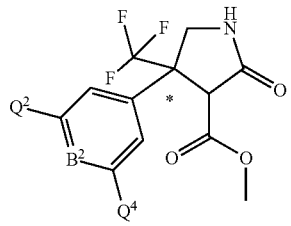
(E)

| Comp No. | Q2 | B2 | Q4 |
|---|---|---|---|
| 1 | Cl | C—Cl | Cl |
| 2 | Cl | C—H | Cl |
| 3 | CF₃ | C—H | CF₃ |
| 4 | Cl | C—H | CF₃ |
| 5 | Br | C—H | CF₃ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | CF₃ |
| 16 | CF₃ | C—Cl | CF₃ |
| 17 | CF₃ | C—H | H |
| 18 | Cl | N | Cl |
| 19 | Cl | N | H |
| 20 | CF₃ | N | CF₃ |
| 21 | CF₃ | N | H |

TABLE F

Compounds of formula F

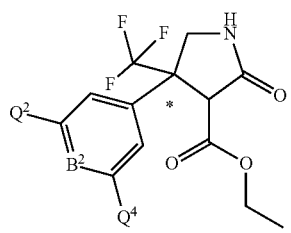
(F)

| Comp No. | Q2 | B2 | Q4 |
|---|---|---|---|
| 1 | Cl | C—Cl | Cl |
| 2 | Cl | C—H | Cl |
| 3 | CF₃ | C—H | CF₃ |
| 4 | Cl | C—H | CF₃ |
| 5 | Br | C—H | CF₃ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | CF₃ |
| 16 | CF₃ | C—Cl | CF₃ |
| 17 | CF₃ | C—H | H |
| 18 | Cl | N | Cl |

TABLE F-continued

Compounds of formula F

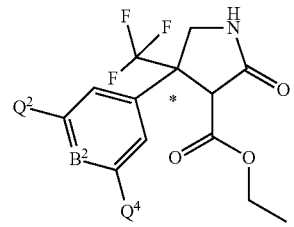
(F)

| Comp No. | Q2 | B2 | Q4 |
|---|---|---|---|
| 19 | Cl | N | H |
| 20 | CF₃ | N | CF₃ |
| 21 | CF₃ | N | H |

TABLE G

Compounds of formula G

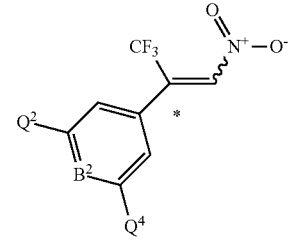
(G)

| Comp No. | Q2 | B2 | Q4 |
|---|---|---|---|
| 1 | Cl | C—Cl | Cl |
| 2 | Cl | C—H | Cl |
| 3 | CF₃ | C—H | CF₃ |
| 4 | Cl | C—H | CF₃ |
| 5 | Br | C—H | CF₃ |
| 6 | Cl | C—F | H |
| 7 | F | C—Cl | H |
| 8 | Cl | C—Cl | H |
| 9 | Cl | C—F | Cl |
| 10 | Cl | C—Br | Cl |
| 11 | Cl | C—I | Cl |
| 12 | F | C—F | F |
| 13 | Cl | C—H | Br |
| 14 | Cl | C—H | F |
| 15 | Cl | C—Cl | CF₃ |
| 16 | CF₃ | C—Cl | CF₃ |
| 17 | CF₃ | C—H | H |
| 18 | Cl | N | Cl |
| 19 | Cl | N | H |
| 20 | CF₃ | N | CF₃ |
| 21 | CF₃ | N | H |

TABLE H

Compounds of formula H

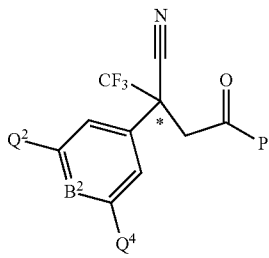

Table H discloses 630 compounds of formula H, wherein $Q^2$, $B^2$, $Q^4$ and P have the values as defined in Table X.

TABLE J

Compounds of formula J

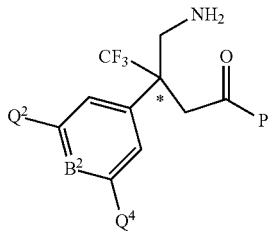

Table J discloses 630 compounds of formula J, wherein $Q^2$, $B^2$, $Q^4$ and P have the values as defined in Table X.

TABLE K

Compounds of formula K

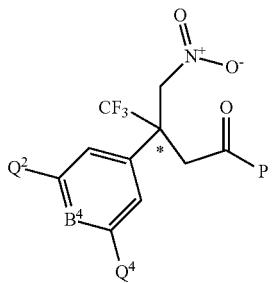

Table K discloses 630 compounds of formula K, wherein $Q^2$, $B^2$, $Q^4$ and P have the values as defined in Table X.

TABLE L

Compounds of formula L

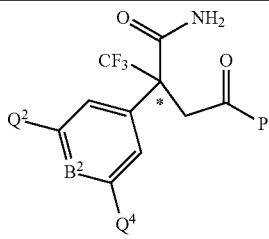

Table L discloses 630 compounds of formula L, wherein $Q^2$, $B^2$, $Q^4$ and P have the values as defined in Table X.

TABLE M

Compounds of formula M

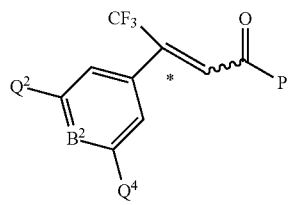

Table M discloses 630 compounds of formula M, wherein $Q^2$, $B^2$, $Q^4$ and P have the values as defined in Table X.

TABLE X

|  | Q2 | B2 | Q4 | P |
|---|---|---|---|---|
| X.1 | Cl | C—Cl | Cl | P1 |
| X.2 | Cl | C—H | Cl | P1 |
| X.3 | CF$_3$ | C—H | CF$_3$ | P1 |
| X.4 | Cl | C—H | CF$_3$ | P1 |
| X.5 | Br | C—H | CF$_3$ | P1 |
| X.6 | Cl | C—F | H | P1 |
| X.7 | F | C—Cl | H | P1 |
| X.8 | Cl | C—Cl | H | P1 |
| X.9 | Cl | C—F | Cl | P1 |
| X.10 | Cl | C—Br | Cl | P1 |
| X.11 | Cl | C—I | Cl | P1 |
| X.12 | F | C—F | F | P1 |
| X.13 | Cl | C—H | Br | P1 |
| X.14 | Cl | C—H | F | P1 |
| X.15 | Cl | C—Cl | CF3 | P1 |
| X.16 | CF3 | C—Cl | CF3 | P1 |
| X.17 | CF3 | C—H | H | P1 |
| X.18 | Cl | C—Cl | Cl | P2 |
| X.19 | Cl | C—H | Cl | P2 |
| X.20 | CF$_3$ | C—H | CF$_3$ | P2 |
| X.21 | Cl | C—H | CF$_3$ | P2 |
| X.22 | Br | C—H | CF$_3$ | P2 |
| X.23 | Cl | C—F | H | P2 |
| X.24 | F | C—Cl | H | P2 |
| X.25 | Cl | C—Cl | H | P2 |
| X.26 | Cl | C—F | Cl | P2 |
| X.27 | Cl | C—Br | Cl | P2 |
| X.28 | Cl | C—I | Cl | P2 |
| X.29 | F | C—F | F | P2 |
| X.30 | Cl | C—H | Br | P2 |
| X.31 | Cl | C—H | F | P2 |
| X.32 | Cl | C—Cl | CF3 | P2 |
| X.33 | CF3 | C—Cl | CF3 | P2 |
| X.34 | CF3 | C—H | H | P2 |
| X.35 | Cl | C—Cl | Cl | P3 |
| X.36 | Cl | C—H | Cl | P3 |
| X.37 | CF$_3$ | C—H | CF$_3$ | P3 |
| X.38 | Cl | C—H | CF$_3$ | P3 |
| X.39 | Br | C—H | CF$_3$ | P3 |
| X.40 | Cl | C—F | H | P3 |
| X.41 | F | C—Cl | H | P3 |
| X.42 | Cl | C—Cl | H | P3 |
| X.43 | Cl | C—F | Cl | P3 |
| X.44 | Cl | C—Br | Cl | P3 |
| X.45 | Cl | C—I | Cl | P3 |
| X.46 | F | C—F | F | P3 |
| X.47 | Cl | C—H | Br | P3 |
| X.48 | Cl | C—H | F | P3 |
| X.49 | Cl | C—Cl | CF3 | P3 |
| X.50 | CF3 | C—Cl | CF3 | P3 |
| X.51 | CF3 | C—H | H | P3 |
| X.52 | Cl | C—Cl | Cl | P4 |
| X.53 | Cl | C—H | Cl | P4 |
| X.54 | CF$_3$ | C—H | CF$_3$ | P4 |
| X.55 | Cl | C—H | CF$_3$ | P4 |

TABLE X-continued

| | Q2 | B2 | Q4 | P |
|---|---|---|---|---|
| X.56 | Br | C—H | CF$_3$ | P4 |
| X.57 | Cl | C—F | H | P4 |
| X.58 | F | C—Cl | H | P4 |
| X.59 | Cl | C—Cl | H | P4 |
| X.60 | Cl | C—F | Cl | P4 |
| X.61 | Cl | C—Br | Cl | P4 |
| X.62 | Cl | C—I | Cl | P4 |
| X.63 | F | C—F | F | P4 |
| X.64 | Cl | C—H | Br | P4 |
| X.65 | Cl | C—H | F | P4 |
| X.66 | Cl | C—Cl | CF3 | P4 |
| X.67 | CF3 | C—Cl | CF3 | P4 |
| X.68 | CF3 | C—H | H | P4 |
| X.69 | Cl | C—Cl | Cl | P5 |
| X.70 | Cl | C—H | Cl | P5 |
| X.71 | CF$_3$ | C—H | CF$_3$ | P5 |
| X.72 | Cl | C—H | CF$_3$ | P5 |
| X.73 | Br | C—H | CF$_3$ | P5 |
| X.74 | Cl | C—F | H | P5 |
| X.75 | F | C—Cl | H | P5 |
| X.76 | Cl | C—Cl | H | P5 |
| X.77 | Cl | C—F | Cl | P5 |
| X.78 | Cl | C—Br | Cl | P5 |
| X.79 | Cl | C—I | Cl | P5 |
| X.80 | F | C—F | F | P5 |
| X.81 | Cl | C—H | Br | P5 |
| X.82 | Cl | C—H | F | P5 |
| X.83 | Cl | C—Cl | CF3 | P5 |
| X.84 | CF3 | C—Cl | CF3 | P5 |
| X.85 | CF3 | C—H | H | P5 |
| X.86 | Cl | C—Cl | Cl | P6 |
| X.87 | Cl | C—H | Cl | P6 |
| X.88 | CF$_3$ | C—H | CF$_3$ | P6 |
| X.89 | Cl | C—H | CF$_3$ | P6 |
| X.90 | Br | C—H | CF$_3$ | P6 |
| X.91 | Cl | C—F | H | P6 |
| X.92 | F | C—Cl | H | P6 |
| X.93 | Cl | C—Cl | H | P6 |
| X.94 | Cl | C—F | Cl | P6 |
| X.95 | Cl | C—Br | Cl | P6 |
| X.96 | Cl | C—I | Cl | P6 |
| X.97 | F | C—F | F | P6 |
| X.98 | Cl | C—H | Br | P6 |
| X.99 | Cl | C—H | F | P6 |
| X.100 | Cl | C—Cl | CF3 | P6 |
| X.101 | CF3 | C—Cl | CF3 | P6 |
| X.102 | CF3 | C—H | H | P6 |
| X.103 | Cl | C—Cl | Cl | P7 |
| X.104 | Cl | C—H | Cl | P7 |
| X.105 | CF$_3$ | C—H | CF$_3$ | P7 |
| X.106 | Cl | C—H | CF$_3$ | P7 |
| X.107 | Br | C—H | CF$_3$ | P7 |
| X.108 | Cl | C—F | H | P7 |
| X.109 | F | C—Cl | H | P7 |
| X.110 | Cl | C—Cl | H | P7 |
| X.111 | Cl | C—F | Cl | P7 |
| X.112 | Cl | C—Br | Cl | P7 |
| X.113 | Cl | C—I | Cl | P7 |
| X.114 | F | C—F | F | P7 |
| X.115 | Cl | C—H | Br | P7 |
| X.116 | Cl | C—H | F | P7 |
| X.117 | Cl | C—Cl | CF3 | P7 |
| X.118 | CF3 | C—Cl | CF3 | P7 |
| X.119 | CF3 | C—H | H | P7 |
| X.120 | Cl | C—Cl | Cl | P8 |
| X.121 | Cl | C—H | Cl | P8 |
| X.122 | CF$_3$ | C—H | CF$_3$ | P8 |
| X.123 | Cl | C—H | CF$_3$ | P8 |
| X.124 | Br | C—H | CF$_3$ | P8 |
| X.125 | Cl | C—F | H | P8 |
| X.126 | F | C—Cl | H | P8 |
| X.127 | Cl | C—Cl | H | P8 |
| X.128 | Cl | C—F | Cl | P8 |
| X.129 | Cl | C—Br | Cl | P8 |
| X.130 | Cl | C—I | Cl | P8 |
| X.131 | F | C—F | F | P8 |
| X.132 | Cl | C—H | Br | P8 |
| X.133 | Cl | C—H | F | P8 |
| X.134 | Cl | C—Cl | CF3 | P8 |
| X.135 | CF3 | C—Cl | CF3 | P8 |
| X.136 | CF3 | C—H | H | P8 |
| X.137 | Cl | C—Cl | Cl | P9 |
| X.138 | Cl | C—H | Cl | P9 |
| X.139 | CF$_3$ | C—H | CF$_3$ | P9 |
| X.140 | Cl | C—H | CF$_3$ | P9 |
| X.141 | Br | C—H | CF$_3$ | P9 |
| X.142 | Cl | C—F | H | P9 |
| X.143 | F | C—Cl | H | P9 |
| X.144 | Cl | C—Cl | H | P9 |
| X.145 | Cl | C—F | Cl | P9 |
| X.146 | Cl | C—Br | Cl | P9 |
| X.147 | Cl | C—I | Cl | P9 |
| X.148 | F | C—F | F | P9 |
| X.149 | Cl | C—H | Br | P9 |
| X.150 | Cl | C—H | F | P9 |
| X.151 | Cl | C—Cl | CF3 | P9 |
| X.152 | CF3 | C—Cl | CF3 | P9 |
| X.153 | CF3 | C—H | H | P9 |
| X.154 | Cl | C—Cl | Cl | P10 |
| X.155 | Cl | C—H | Cl | P10 |
| X.156 | CF$_3$ | C—H | CF$_3$ | P10 |
| X.157 | Cl | C—H | CF$_3$ | P10 |
| X.158 | Br | C—H | CF$_3$ | P10 |
| X.159 | Cl | C—F | H | P10 |
| X.160 | F | C—Cl | H | P10 |
| X.161 | Cl | C—Cl | H | P10 |
| X.162 | Cl | C—F | Cl | P10 |
| X.163 | Cl | C—Br | Cl | P10 |
| X.164 | Cl | C—I | Cl | P10 |
| X.165 | F | C—F | F | P10 |
| X.166 | Cl | C—H | Br | P10 |
| X.167 | Cl | C—H | F | P10 |
| X.168 | Cl | C—Cl | CF3 | P10 |
| X.169 | CF3 | C—Cl | CF3 | P10 |
| X.170 | CF3 | C—H | H | P10 |
| X.171 | Cl | C—Cl | Cl | P11 |
| X.172 | Cl | C—H | Cl | P11 |
| X.173 | CF$_3$ | C—H | CF$_3$ | P11 |
| X.174 | Cl | C—H | CF$_3$ | P11 |
| X.175 | Br | C—H | CF$_3$ | P11 |
| X.176 | Cl | C—F | H | P11 |
| X.177 | F | C—Cl | H | P11 |
| X.178 | Cl | C—Cl | H | P11 |
| X.179 | Cl | C—F | Cl | P11 |
| X.180 | Cl | C—Br | Cl | P11 |
| X.181 | Cl | C—I | Cl | P11 |
| X.182 | F | C—F | F | P11 |
| X.183 | Cl | C—H | Br | P11 |
| X.184 | Cl | C—H | F | P11 |
| X.185 | Cl | C—Cl | CF3 | P11 |
| X.186 | CF3 | C—Cl | CF3 | P11 |
| X.187 | CF3 | C—H | H | P11 |
| X.188 | Cl | C—Cl | Cl | P12 |
| X.187 | Cl | C—H | Cl | P12 |
| X.190 | CF$_3$ | C—H | CF$_3$ | P12 |
| X.191 | Cl | C—H | CF$_3$ | P12 |
| X.192 | Br | C—H | CF$_3$ | P12 |
| X.193 | Cl | C—F | H | P12 |
| X.194 | F | C—Cl | H | P12 |
| X.195 | Cl | C—Cl | H | P12 |
| X.196 | Cl | C—F | Cl | P12 |
| X.197 | Cl | C—Br | Cl | P12 |
| X.198 | Cl | C—I | Cl | P12 |
| X.199 | F | C—F | F | P12 |
| X.200 | Cl | C—H | Br | P12 |
| X.201 | Cl | C—H | F | P12 |
| X.202 | Cl | C—Cl | CF3 | P12 |
| X.203 | CF3 | C—Cl | CF3 | P12 |
| X.204 | CF3 | C—H | H | P12 |
| X.205 | Cl | C—Cl | Cl | P13 |
| X.206 | Cl | C—H | Cl | P13 |
| X.207 | CF$_3$ | C—H | CF$_3$ | P13 |
| X.208 | Cl | C—H | CF$_3$ | P13 |
| X.209 | Br | C—H | CF$_3$ | P13 |
| X.210 | Cl | C—F | H | P13 |
| X.211 | F | C—Cl | H | P13 |

TABLE X-continued

| | Q2 | B2 | Q4 | P |
|---|---|---|---|---|
| X.212 | Cl | C—Cl | H | P13 |
| X.213 | Cl | C—F | Cl | P13 |
| X.214 | Cl | C—Br | Cl | P13 |
| X.215 | Cl | C—I | Cl | P13 |
| X.216 | F | C—F | F | P13 |
| X.217 | Cl | C—H | Br | P13 |
| X.218 | Cl | C—H | F | P13 |
| X.219 | Cl | C—Cl | CF3 | P13 |
| X.220 | CF3 | C—Cl | CF3 | P13 |
| X.221 | CF3 | C—H | H | P13 |
| X.222 | Cl | C—Cl | Cl | P14 |
| X.223 | Cl | C—H | Cl | P14 |
| X.224 | CF$_3$ | C—H | CF$_3$ | P14 |
| X.225 | Cl | C—H | CF$_3$ | P14 |
| X.226 | Br | C—H | CF$_3$ | P14 |
| X.227 | Cl | C—F | H | P14 |
| X.228 | F | C—Cl | H | P14 |
| X.229 | Cl | C—Cl | H | P14 |
| X.230 | Cl | C—F | Cl | P14 |
| X.231 | Cl | C—Br | Cl | P14 |
| X.232 | Cl | C—I | Cl | P14 |
| X.233 | F | C—F | F | P14 |
| X.234 | Cl | C—H | Br | P14 |
| X.235 | Cl | C—H | F | P14 |
| X.236 | Cl | C—Cl | CF3 | P14 |
| X.237 | CF3 | C—Cl | CF3 | P14 |
| X.238 | CF3 | C—H | H | P14 |
| X.239 | Cl | C—Cl | Cl | P15 |
| X.240 | Cl | C—H | Cl | P15 |
| X.241 | CF$_3$ | C—H | CF$_3$ | P15 |
| X.242 | Cl | C—H | CF$_3$ | P15 |
| X.243 | Br | C—H | CF$_3$ | P15 |
| X.244 | Cl | C—F | H | P15 |
| X.245 | F | C—Cl | H | P15 |
| X.246 | Cl | C—Cl | H | P15 |
| X.247 | Cl | C—F | Cl | P15 |
| X.248 | Cl | C—Br | Cl | P15 |
| X.249 | Cl | C—I | Cl | P15 |
| X.250 | F | C—F | F | P15 |
| X.251 | Cl | C—H | Br | P15 |
| X.252 | Cl | C—H | F | P15 |
| X.253 | Cl | C—Cl | CF3 | P15 |
| X.254 | CF3 | C—Cl | CF3 | P15 |
| X.255 | CF3 | C—H | H | P15 |
| X.256 | Cl | C—Cl | Cl | P16 |
| X.257 | Cl | C—H | Cl | P16 |
| X.258 | CF$_3$ | C—H | CF$_3$ | P16 |
| X.259 | Cl | C—H | CF$_3$ | P16 |
| X.260 | Br | C—H | CF$_3$ | P16 |
| X.261 | Cl | C—F | H | P16 |
| X.262 | F | C—Cl | H | P16 |
| X.263 | Cl | C—Cl | H | P16 |
| X.264 | Cl | C—F | Cl | P16 |
| X.265 | Cl | C—Br | Cl | P16 |
| X.266 | Cl | C—I | Cl | P16 |
| X.267 | F | C—F | F | P16 |
| X.268 | Cl | C—H | Br | P16 |
| X.269 | Cl | C—H | F | P16 |
| X.270 | Cl | C—Cl | CF3 | P16 |
| X.271 | CF3 | C—Cl | CF3 | P16 |
| X.272 | CF3 | C—H | H | P16 |
| X.273 | Cl | C—Cl | Cl | P17 |
| X.274 | Cl | C—H | Cl | P17 |
| X.275 | CF$_3$ | C—H | CF$_3$ | P17 |
| X.276 | Cl | C—H | CF$_3$ | P17 |
| X.277 | Br | C—H | CF$_3$ | P17 |
| X.278 | Cl | C—F | H | P17 |
| X.279 | F | C—Cl | H | P17 |
| X.280 | Cl | C—Cl | H | P17 |
| X.281 | Cl | C—F | Cl | P17 |
| X.282 | Cl | C—Br | Cl | P17 |
| X.283 | Cl | C—I | Cl | P17 |
| X.284 | F | C—F | F | P17 |
| X.285 | Cl | C—H | Br | P17 |
| X.286 | Cl | C—H | F | P17 |
| X.287 | Cl | C—Cl | CF3 | P17 |
| X.288 | CF3 | C—Cl | CF3 | P17 |
| X.289 | CF3 | C—H | H | P17 |
| X.290 | Cl | C—Cl | Cl | P18 |
| X.291 | Cl | C—H | Cl | P18 |
| X.292 | CF$_3$ | C—H | CF$_3$ | P18 |
| X.293 | Cl | C—H | CF$_3$ | P18 |
| X.294 | Br | C—H | CF$_3$ | P18 |
| X.295 | Cl | C—F | H | P18 |
| X.296 | F | C—Cl | H | P18 |
| X.297 | Cl | C—Cl | H | P18 |
| X.298 | Cl | C—F | Cl | P18 |
| X.299 | Cl | C—Br | Cl | P18 |
| X.300 | Cl | C—I | Cl | P18 |
| X.301 | F | C—F | F | P18 |
| X.302 | Cl | C—H | Br | P18 |
| X.303 | Cl | C—H | F | P18 |
| X.304 | Cl | C—Cl | CF3 | P18 |
| X.305 | CF3 | C—Cl | CF3 | P18 |
| X.306 | CF3 | C—H | H | P18 |
| X.307 | Cl | C—Cl | Cl | P19 |
| X.308 | Cl | C—H | Cl | P19 |
| X.309 | CF$_3$ | C—H | CF$_3$ | P19 |
| X.310 | Cl | C—H | CF$_3$ | P19 |
| X.311 | Br | C—H | CF$_3$ | P19 |
| X.312 | Cl | C—F | H | P19 |
| X.313 | F | C—Cl | H | P19 |
| X.314 | Cl | C—Cl | H | P19 |
| X.315 | Cl | C—F | Cl | P19 |
| X.316 | Cl | C—Br | Cl | P19 |
| X.317 | Cl | C—I | Cl | P19 |
| X.318 | F | C—F | F | P19 |
| X.319 | Cl | C—H | Br | P19 |
| X.320 | Cl | C—H | F | P19 |
| X.321 | Cl | C—Cl | CF3 | P19 |
| X.322 | CF3 | C—Cl | CF3 | P19 |
| X.323 | CF3 | C—H | H | P19 |
| X.324 | Cl | C—Cl | Cl | P20 |
| X.325 | Cl | C—H | Cl | P20 |
| X.326 | CF$_3$ | C—H | CF$_3$ | P20 |
| X.327 | Cl | C—H | CF$_3$ | P20 |
| X.328 | Br | C—H | CF$_3$ | P20 |
| X.329 | Cl | C—F | H | P20 |
| X.330 | F | C—Cl | H | P20 |
| X.331 | Cl | C—Cl | H | P20 |
| X.332 | Cl | C—F | Cl | P20 |
| X.333 | Cl | C—Br | Cl | P20 |
| X.334 | Cl | C—I | Cl | P20 |
| X.335 | F | C—F | F | P20 |
| X.336 | Cl | C—H | Br | P20 |
| X.337 | Cl | C—H | F | P20 |
| X.338 | Cl | C—Cl | CF3 | P20 |
| X.339 | CF3 | C—Cl | CF3 | P20 |
| X.340 | CF3 | C—H | H | P20 |
| X.341 | Cl | C—Cl | Cl | P21 |
| X.342 | Cl | C—H | Cl | P21 |
| X.343 | CF$_3$ | C—H | CF$_3$ | P21 |
| X.344 | Cl | C—H | CF$_3$ | P21 |
| X.345 | Br | C—H | CF$_3$ | P21 |
| X.346 | Cl | C—F | H | P21 |
| X.347 | F | C—Cl | H | P21 |
| X.348 | Cl | C—Cl | H | P21 |
| X.349 | Cl | C—F | Cl | P21 |
| X.350 | Cl | C—Br | Cl | P21 |
| X.351 | Cl | C—I | Cl | P21 |
| X.352 | F | C—F | F | P21 |
| X.353 | Cl | C—H | Br | P21 |
| X.354 | Cl | C—H | F | P21 |
| X.355 | Cl | C—Cl | CF3 | P21 |
| X.356 | CF3 | C—Cl | CF3 | P21 |
| X.357 | CF3 | C—H | H | P21 |
| X.358 | Cl | C—Cl | Cl | P22 |
| X.359 | Cl | C—H | Cl | P22 |
| X.360 | CF$_3$ | C—H | CF$_3$ | P22 |
| X.361 | Cl | C—H | CF$_3$ | P22 |
| X.362 | Br | C—H | CF$_3$ | P22 |
| X.363 | Cl | C—F | H | P22 |
| X.364 | F | C—Cl | H | P22 |
| X.365 | Cl | C—Cl | H | P22 |
| X.366 | Cl | C—F | Cl | P22 |
| X.367 | Cl | C—Br | Cl | P22 |

TABLE X-continued

| | Q2 | B2 | Q4 | P |
|---|---|---|---|---|
| X.368 | Cl | C—I | Cl | P22 |
| X.369 | F | C—F | F | P22 |
| X.370 | Cl | C—H | Br | P22 |
| X.371 | Cl | C—H | F | P22 |
| X.372 | Cl | C—Cl | CF3 | P22 |
| X.373 | CF3 | C—Cl | CF3 | P22 |
| X.374 | CF3 | C—H | H | P22 |
| X.375 | Cl | C—Cl | Cl | P23 |
| X.376 | Cl | C—H | Cl | P23 |
| X.377 | CF$_3$ | C—H | CF$_3$ | P23 |
| X.378 | Cl | C—H | CF$_3$ | P23 |
| X.379 | Br | C—H | CF$_3$ | P23 |
| X.380 | Cl | C—F | H | P23 |
| X.381 | F | C—Cl | H | P23 |
| X.382 | Cl | C—Cl | H | P23 |
| X.383 | Cl | C—F | Cl | P23 |
| X.384 | Cl | C—Br | Cl | P23 |
| X.385 | Cl | C—I | Cl | P23 |
| X.386 | F | C—F | F | P23 |
| X.387 | Cl | C—H | Br | P23 |
| X.388 | Cl | C—H | F | P23 |
| X.389 | Cl | C—Cl | CF3 | P23 |
| X.390 | CF3 | C—Cl | CF3 | P23 |
| X.391 | CF3 | C—H | H | P23 |
| X.392 | Cl | C—Cl | Cl | P24 |
| X.393 | Cl | C—H | Cl | P24 |
| X.394 | CF$_3$ | C—H | CF$_3$ | P24 |
| X.395 | Cl | C—H | CF$_3$ | P24 |
| X.396 | Br | C—H | CF$_3$ | P24 |
| X.397 | Cl | C—F | H | P24 |
| X.398 | F | C—Cl | H | P24 |
| X.399 | Cl | C—Cl | H | P24 |
| X.400 | Cl | C—F | Cl | P24 |
| X.401 | Cl | C—Br | Cl | P24 |
| X.402 | Cl | C—I | Cl | P24 |
| X.403 | F | C—F | F | P24 |
| X.404 | Cl | C—H | Br | P24 |
| X.405 | Cl | C—H | F | P24 |
| X.406 | Cl | C—Cl | CF3 | P24 |
| X.407 | CF3 | C—Cl | CF3 | P24 |
| X.408 | CF3 | C—H | H | P24 |
| X.409 | Cl | C—Cl | Cl | P25 |
| X.410 | Cl | C—H | Cl | P25 |
| X.411 | CF$_3$ | C—H | CF$_3$ | P25 |
| X.412 | Cl | C—H | CF$_3$ | P25 |
| X.413 | Br | C—H | CF$_3$ | P25 |
| X.414 | Cl | C—F | H | P25 |
| X.415 | F | C—Cl | H | P25 |
| X.416 | Cl | C—Cl | H | P25 |
| X.417 | Cl | C—F | Cl | P25 |
| X.418 | Cl | C—Br | Cl | P25 |
| X.419 | Cl | C—I | Cl | P25 |
| X.420 | F | C—F | F | P25 |
| X.421 | Cl | C—H | Br | P25 |
| X.422 | Cl | C—H | F | P25 |
| X.423 | Cl | C—Cl | CF3 | P25 |
| X.424 | CF3 | C—Cl | CF3 | P25 |
| X.425 | CF3 | C—H | H | P25 |
| X.426 | Cl | C—Cl | Cl | P26 |
| X.427 | Cl | C—H | Cl | P26 |
| X.428 | CF$_3$ | C—H | CF$_3$ | P26 |
| X.429 | Cl | C—H | CF$_3$ | P26 |
| X.430 | Br | C—H | CF$_3$ | P26 |
| X.431 | Cl | C—F | H | P26 |
| X.432 | F | C—Cl | H | P26 |
| X.433 | Cl | C—Cl | H | P26 |
| X.434 | Cl | C—F | Cl | P26 |
| X.435 | Cl | C—Br | Cl | P26 |
| X.436 | Cl | C—I | Cl | P26 |
| X.437 | F | C—F | F | P26 |
| X.438 | Cl | C—H | Br | P26 |
| X.439 | Cl | C—H | F | P26 |
| X.440 | Cl | C—Cl | CF3 | P26 |
| X.441 | CF3 | C—Cl | CF3 | P26 |
| X.442 | CF3 | C—H | H | P26 |
| X.443 | Cl | C—Cl | Cl | P27 |
| X.444 | Cl | C—H | Cl | P27 |
| X.445 | CF$_3$ | C—H | CF$_3$ | P27 |
| X.446 | Cl | C—H | CF$_3$ | P27 |
| X.447 | Br | C—H | CF$_3$ | P27 |
| X.448 | Cl | C—F | H | P27 |
| X.449 | F | C—Cl | H | P27 |
| X.450 | Cl | C—Cl | H | P27 |
| X.451 | Cl | C—F | Cl | P27 |
| X.452 | Cl | C—Br | Cl | P27 |
| X.453 | Cl | C—I | Cl | P27 |
| X.454 | F | C—F | F | P27 |
| X.455 | Cl | C—H | Br | P27 |
| X.456 | Cl | C—H | F | P27 |
| X.457 | Cl | C—Cl | CF3 | P27 |
| X.458 | CF3 | C—Cl | CF3 | P27 |
| X.459 | CF3 | C—H | H | P27 |
| X.460 | Cl | C—Cl | Cl | P28 |
| X.461 | Cl | C—H | Cl | P28 |
| X.462 | CF$_3$ | C—H | CF$_3$ | P28 |
| X.463 | Cl | C—H | CF$_3$ | P28 |
| X.464 | Br | C—H | CF$_3$ | P28 |
| X.465 | Cl | C—F | H | P28 |
| X.466 | F | C—Cl | H | P28 |
| X.467 | Cl | C—Cl | H | P28 |
| X.468 | Cl | C—F | Cl | P28 |
| X.469 | Cl | C—Br | Cl | P28 |
| X.470 | Cl | C—I | Cl | P28 |
| X.471 | F | C—F | F | P28 |
| X.472 | Cl | C—H | Br | P28 |
| X.473 | Cl | C—H | F | P28 |
| X.474 | Cl | C—Cl | CF3 | P28 |
| X.475 | CF3 | C—Cl | CF3 | P28 |
| X.476 | CF3 | C—H | H | P28 |
| X.477 | Cl | C—Cl | Cl | P29 |
| X.478 | Cl | C—H | Cl | P29 |
| X.479 | CF$_3$ | C—H | CF$_3$ | P29 |
| X.480 | Cl | C—H | CF$_3$ | P29 |
| X.481 | Br | C—H | CF$_3$ | P29 |
| X.482 | Cl | C—F | H | P29 |
| X.483 | F | C—Cl | H | P29 |
| X.484 | Cl | C—Cl | H | P29 |
| X.485 | Cl | C—F | Cl | P29 |
| X.486 | Cl | C—Br | Cl | P29 |
| X.487 | Cl | C—I | Cl | P29 |
| X.488 | F | C—F | F | P29 |
| X.489 | Cl | C—H | Br | P29 |
| X.490 | Cl | C—H | F | P29 |
| X.491 | Cl | C—Cl | CF3 | P29 |
| X.492 | CF3 | C—Cl | CF3 | P29 |
| X.493 | CF3 | C—H | H | P29 |
| X.494 | Cl | C—Cl | Cl | P30 |
| X.495 | Cl | C—H | Cl | P30 |
| X.496 | CF$_3$ | C—H | CF$_3$ | P30 |
| X.497 | Cl | C—H | CF$_3$ | P30 |
| X.498 | Br | C—H | CF$_3$ | P30 |
| X.499 | Cl | C—F | H | P30 |
| X.500 | F | C—Cl | H | P30 |
| X.501 | Cl | C—Cl | H | P30 |
| X.502 | Cl | C—F | Cl | P30 |
| X.503 | Cl | C—Br | Cl | P30 |
| X.504 | Cl | C—I | Cl | P30 |
| X.505 | F | C—F | F | P30 |
| X.506 | Cl | C—H | Br | P30 |
| X.507 | Cl | C—H | F | P30 |
| X.508 | Cl | C—Cl | CF3 | P30 |
| X.509 | CF3 | C—Cl | CF3 | P30 |
| X.510 | CF3 | C—H | H | P30 |
| X.511 | Cl | N | Cl | P1 |
| X.512 | Cl | N | H | P1 |
| X.513 | CF$_3$ | N | CF$_3$ | P1 |
| X.514 | CF$_3$ | N | H | P1 |
| X.515 | Cl | N | Cl | P2 |
| X.516 | Cl | N | H | P2 |
| X.517 | CF3 | N | CF3 | P2 |
| X.518 | CF3 | N | H | P2 |
| X.519 | Cl | N | Cl | P3 |
| X.520 | Cl | N | H | P3 |
| X.521 | CF3 | N | CF3 | P3 |
| X.522 | CF3 | N | H | P3 |
| X.523 | Cl | N | Cl | P4 |

TABLE X-continued

| | Q2 | B2 | Q4 | P |
|---|---|---|---|---|
| X.524 | Cl | N | H | P4 |
| X.525 | CF3 | N | CF3 | P4 |
| X.526 | CF3 | N | H | P4 |
| X.527 | Cl | N | Cl | P5 |
| X.528 | Cl | N | H | P5 |
| X.529 | CF3 | N | CF3 | P5 |
| X.530 | CF3 | N | H | P5 |
| X.531 | Cl | N | Cl | P6 |
| X.532 | Cl | N | H | P6 |
| X.533 | CF3 | N | CF3 | P6 |
| X.534 | CF3 | N | H | P6 |
| X.535 | Cl | N | Cl | P7 |
| X.536 | Cl | N | H | P7 |
| X.537 | CF3 | N | CF3 | P7 |
| X.538 | CF3 | N | H | P7 |
| X.539 | Cl | N | Cl | P8 |
| X.540 | Cl | N | H | P8 |
| X.541 | CF3 | N | CF3 | P8 |
| X.542 | CF3 | N | H | P8 |
| X.543 | Cl | N | Cl | P9 |
| X.544 | Cl | N | H | P9 |
| X.545 | CF3 | N | CF3 | P9 |
| X.546 | CF3 | N | H | P9 |
| X.547 | Cl | N | Cl | P10 |
| X.548 | Cl | N | H | P10 |
| X.549 | CF3 | N | CF3 | P10 |
| X.550 | CF3 | N | H | P10 |
| X.551 | Cl | N | Cl | P11 |
| X.552 | Cl | N | H | P11 |
| X.553 | CF3 | N | CF3 | P11 |
| X.554 | CF3 | N | H | P11 |
| X.555 | Cl | N | Cl | P12 |
| X.556 | Cl | N | H | P12 |
| X.557 | CF3 | N | CF3 | P12 |
| X.558 | CF3 | N | H | P12 |
| X.559 | Cl | N | Cl | P13 |
| X.560 | Cl | N | H | P13 |
| X.561 | CF3 | N | CF3 | P13 |
| X.562 | CF3 | N | H | P13 |
| X.563 | Cl | N | Cl | P14 |
| X.564 | Cl | N | H | P14 |
| X.565 | CF3 | N | CF3 | P14 |
| X.566 | CF3 | N | H | P14 |
| X.567 | Cl | N | Cl | P15 |
| X.568 | Cl | N | H | P15 |
| X.569 | CF3 | N | CF3 | P15 |
| X.570 | CF3 | N | H | P15 |
| X.571 | Cl | N | Cl | P16 |
| X.572 | Cl | N | H | P16 |
| X.573 | CF3 | N | CF3 | P16 |
| X.574 | CF3 | N | H | P16 |
| X.575 | Cl | N | Cl | P17 |
| X.576 | Cl | N | H | P17 |
| X.577 | CF3 | N | CF3 | P17 |
| X.578 | CF3 | N | H | P17 |
| X.579 | Cl | N | Cl | P18 |
| X.580 | Cl | N | H | P18 |
| X.581 | CF3 | N | CF3 | P18 |
| X.582 | CF3 | N | H | P18 |
| X.583 | Cl | N | Cl | P19 |
| X.584 | Cl | N | H | P19 |
| X.585 | CF3 | N | CF3 | P19 |
| X.586 | CF3 | N | H | P19 |
| X.587 | Cl | N | Cl | P20 |
| X.588 | Cl | N | H | P20 |
| X.589 | CF3 | N | CF3 | P20 |
| X.590 | CF3 | N | H | P20 |
| X.591 | Cl | N | Cl | P21 |
| X.592 | Cl | N | H | P21 |
| X.593 | CF3 | N | CF3 | P21 |
| X.594 | CF3 | N | H | P21 |
| X.595 | Cl | N | Cl | P22 |
| X.596 | Cl | N | H | P22 |
| X.597 | CF3 | N | CF3 | P22 |
| X.598 | CF3 | N | H | P22 |
| X.599 | Cl | N | Cl | P23 |
| X.600 | Cl | N | H | P23 |
| X.601 | CF3 | N | CF3 | P23 |
| X.602 | CF3 | N | H | P23 |
| X.603 | Cl | N | Cl | P24 |
| X.604 | Cl | N | H | P24 |
| X.605 | CF3 | N | CF3 | P24 |
| X.606 | CF3 | N | H | P24 |
| X.607 | Cl | N | Cl | P25 |
| X.608 | Cl | N | H | P25 |
| X.609 | CF3 | N | CF3 | P25 |
| X.610 | CF3 | N | H | P25 |
| X.611 | Cl | N | Cl | P26 |
| X.612 | Cl | N | H | P26 |
| X.613 | CF3 | N | CF3 | P26 |
| X.614 | CF3 | N | H | P26 |
| X.615 | Cl | N | Cl | P27 |
| X.616 | Cl | N | H | P27 |
| X.617 | CF3 | N | CF3 | P27 |
| X.618 | CF3 | N | H | P27 |
| X.619 | Cl | N | Cl | P28 |
| X.620 | Cl | N | H | P28 |
| X.621 | CF3 | N | CF3 | P28 |
| X.622 | CF3 | N | H | P28 |
| X.623 | Cl | N | Cl | P29 |
| X.624 | Cl | N | H | P29 |
| X.625 | CF3 | N | CF3 | P29 |
| X.626 | CF3 | N | H | P29 |
| X.627 | Cl | N | Cl | P30 |
| X.628 | Cl | N | H | P30 |
| X.629 | CF3 | N | CF3 | P30 |
| X.630 | CF3 | N | H | P30 |

The values of P1 to P30 in Table X are shown in Table P.

TABLE P

| P1 | —OCH₃ |
|---|---|
| P2 | —OCH₂CH₃ |
| P3 | —OtBu |
| P4 | —NMe₂ |
| P5 |  |
| P6 | 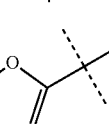 |
| P7 | 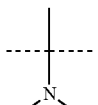 |
| P8 | 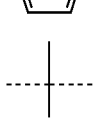 |

TABLE P-continued
| | |
|---|---|
| P9 | 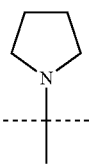 |
| P10 | OPh |
| P11 | Ph |
| P12 | 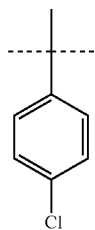 |
| P13 | 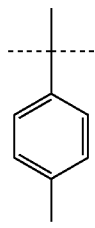 |
| P14 | 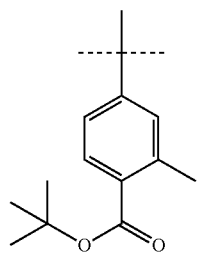 |
| P15 | tBu |
| P16 | 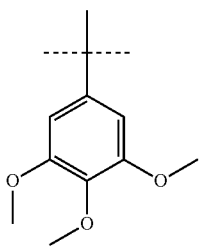 |
| P17 | 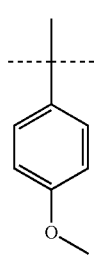 |
TABLE P-continued
| | |
|---|---|
| P18 | 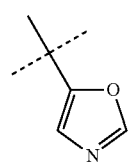 |
| P19 | |
| P20 | |
| P21 | |
| P22 | |
| P23 | |
| P24 | |
| P25 | —CH(CH₃)₂ |

TABLE P-continued

| | |
|---|---|
| P26 | 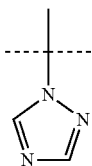 |
| P27 | 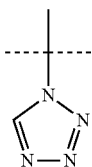 |
| P28 | 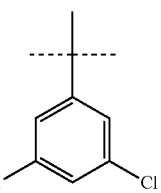 |
| P29 | OCH$_2$Ph |
| P30 | OH |

(P29 and P30 share the structure: 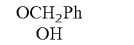)

PREPARATION EXAMPLES

The following abbreviations were used in this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, [M+H]$^+$=molecular mass of the molecular cation, [M−H]$^-$=molecular mass of the molecular anion.

The following LC-MS methods were used to characterize the compounds:

Method C

MS  ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da.

LC  1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile.

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method D

MS  ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da.

Method D -continued

LC  Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile.

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method F

MS  ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da.

LC  HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1).

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Example 1

Preparation of enantioenritched 4-[(3R)-3-Cyano-3-(3,5-dichloro-phenyl)-4,4,4-trifluoro-butyryl]-2-methyl-benzoic acid tert-butyl ester

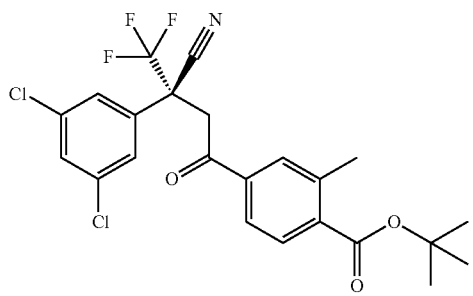 [SMILES: Cc1cc(C(=O)C[C@](C#N)(c2cc(Cl)cc(Cl)c2)C(F)(F)F)ccc1C(=O)OC(C)(C)C]

Potassium cyanide (6.465 g, 99.283 mmol) and acetone cyanohydrin (23.9 ml, 261.272 mmol) were added to a solution of 4-[(E)-3-(3,5-Dichloro-phenyl)-4,4,4-trifluoro-but-2-enoyl]-2-methyl-benzoic acid tert-butyl ester (40.000 g, 87.091 mmol) in toluene (600.0 ml). To this vigorously stirred suspension was added 9-anthrylmethyl quininium chloride (7.200 g, 13.064 mmol). The reaction mixture was stirred at 60° C. for 2 hours and at room temperature during 63 hours. At this time water was added and the reaction mixture was extracted with dichloromethane (3×). The crude product was purified by flash chromatography (0% to 5% ethyl acetate in cyclohexane) to afford 4-[(R)-3-Cyano-3-(3,5-dichloro-phenyl)-4,4,4-trifluoro-butyryl]-2-methyl-benzoic acid tert-butyl ester (35.80 g, 67.6%) as a white amorphous solid. Chiral HPLC analysis (Chiralpack IB, Heptane:2-propanol=98:2 1 ml/min): retention time 8.11 minutes (minor enantiomer, 5%), 9.95 minutes (major enantiomer, 95%)

$^1$H NMR (400 MHz, CDCl$_3$) δ 7.89 (d, 1H), 7.78-7.72 (m, 2H), 7.48 (s, 2H), 7.46-7.42 (m, 1H), 4.17 (d, 1H), 4.02 (d, 2H), 2.62 (s, 3H), 1.62 (s, 9H)

Example 2

Preparation of 9-anthrylmethyl quinidinium chloride

A solution of 9-chloromethyl-anthracene (0.91 g, 1.3 eq, 0.40 mmol) and quinidine [CAS=56-54-2] (1 g, 0.38) in toluene (10 ml) was heated at 90° C. for 18 hours. The reaction mixture was filtered, washed with n-heptane. The solid was recrystallised from chloroform and n-heptane to afford the title product (1.69 g) as a yellow solid. Preparation of this compound is also reported in dissertation: contributions to the asymmetric catalysis of c-c couplings, and to the chemical induction of cardiomyogenesis from embryonic stem cells, bianca seelig, university köhl 2009.

Example 3

Preparation of enantioenritched 4-[(3S)-3-Cyano-3-(3,5-dichloro-phenyl)-4,4,4-trifluoro-butyryl]-2-methyl-benzoic acid tert-butyl ester

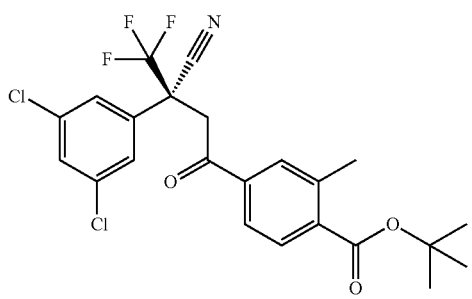 [SMILES: Cc1cc(C(=O)C[C@@](C#N)(c2cc(Cl)cc(Cl)c2)C(F)(F)F)ccc1C(=O)OC(C)(C)C]

Potassium cyanide (0.021 g, 0.32 mmol) and acetone cyanohydrin (0.086 mg, 1.01 mmol) were added to a solution tert-butyl 4-[(E)-3-(3,5-dichlorophenyl)-4,4,4-trifluoro-but-2-enoyl]-2-methyl-benzo (0.150 mg, 0.326 mmol) in toluene (1.0 ml). To this vigorously stirred suspension was added 9-anthrylmethyl quinidinium chloride (0.054 g, 0.098 mmol). The reaction mixture was stirred at 45° C. for 18 hours. At this time water was added and the reaction mixture was extracted with toluene (3×). The crude product was purified by flash chromatography (0% to 5% ethyl acetate in cyclohexane) to afford tert-butyl 4-[(3S)-3-cyano-3-(3,5-dichlorophenyl)-4,4,4-trifluoro-butanoyl]-2-methyl-benzoate (0.080 g, 50%) as a white foam.
Chiral HPLC analysis (Chiralpack IB, Heptane:2-propanol=98:2 1 ml/min): retention time 7.64 minutes (major enantiomer, 78.5%), 9.53 minutes (minor enantiomer, 21.5%). $^1$H NMR (400 MHz, CDCl$_3$) δ 7.89 (d, 1H), 7.78-7.72 (m, 2H), 7.48 (s, 2H), 7.46-7.42 (m, 1H), 4.17 (d, 1H), 4.02 (d, 2H), 2.62 (s, 3H), 1.62 (s, 9H)

Example 4

Preparation of enantioenritched (3R)-3-(3,5-dichlorophenyl)-3-(trifluoromethyl)pyrrolidine-2,5-dione

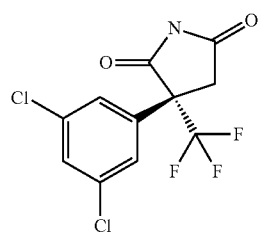 [SMILES: O=C1C[C@](c2cc(Cl)cc(Cl)c2)(C(F)(F)F)C(=O)N1]

Hydrogen peroxide (aq. 30%, 2.0 mL) was added to sulfuric acid (96%, 15.0 mL) slowly at <0° C. followed by tert-butyl 4-[(3R)-3-cyano-3-(3,5-dichlorophenyl)-4,4,4-trifluoro-butanoyl]-2-methyl-benzoate (600 mg) in dichloromethane (6.0 mL). The reaction mixture was stirred for 30 min. at 0° C. The reaction mixture was added on ice, treated with saturated aq. Na$_2$SO$_3$ and extracted with dichloromethane (3×). The combined organic phase were dried (Na$_2$SO$_4$), evaporated giving 1.03 g of yellowish foam. It was dissolved in methanol (8 mL) and treated with 8M sodium hydroxide (3 mL). The reaction mixture was stirred at 30 min at RT, acidified with conc. HCl and extracted with dichloromethane. The organic phase was washed with water, NaHCO$_3$ (aq., sat.), water. It was dried (Na$_2$SO$_4$) and evaporated giving the title compound as a white solid 450 mg (70%).

$^1$H-NMR (400 MHz, CDCl$_3$): δ 3.49 (d, J=18.5 Hz), 3.25 (d, J=18.5 Hz), 7.47 (s, 1H), 7.57 (s, 2H), 8.53 (bs, 1H) ppm.
$^{13}$C-NMR (101 MHz, CDCl$_3$): δ 39.0, 56.8 (q, J=27 Hz), 123.7 (q, J=284 Hz), 126.6), 130.14, 134.4, 136.0, 170.4, 171.6 ppm.
$^{19}$F-NMR (377 MHz, CDCl$_3$): δ −71.6 ppm.
LC/MS (ES-): 310 (M−H)$^−$, R$_t$=1.72 min
GC/MS (CI): 312 (M+H)$^+$, R$_t$=6.25 min
m.p.=138-141° C.

Example 5

Preparation of (3R)-3-(3,5-dichlorophenyl)-3-(trifluoromethyl)pyrrolidine

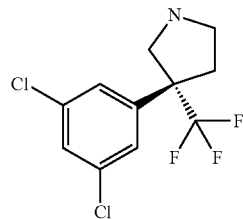 [SMILES: FC(F)(F)[C@@]1(c2cc(Cl)cc(Cl)c2)CCNC1]

To a solution of 3-(3,5-dichlorophenyl)-3-(trifluoromethyl)pyrrolidine-2,5-dione (0.02 g) in dry THF (0.5 ml) were added sequentially BF$_3$ etherate (0.109 g, 6 equiv.) and borane-THF complex 1M in THF (1.4 g, 24 equiv.) The reaction stirred at 40° C. for 18 h. After cooling to room temperature, HCl (aq. 4M solution, 1 ml) was added to the mixture and heated for additional 30 minutes at 40° C. After cooling to room temperature, the reaction mixture was washed with Et₂O. The aqueous phase was basified to pH-10 with NaOH and extracted with ethyl acetate (3×). The combined ethyl acetate extracts were dried (Na₂SO₄) and evaporated. The crude product was purified by column chromatography (silica, eluent: AcOEt with 1% Et₃N and 1% MeOH) giving 3.5 mg (19%) of the title compound as a colorless solid.

Chiral HPLC analysis (Chiralpack IA, Heptane:2-propanol:diethylamine=70:30:0.1, 1 ml/min): retention time 5.15 minutes (minor enantiomer, <15%), 6.96 minutes (major enantiomer, >75%).

¹H-NMR (400 MHz, CDCl₃): δ=7.36 (t, 1H); 7.26 (d, 2H, 0.73 Hz); 3.76 (d, 1H, 12.8 Hz); 3.32-3.21 (m, 2H); 3.10-3.01 (m, 1H); 2.60-2.51 (m, 1H); 2.36-2.26 (m, 1H) ppm.
LC/MS (ES-): 284 (M+H)⁺, R$_t$=1.07 min Example 6

Preparation of enantioenritched (3R)-3-(3,5-dichlorophenyl)-1-methyl-3-(trifluoromethyl)pyrrolidine-2,5-dione

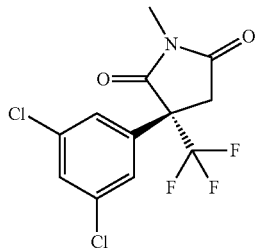 [SMILES: CN1C(=O)C[C@](c2cc(Cl)cc(Cl)c2)(C(F)(F)F)C1=O]

In a dried flask, under argon, to a solution of (3R)-3-(3,5-dichlorophenyl)-3-(trifluoromethyl)pyrrolidine-2,5-dione (99 mg) in dry DMF, was added potassium carbonate (0.117 g, 0.84 mmol), followed by iodomethane (0.1213 g, 0.84 mmol). The reaction mixture was stirred for 2 hours at from temperature. Water was added to the reaction mixture and it was extracted with Et2O. The organic phase was washed one time with HCl solution (0.5N), dried over Na2SO4 and evaporated in vacuum to give 62 mg (60%) as a yellow oil
¹H-NMR (400 MHz, CDCl₃): δ 3.12 (s, 3H); 3.22 (d, 1H, J=18.3 Hz), 3.44 (d, 1H, J=18 Hz), 7.45 (t, 1H), 7.58 (s, 2H), ppm.
GC/MS: RT=5.72 min; 326 (M+H)⁺

Example 7

Preparation of enantioenritched (3R)-3-(3,5-dichlorophenyl)-1-methyl-3-(trifluoromethyl)pyrrolidine

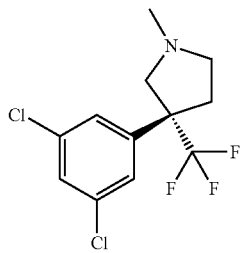 [SMILES: CN1CC[C@](c2cc(Cl)cc(Cl)c2)(C(F)(F)F)C1]

To a solution of (3R)-3-(3,5-dichlorophenyl)-1-methyl-3-(trifluoromethyl)pyrrolidine-2,5-dione (0.05 g) in dry THF (1 ml) were added sequentially BF₃ etherate (0.271 g, 0.975 mmol, 6 equiv.) and borane-THF complex 1M in THF (3.4 g, 24 equiv.) The reaction stirred at 40° C. for 18 h. After cooling to room temperature, HCl (aq. 4M solution, 1 ml) was added to the mixture and heated for additional 30 minutes at 40° C. After cooling to room temperature, the reaction mixture was washed with Et₂O. The aqueous phase was basified to pH~10 with NaOH and extracted with ethyl acetate (3×). The combined ethyl acetate extracts were dried (Na₂SO₄) and evaporated giving the desired product 10 mg (21%).

¹H-NMR (400 MHz, CDCl₃): δ 7.62 (S, 2H); 7.39 (t, 1H); 3.74-3.68 (m, 1H); 3.47-3.39 (m, 2H); 3.35-3.27 (m, 1H); 2.97 (s, 3H); 2.84-2.75 (m, 1H); 2.60-2.52 (m, 1H);
LC/MS (ES-): 298 (M+H)⁺, R$_t$=1.14 min Example 8

Preparation of (E)-3-(3,5-dichlorophenyl)-4,4,4-trifluoro-1-(2-furyl)but-2-en-1-one

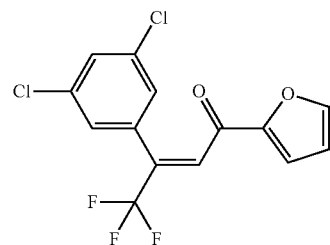 [SMILES: O=C(/C=C(\c1cc(Cl)cc(Cl)c1)C(F)(F)F)c1ccco1]

A flask was charged with starting material 1-(2-furyl)ethanone (5.00 g), 1-(3,5-dichlorophenyl)-2,2,2-trifluoro-ethanone (12.39 g), potassium carbonate (7.00 g), triethylamine (0.46 g) and 1,2-dichloroethane (50 mL). The reaction mixture was stirred and heated to reflux for 12 hours. Then potassium carbonate (6.00 g) was added and heating was continued for another 12 hours. The reaction mixture was diluted with dichloromethane, washed with water (2×) and the organic phase was dried over Na₂SO₄ and evaporated. Purification of the crude product via column chromatography (silica, n-heptane/ethyl acetate gradient) gave 10.8 g (71%) of the desired product.

¹H-NMR (400 MHz, CDCl₃): δ 7.66-7.64 (m, 1H); 7.42-7.39 (m, 2H); 7.26 (d, 1H, J=3.7 Hz); 7.18 (d, 2H, J=1.47 Hz) ppm.
¹³C-NMR (101 MHz, CDCl₃): δ 176.5; 152.5; 147.7; 138.8 (q); 135.0; 133.6; 129.5; 128.4 (q); 127.4; 122.1 (q); 119.5; 113.1 ppm.
25 ¹⁹F-NMR (377 MHz, CDCl₃): δ -67.09 ppm.
GC/MS (CI): 335 (M+H)⁺, R$_t$=5.73 min
m.p.=72-76° C.

Example 9

Preparation of enantioenritched 2-(3,5-dichlorophenyl)-4-(2-furyl)-4-oxo-2-(trifluoromethyl)butanenitrile

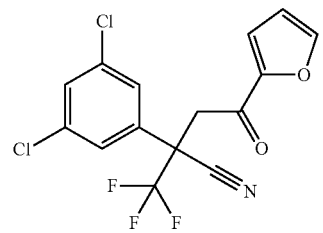 [SMILES: N#CC(CC(=O)c1ccco1)(c1cc(Cl)cc(Cl)c1)C(F)(F)F]

To a solution of (E)-3-(3,5-dichlorophenyl)-4,4,4-trifluoro-1-(2-furyl)but-2-en-1-one (0.200 g, 0.597 mmol) in toluene (3 mL) were added (R)-[1-(9-anthrylmethyl)-5-vinyl-quinuclidin-1-ium-2-yl]-(6-methoxy-4-quinolyl)methanol chloride (0.066 g, 0.119 mmol), acetone cyanohydrin (0.165 mL, 1.802 mmol) and potassium carbonate (0.09206 g, 0.657 mmol) sequentially. The reaction mixture was vigorously stirred at room temperature for 2 h. At this time aqueous solution of NH$_4$Cl was added and the reaction mixture was extracted with AcOEt, dried (Na$_2$SO$_4$) and evaporated. Purification of the crude product via column chromatography (silica, n-heptane/ethyl acetate gradient) gave 165 mg (76%) of the desired product as white semisolid.

Chiral HPLC analysis (Chiralpack AS-R3, Acetonitrile:MeOH:Water=45:5:50, 1 ml/min): retention time 56.73 minutes (minor enantiomer, 13.4%), 59.31 minutes (major enantiomer, 86.6%). (The identity of the stereochemistry was not determined. It is expected that the alternative isomer could be produced in enantiomeric excess with use an appropriate catalyst with reversed stereochemistry.)

$^1$H-NMR (400 MHz, CDCl$_3$): δ 7.68-7.67 (m, 1H); 7.51 (s, 2H); 7.46 (t, 1H); 7.30-7.27 (m, 1H); 6.64 (dd, 1H, J=1.83 Hz, J=3.67 Hz); 4.48 (d, 1H, J=18.3 Hz); 3.89 (d, 1H, J=18.3 Hz) ppm GC/MS (CI): 362 (M+H)$^+$, R$_t$=6.60 min Example 10

Preparation of enantioenritched 3-cyano-3-(3,5-dichlorophenyl)-4,4,4-trifluoro-butanoic acid

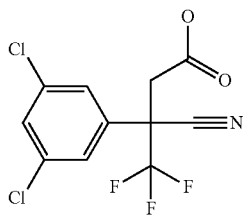 [SMILES: N#CC(CC(=O)O)(c1cc(Cl)cc(Cl)c1)C(F)(F)F]

2-(3,5-dichlorophenyl)-4-(2-furyl)-4-oxo-2-(trifluoromethyl)butanenitrile (0.150 g, 0.414 mmol) was dissolved in a mixture of dichloromethane, acetonitrile and water (1:1:2). Sodium periodate (0.627 g, 2.900 mmol) was added, followed by ruthenium chloride hydrate (0.003 g, 0.035 mmol). The reaction mixture was stirred at room temperature overnight. The reaction was diluted with CH2Cl2; the organic phase was washed with H$_2$O and dried over Na2SO4 giving 53 mg of violet solid.

$^1$H-NMR (400 MHz, CDCl$_3$): δ 7.49 (s, 1H); 7.46 (s, 2H); 3.42 (s, 2H) ppm

LC/MS: R$_t$=1.83 min; 310 (M−H)$^-$,

Example 11

Preparation of (E)-3-(3,5-dichlorophenyl)-4,4,4-trifluoro-1-pyrrol-1-yl-but-2-en-1-one

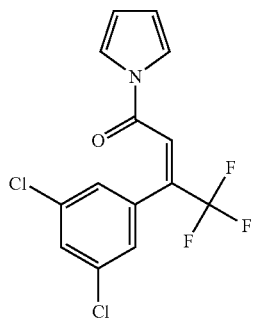 [SMILES: O=C(/C=C(\c1cc(Cl)cc(Cl)c1)C(F)(F)F)n1cccc1]

A suspension of sodium hydride (0.117 g) in 1,2-dimethoxyethane (5 ml) was cooled to 0° C. and a solution of 2-diethoxyphosphoryl-1-pyrrol-1-yl-ethanone (0.754 g) in 1,2-dimethoxyethane (2 ml) was added drop-wise and stirred for 20 min. To the reaction mixture was added drop-wise a solution of 1-(3,5-dichlorophenyl)-2,2,2-trifluoro-ethanone (0.503 g) in 1,2-dimethoxyethane (2 ml). The reaction was stirred for a further 30 min at 0° C., then allowed to warm to RT and stirred for a further 2 h. The reaction mixture was quenched by cautious addition of saturated NH$_4$Cl(10 ml) solution over ice and extracted with ethyl acetate (3×15 ml). The combined organics were passed through a PTFE membrane and concentrated in vacuo to give a turbid orange oil, which was taken up in toluene and purified by column-chromatography on a pre-packed silica column eluting with heptanes/ethyl acetate to give the title compound as a pale yellow oil (0.313 g)

$^1$H-NMR: (400 MHz, CDCl$_3$) δ$_H$ ppm 7.40 (m, 2H), 7.20 (m, 3H), 7.18-7.19 (m, 1H), 6.33-6.35 (m, 2H).

Example 12

Preparation of enantioenritched 2-(3,5-dichlorophenyl)-4-oxo-4-pyrrol-1-yl-2-(trifluoromethyl)-butanenitrile

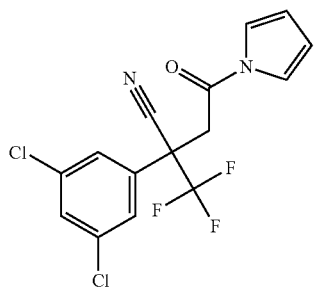 [SMILES: N#CC(CC(=O)n1cccc1)(c1cc(Cl)cc(Cl)c1)C(F)(F)F]

To a suspension of potassium carbonate (0.144 g) and (R)-(6-methoxy-4-quinolyl)-[(2S,4S,5R)-1-[(2,3,4,5,6-pentafluorophenyl)methyl]-5-vinyl-quinuclidin-1-ium-2-yl]methanol bromide (0.126 g) in toluene (4 ml) was added a solution of (E)-3-(3,5-dichlorophenyl)-4,4,4-trifluoro-1-pyrrol-1-yl-but-2-en-1-one (0.313 g) in toluene (2 ml) followed by 2-hydroxy-2-methyl-propanenitrile (100 µl) in toluene (2 ml). The reaction mixture was heated to 45° C. overnight before potassium cyanide (0.077 g), a drop of water and a further aliquot of the 2-hydroxy-2-methyl-propanenitrile (100 µl) were added and the reaction mixture heated to 60° C. for a further 4 h. The reaction was poured onto saturated NH$_4$Cl solution and extracted with dichloromethane (3×25 ml). The combined organics were washed with brine, dried over Na$_2$SO$_4$ and concentrated in vacuo to give a dark amber gum, which was purified by column-chromatography on a pre-packed silica column eluting with heptanes/ethyl acetate to give the title compound as a pale yellow oil (0.084 g). Chiral HPLC analysis (Chiralpack IA, Heptane:isopropanol=95:5, 1 ml/min): retention time 6.09 minutes (minor enantiomer, 34%), 6.96 minutes (major enantiomer, 66%). (The identity of the stereochemistry was not determined. It is expected that the alternative isomer could be produced in enantiomeric excess with use of an appropriate catalyst with reversed stereochemistry)

$^1$H-NMR (400 MHz, CDCl$_3$) δ$_H$ ppm 7.48-7.51 (m, 2H), 7.45-7.48 (m, 1H), 7.21-7.26 (m, 2H), 6.37 (m, 1H), 3.90 (m, 1H).

Example 13

Preparation of enantioenritched methyl 3-cyano-3-(3,5-dichlorophenyl)-4,4,4-trifluoro-butanoate

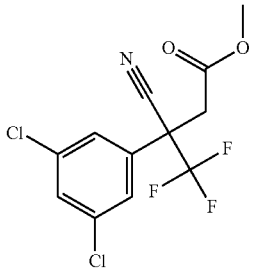 [SMILES: COC(=O)CC(C#N)(c1cc(Cl)cc(Cl)c1)C(F)(F)F]

Enantioenritched 2-(3,5-Dichlorophenyl)-4-oxo-4-pyrrol-1-yl-2-(trifluoromethyl)butanenitrile (22 mg) was taken up in methanol (2 ml) and sodium methoxide (33 mg) was added. The reaction was stirred at ambient temperature for 1 h before saturated NH$_4$Cl solution (4 ml) was added and the mixture extracted with EtOAc (3×8 ml). The organic portions were combined, passed through a PTFE membrane and concentrated in vacuo to give a colourless semi-solid, which was then taken up in toluene and purified by column-chromatography on silica, eluting with cyclohexane/EtOAc to give the title compound as a colourless oil (7 mg).

$^1$H-NMR (400 MHz, CHLOROFORM-d): δ$_H$ ppm 7.45-7.49 (m, 3H), 3.68 (s, 3H), 3.36-3.39 (m, 1H).

Example 14

Preparation of enantioenritched 4-(3,5-dichlorophenyl)-4-(trifluoromethyl)pyrrolidin-2-one

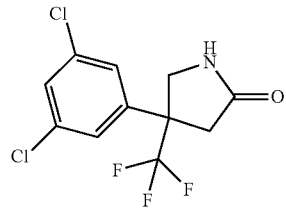 [SMILES: O=C1CC(c2cc(Cl)cc(Cl)c2)(C(F)(F)F)CN1]

To a solution of methyl enantioenritched 3-cyano-3-(3,5-dichlorophenyl)-4,4,4-trifluoro-butanoate (7 mg) in methanol (0.75 ml) was added cobalt (II) chloride hexahydrate (17 mg) followed by sodium borohydride (12 mg). The reaction mixture was stirred for 2 h at ambient temperature before it was concentrated in vacuo and the residue was taken up in dichloromethane (2 ml) and filtered through Celite. The filter cake washed with further dichloromethane (3×2 ml) and the combined filtrates were concentrated in vacuo to give a black film, which was purified by column-chromatography on silica, eluting with 5-10% methanol/dichloromethane to give the title compound as a colourless oil (6 mg)

$^1$H-NMR (400 MHz, CDCl$_3$): δ$_H$ ppm 7.41 (t, 1H), 7.15-7.18 (m, 2H), 5.91 (br.s., 1H), 4.12 (dd, 2H), 3.81 (d, 2H).

Example 15

Preparation of methyl 4-[(3S)-3-(3,5-dichlorophenyl)-3-(trifluoromethyl)pyrrolidin-1-yl]-2-methyl-benzoate

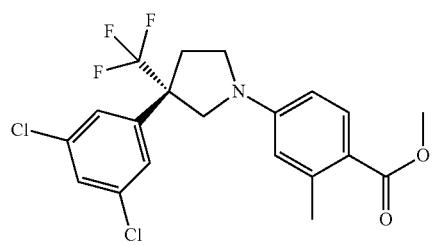 [SMILES: COC(=O)c1ccc(N2CC[C@@](c3cc(Cl)cc(Cl)c3)(C(F)(F)F)C2)cc1C]

To a degassed solution of (3S)-3-(3,5-dichlorophenyl)-3-(trifluoromethyl)pyrrolidine (100.0 mg) and methyl 4-bromo-2-methyl-benzoate (88.7 mg) in dry toluene (1.8 mL) were added sequentially sodium tert-butoxide (34.9 mg), Xantphos (12.6 mg) and Pd$_2$(dba)$_3$.CHCl$_3$ (6.6 mg). The reaction mixture was stirred under argon at 80° C. overnight. The reaction mixture was diluted with AcOEt and washed two times with water and brine. The organic phase was dried (Na2SO4), filtered and evaporated to give 150 mg of red orange oil. The crude product was purified by silica gel column chromatography (Heptane in 0-100% of AcOEt) giving 51 mg (33%) of a white solid.

$^1$H-NMR (400 MHz, CDCl3): δ 7.93 (d, 1H, J=8.5 Hz); 7.40 (t, 1H, J=2 Hz); 7.30 (s, 2H); 6.45-6.38 (m, 2H), 4.13 (d, 1H, J=10.6 Hz); 3.85 (s, 3H); 3.82 (d, 1H, J=10.6 Hz); 3.66-3.48 (m, 2H); 2.92-2.82 (m, 1H); 2.63 (s, 3H); 2.60-2.49 (m, 1H) ppm.

$^{19}$F-NMR (400 MHz, CDCl3): 6-73.11 ppm.
$^{13}$C-NMR (400 MHz, CDCl3): δ 167.74; 148.89; 142.98; 140.46; 135.30; 133.02; 128.87; 126.83; 117.39; 114.25; 108.78; 54.47; 53.17; 51.21; 46.40; 31.72; 22.71 ppm.

Example 16

Preparation of 4-[(3S)-3-(3,5-dichlorophenyl)-3-(trifluoromethyl)pyrrolidin-1-yl]-2-methyl-benzoic acid

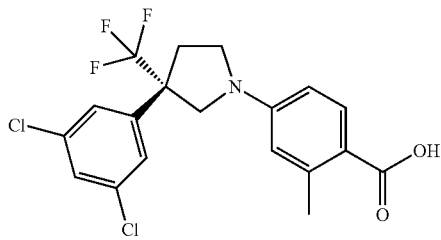 [SMILES: Cc1cc(N2CC[C@@](c3cc(Cl)cc(Cl)c3)(C(F)(F)F)C2)ccc1C(=O)O]

Methyl 4-[(3S)-3-(3,5-dichlorophenyl)-3-(trifluoromethyl) pyrrolidin-1-yl]-2-methyl-benzoate (31.0 mg) was dissolved in tetrahydrofuran (0.36 mL). Potassium hydroxide (300 mg) in MeOH/H2O (0.36 ml/0.36 ml) was added at RT. The reaction was stirred at 40° C. for 72 h. The aqueous layer was extracted with ether, then it was acidified until pH=1 with aq. HCl and extracted with dichloromethane. The organic phase was dried (Na$_2$SO$_4$), filtered and evaporated in vacuum to give 26 mg (85%) of the desired product as a white solid.

$^1$H-NMR (400 MHz, CDCl3): δ 8.01 (d, 1H, J=8 Hz); 7.40 (t, 1H, J=2 Hz); 7.30 (s, 2H); 6.48-6.40 (m, 2H), 4.13 (d, 1H, J=11 Hz); 3.82 (d, 1H, J=11 Hz); 3.66-3.48 (m, 2H); 2.92-2.82 (m, 1H); 2.65 (s, 3H); 2.62-2.48 (m, 1H) ppm.

Example 17

Preparation of 4-[(3S)-3-(3,5-dichlorophenyl)-3-(trifluoromethyl)pyrrolidin-1-yl]-N-(1,1-dioxothietan-3-yl)-2-methyl-benzamide

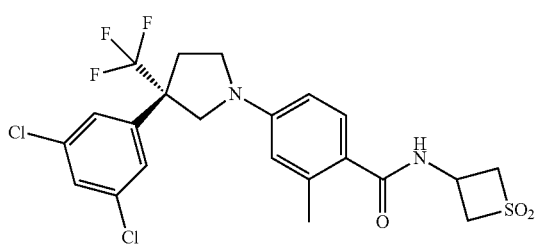 [SMILES: Cc1cc(N2CC[C@@](c3cc(Cl)cc(Cl)c3)(C(F)(F)F)C2)ccc1C(=O)NC1CS(=O)(=O)C1]

To a suspension of 4-[(3S)-3-(3,5-dichlorophenyl)-3-(trifluoromethyl)pyrrolidin-1-yl]-2-methyl-benzoic acid (20.0 mg) in dry dichloromethane (1 mL) were added sequentially 3-hydroxytriazolo[4,5-b]pyridine (7.2 mg, 1.100), 3-(ethyliminomethyleneamino)-N,N-dimethyl-propan-1-amine hydrochloride (10.1 mg) and a solution of 1,1-dioxothietan-3-amine hydrochloride (9.1 mg) and triethylamine (14.5 mg) in dichloromethane. The yellow solution stirred under argon for 20 h at RT. The reaction mixture was diluted with DCM, washed with a saturated solution of NH$_4$Cl and brine. The organic phase was dried (Na$_2$SO$_4$), filtered and evaporated in vacuum to give 16 mg (65%) of white solid.

$^1$H-NMR (400 MHz, CDCl$_3$): δ 7.42-7.38 (m, 2H); 7.31-7.29 (m, 2H); 6.44-6.39 (m, 2H); 6.33 (d, 1H, 6.6 Hz); 4.91-4.83 (m, 1H); 4.66-4.57 (m, 2H); 4.10 (d, 1H, J=10.6 Hz); 4.06-3.98 (m, 2H); 3.82 (d, 1H, J=10.6 Hz); 3.64-3.45 (m, 2H); 2.92-2.84 (m, 1H); 2.61-2.53 (m, 1H); 2.60 (s, 3H) ppm.

Chiral HPLC analysis (Chiralpack® IA 0.46 cm×10 cm, Heptane:2-propanol:diethylamine=70:30:0.1, Flow rate: 1 ml/min; Detection: 288 nm): retention time 5.61 minutes (major enantiomer, >99%), 8.46 minutes (minor enantiomer, not observed).

Example 18 (Reference)

Preparation of (3R)-3-(3,5-dichlorophenyl)-3-(trifluoromethyl)pyrrolidine and (3S)-3-(3,5-dichlorophenyl)-3-(trifluoromethyl)pyrrolidine

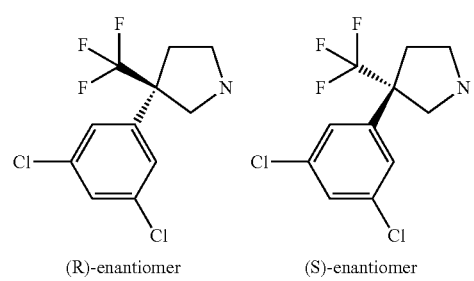 [SMILES: FC(F)(F)[C@@]1(c2cc(Cl)cc(Cl)c2)CCNC1 ; FC(F)(F)[C@]1(c2cc(Cl)cc(Cl)c2)CCNC1]

(R)-enantiomer        (S)-enantiomer

Preparative Method:
Column: 250×30 mm CHIRALPAK® ID 5 μm
Mobil phase: Carbon dioxide (Methanol+1% Diethylamine) 95/5
Flow rate: 120 mL/min
Detection: UV 220 nm
Outlet Pressure: 130 bar
Temperature: 25° C.
Analytical Method:
Column: 250×4.6 mm CHIRALPAK® IA 5 μm
Mobil phase: Heptane:2-propanol: diethylamine=70:30:0.1
Flow rate: 1 mL/min
Detection: UV 270 nm
Temperature: 25° C.
Retention time 5.15 minutes (S-enantiomer), 6.96 minutes (R-enantiomer)

391 mg of (3S)-3-(3,5-dichlorophenyl)-3-(trifluoromethyl) pyrrolidine (first eluting enantiomer, >99% enantiomeric excess) and 400 mg of (3R)-3-(3,5-dichlorophenyl)-3-(trifluoromethyl)pyrrolidine (second eluting enantiomer, >98% enantiomeric excess were prepared from 958 mg of racemic 3-(3,5-dichlorophenyl)-3-(trifluoromethyl)pyrrolidine.

(Enantiomeric excess is defined as the absolute difference between the mole fraction of each enantiomer.)

The invention claimed is:
1. A compound, wherein the compound is a compound of formula IIc,

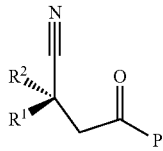

(IIc)

wherein
P is alkyl, hydroxy, alkoxy, aryloxy, alkylsulfinyl, or arylsulfinyl, each optionally substituted,
R$^1$ is chlorodifluoromethyl or trifluoromethyl, and
R$^2$ is aryl or heteroaryl, each optionally substituted;
a compound of formula III,

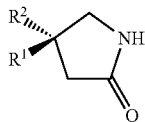

(III)

wherein
R$^1$ is chlorodifluoromethyl or trifluoromethyl, and
R$^2$ is aryl or heteroaryl, each optionally substituted;
a compound of formula IV,

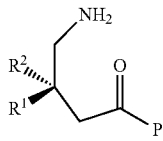

(IV)

wherein
P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom,
R$^1$ is chlorodifluoromethyl or trifluoromethyl, and
R$^2$ is aryl or heteroaryl, each optionally substituted;
a compound of formula V,

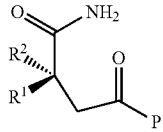

(V)

wherein
P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom,
R$^1$ is chlorodifluoromethyl or trifluoromethyl, and
R$^2$ is aryl or heteroaryl, each optionally substituted;

a compound of formula VI,

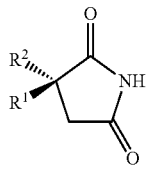

(VI)

wherein
R$^1$ is chlorodifluoromethyl or trifluoromethyl, and
R$^2$ is aryl or heteroaryl, each optionally substituted;
a compound of formula VII,

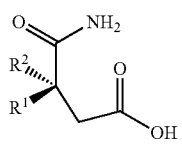

(VII)

wherein
R$^1$ is chlorodifluoromethyl or trifluoromethyl, and
R$^2$ is aryl or heteroaryl, each optionally substituted;
a compound of formula VIII,

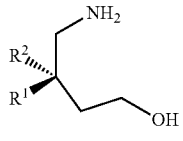

(VIII)

wherein
R$^1$ is chlorodifluoromethyl or trifluoromethyl, and
R$^2$ is aryl or heteroaryl, each optionally substituted;
a compound of formula X,

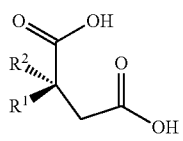

(X)

wherein
R$^1$ is chlorodifluoromethyl or trifluoromethyl, and
R$^2$ is aryl or heteroaryl, each optionally substituted;
a compound of formula XIV,

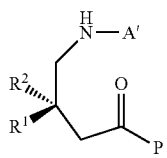

(XIV)

wherein
P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, R¹ is chlorodifluoromethyl or trifluoromethyl, R² is aryl or heteroaryl, each optionally substituted, and A' is optionally substituted aryl or optionally substituted heteroaryl;

a compound of formula XV,

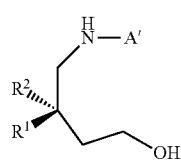
(XV)

wherein

R¹ is chlorodifluoromethyl or trifluoromethyl,

R² is aryl or heteroaryl, each optionally substituted, and

A' is optionally substituted aryl or optionally substituted heteroaryl;

a compound of formula XVIII,

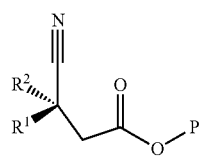
(XVIII)

wherein

P is alkyl, aryl or heteroaryl, each optionally substituted, wherein the heteroaryl is connected at P via a ring carbon atom, R¹ is chlorodifluoromethyl or trifluoromethyl, and R² is aryl or heteroaryl, each optionally substituted; or a compound of formula XII,

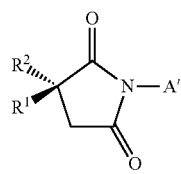
(XII)

wherein

R¹ is chlorodifluoromethyl or trifluoromethyl,

R² is aryl or heteroaryl, each optionally substituted, and

A' is optionally substituted aryl or optionally substituted heteroaryl.

2. A compound of claim 1, wherein the compound is of formula XII,

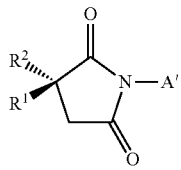
(XII)

wherein

R¹ is chlorodifluoromethyl or trifluoromethyl,

R² is aryl or heteroaryl, each optionally substituted, and

A' is optionally substituted aryl or optionally substituted heteroaryl.

3. A mixture comprising a compound of IIc and a compound of formula IIcA,

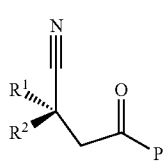
(IIcA)

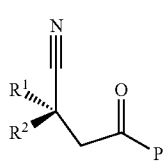
(IIc)

wherein

P is alkyl, hydroxy, alkoxy, aryloxy, alkylsulfinyl, or arylsulfinyl, each optionally substituted, R¹ is chlorodifluoromethyl or trifluoromethyl, R² is aryl or heteroaryl, each optionally substituted, and wherein the mixture is enriched for the compound of formula IIc;

a mixture comprising a compound of formula III and a compound of formula IIIA,

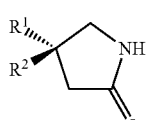
(IIIA)

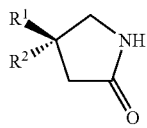
(III)

wherein

R¹ is chlorodifluoromethyl or trifluoromethyl,

R² is aryl or heteroaryl, each optionally substituted, and wherein the mixture is enriched for the compound of formula III;

a mixture comprising a compound of formula IV and a compound of formula IVA,

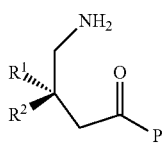

(IVA)

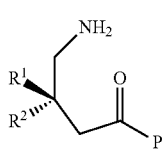

(IV)

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, R¹ is chlorodifluoromethyl or trifluoromethyl, R² is aryl or heteroaryl, each optionally substituted, and wherein the mixture is enriched for the compound of formula IV;

a mixture comprising a compound of formula V and a compound of formula VA,

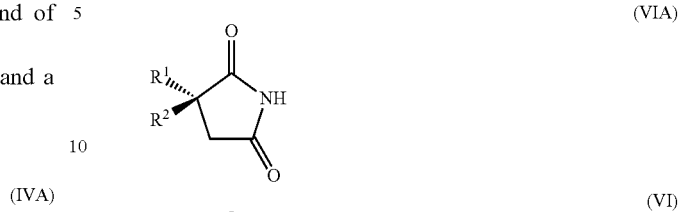

(VA)

(V)

wherein

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, R¹ is chlorodifluoromethyl or trifluoromethyl, R² is aryl or heteroaryl, each optionally substituted, and wherein the mixture is enriched for the compound of formula V;

a mixture comprising a compound of formula VI and a compound of formula VIA

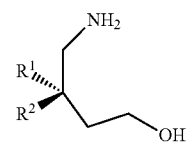

(VIA)

(VI)

wherein

R¹ is chlorodifluoromethyl or trifluoromethyl,

R² is aryl or heteroaryl, each optionally substituted, and wherein the mixture is enriched for the compound of formula VI;

a mixture comprising a compound of formula VII and a compound of formula VIIA

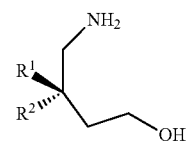

(VIIA)

(VII)

wherein

R¹ is chlorodifluoromethyl or trifluoromethyl,

R² is aryl or heteroaryl, each optionally substituted, and wherein the mixture is enriched for the compound of formula VII;

a mixture comprising a compound of formula VIII and a compound of formula VIIIA

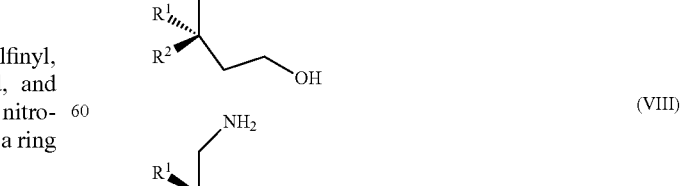

(VIIIA)

(VIII)

wherein

R¹ is chlorodifluoromethyl or trifluoromethyl,

R² is aryl or heteroaryl, each optionally substituted, and wherein the mixture is enriched for the compound of formula VIII;

a mixture comprising a compound of formula X and a compound of formula XA

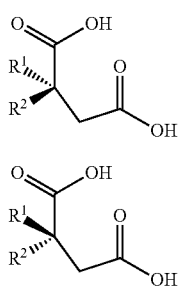

R¹ is chlorodifluoromethyl or trifluoromethyl,

R² is aryl or heteroaryl, each optionally substituted, and wherein the mixture is enriched for the compound of formula X;

a mixture comprising a compound of formula XII and a compound of formula XIIA

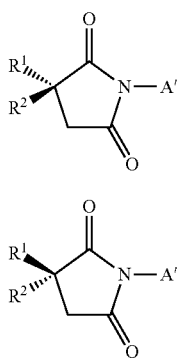

wherein

R¹ is chlorodifluoromethyl or trifluoromethyl,

R² is aryl or heteroaryl, each optionally substituted,

A' is optionally substituted aryl or optionally substituted heteroaryl, and wherein the mixture is enriched for the compound of formula XII;

a mixture comprising a compound of formula XIV and a compound of formula XIVA

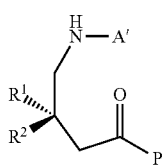

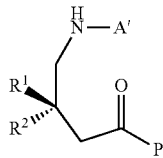

wherein

P is hydroxy, alkoxy, aryloxy, alkylsulfinyl, arylsulfinyl, aryl or heteroaryl, each optionally substituted, and wherein the heteroaryl contains at least one ring nitrogen atom, and the heteroaryl is connected at P via a ring nitrogen atom, R¹ is chlorodifluoromethyl or trifluoromethyl, R² is aryl or heteroaryl, each optionally substituted, A' is optionally substituted aryl or optionally substituted heteroaryl, and wherein the mixture is enriched for the compound of formula XIV;

a mixture comprising a compound of formula XV and a compound of formula XVA

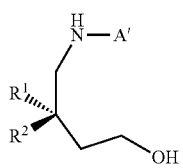

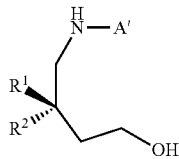

wherein

R¹ is chlorodifluoromethyl or trifluoromethyl,

R² is aryl or heteroaryl, each optionally substituted,

A' is optionally substituted aryl or optionally substituted heteroaryl, and wherein the mixture is enriched for the compound of formula XV;

a mixture comprising a compound of formula XVIII and a compound of formula XVIIIA

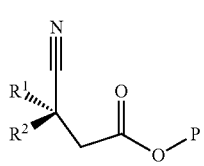

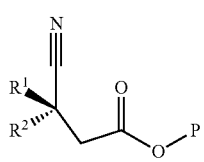

wherein

P is alkyl, aryl or heteroaryl, each optionally substituted, wherein the heteroaryl is connected at P via a ring carbon atom, R¹ is chlorodifluoromethyl or trifluoromethyl, R² is aryl or heteroaryl, each optionally substituted, and wherein the mixture is enriched for the compound of formula XVIII; or a compound of formula XXIX, XXX, XXXI, XXXII, or XXXIII

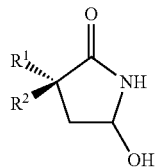

(XXIX)

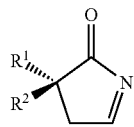

(XXX)

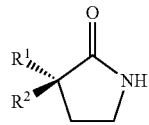

(XXXI)

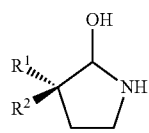

(XXXII)

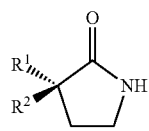

(XXXIII)

wherein

R¹ is chlorodifluoromethyl or trifluoromethyl, and

R² is aryl or heteroaryl, each optionally substituted.

* * * * *